(12) United States Patent
Reed et al.

(10) Patent No.: US 6,727,356 B1
(45) Date of Patent: Apr. 27, 2004

(54) FLUORESCENT QUENCHING DETECTION REAGENTS AND METHODS

(75) Inventors: Michael W. Reed, Seattle, WA (US); Eugeny Alexander Lukhtanov, Bothell, WA (US); Alexander A. Gall, Bothell, WA (US); Robert O. Dempcy, Kirkland, WA (US)

(73) Assignee: Epoch Pharmaceuticals, Inc., Redmond, WA (US)

( * ) Notice: Subject to any disclaimer, the term of this patent is extended or adjusted under 35 U.S.C. 154(b) by 0 days.

(21) Appl. No.: 09/457,616

(22) Filed: Dec. 8, 1999

(51) Int. Cl.[7] .................. C07H 19/00; C07H 21/02; C07H 21/04; C12Q 1/68
(52) U.S. Cl. ................. 536/26.6; 536/22.1; 536/23.1; 536/24.3; 536/25.3; 536/25.32; 435/6
(58) Field of Search ............... 435/6; 536/22.1, 536/23.1, 24.3, 25.3, 25.32, 26.6

(56) References Cited

U.S. PATENT DOCUMENTS

| | | | |
|---|---|---|---|
| 5,304,645 A | 4/1994 | Klein et al. | 544/10.2 |
| 5,502,177 A | * 3/1996 | Matteucci et al. | 536/26.6 |
| 5,801,155 A | 9/1998 | Kutyavin et al. | 514/44 |
| 5,952,202 A | 9/1999 | Aoyagi et al. | 435/91.2 |

FOREIGN PATENT DOCUMENTS

| | | | |
|---|---|---|---|
| WO | WO 97/39008 | 10/1997 | |
| WO | WO-9951621 | * 10/1999 | |

OTHER PUBLICATIONS

Asanuma et al., "Photo–Responsive Oligonucleotides Carrying Azobenzene in the Side–Chains", *Tetrahedron Letters*, 39:9015–9018 (1998).

"98 Catalogue", 1998 Amersham Pharmacia Biotech S–Hertogenbosch, Netherlands XP002172887, p. 127, FluoroBlue.

Lee et al. "Allelic discrimination by nick–translation PCR with fluorogenic probes", *Nucleic Acid Research, GB, Oxford University Press Surrey*, 21:(16) 3761–3766 (Aug. 11, 1993).

Nazarenko et al, "A closed tube format for amplification and detection of DNA based on energy transfer", *Nucleic Acids Research*, 25:(12) 2516–2521 (1997).

Sokol, et al., "Real time detection of DNA–RNA hybridization in living cells", *Proc. Nat'l Acad. Sci.*, 95: 11538–11543 (Sep. 1998).

* cited by examiner

*Primary Examiner*—Jezia Riley
(74) *Attorney, Agent, or Firm*—Townsend and Townsend and Crew LLP

(57) ABSTRACT

Oligonucleotide-fluorophore-quencher conjugates wherein the fluorophore moiety has emission wavelengths in the range of about 300 to about 800 nm, and or where the quencher includes a substituted 4-(phenyldiazenyl) phenylamine structure provide improved signal to noise ratios and other advantageous characteristics in hybridization and related assays. The oligonucleotide-fluorophore-quencher conjugates can be synthesized by utilizing novel phosphoramidite reagents that incorporate the quencher moiety based on the substituted 4-(phenyldiazenyl) phenylamine structure, and or novel phosphoramidite reagents that incorporate a fluorophore moiety based on the substituted coumarin, substituted 7-hydroxy-3H-phenoxazin-3-one, or substituted 5,10-dihydro-10-[phenyl] pyrido[2,3-d;6,5-d']dipyrimidine-2,4,6,8-(1H,3H,7H,9H, 10H)-tetrone structure. Oligonucleotide-fluorophore-quencher-minor groove binder conjugates including a pyrrolo[4,5-e]indolin-7-yl}carbonyl)pyrrolo[4,5-e]indolin-7-yl]carbonyl}pyrrolo[4,5-e]indoline-7-carboxylate (DPI$_3$) moiety as the minor groove binder and the substituted 4-(phenyldiazenyl)phenylamine moiety as the quencher, were synthesized and have substantially improved hybridization and signal to noise ratio properties.

9 Claims, 4 Drawing Sheets

FLUORESCENT QUENCHING DETECTION REAGENTS AND METHODS

BACKGROUND OF THE INVENTION

1. Field of the Invention

The invention relates to oligonucleotide-quencher-fluorescent-dye conjugates having improved characteristics, and to reagents suitable for incorporating novel quencher and fluorescent dye moieties into oligonucleotides. The invention also relates to the use of oligonucleotide-quencher-fluorescent-dye conjugates in detection methods for nucleic acid targets.

2. Brief Description of the Prior Art

Synthetic oligonucleotides have been used for years as sequence specific probes for complementary DNA and RNA targets. These methods have broad application in forensics, molecular biology and medical diagnostics since they allow the identification and quantitation of specific nucleic acid targets. Early uses of DNA probes relied on radioactivity (typically $^{32}P$) as the label, while recent methods use reporter molecules which include chemiluminescent and fluorescent groups. Improved instrumentation has allowed the sensitivity of these spectroscopic methods to approach or surpass the radiolabeled methods. Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance ($R_0$) is described as the distance between the donor and acceptor molecules where the energy transfer is 50% efficient. Other mechanisms of fluorescence quenching are also known, such as, collisional and charge transfer quenching.

Typically detection methods based on FRET are designed in such a way that the donor fluorophore and acceptor molecules are in close proximity so that quenching of the donor fluorescence is efficient. During the assay, the donor and acceptor molecules are separated such that fluorescence occurs. FRET-based detection assays have been developed in the fields of nucleic acid hybridization and enzymology. Several forms of the FRET hybridization assays are reviewed (Nonisotopic DNA Probe Techniques, Academic Press, Inc., San Diego 1992, pp. 311–352).

Since its discovery, the polymerase chain reaction (PCR) has revolutionized molecular biology. This technique allows amplification of specific DNA sequences, thus allowing DNA probe assays to be executed from a single DNA target copy. PCR-based diagnostic assays have initially not been used routinely, in part due to problems with sample handling and possible contamination with non-source DNA. Recently, new homogeneous fluorescent-based DNA assays have been described which can detect the progress of PCR as it occurs ("real-time" PCR detection) using spectrofluorometric temperature cyclers. Two popular assay formats use DNA probes which become fluorescent as DNA amplification occurs (fluorogenic probes).

The first format for "real-time" PCR uses DNA probes known as "molecular beacons" (Tyagi et al., Nat. Biotech., 16: 49–53 (1998)). Molecular beacons have a hairpin structure wherein the quencher dye and reporter dye are in intimate contact with each other at the end of the stem of the hairpin. Upon hybridization with a complementary sequence, the loop of the hairpin structure becomes double stranded and forces the quencher and reporter dye apart, thus generating a fluorescent signal. Tyagi et al. reported use of the non-fluorescent quencher dyes including the dabcyl (4-{[4-(dimethylamino)phenyl]diazenyl}benzoyl moiety, absorbance max=453 nm) used in combination with fluorescent reporter dyes of widely varying emission wavelength (475–615 nm). At the time this was surprising since FRET requires significant overlap of the absorption spectrum of the quencher and of the emission spectrum of the reporter. In case of a dabcyl moiety containing (hereinafter "dabcyl") quencher and some fluorescent dyes, the spectral overlap was extremely low, yet quenching efficiency was high. Therefore it was proposed that the mechanism of quenching for the hairpin form of the beacons was not FRET, but collisional quenching. In fact, the UV spectra of the quencher changes in the hairpin form of the beacon, providing evidence of the molecular contact and thus of collisional quenching. A related detection method uses hairpin primers as the fluorogenic probe (Nazarenko et al., Nucl. Acid Res., 25: 2516–2521 (1997)).

The second format for "real-time" PCR uses DNA probes which are referred to as "5'-nuclease probes" (Lee et al., Nucl. Acid Res., 21: 3761–3766 (1993)). These fluorogenic probes are typically prepared with the quencher at the 3' terminus of a single DNA strand and the fluorophore at the 5' terminus. During each PCR cycle, the 5'-nuclease activity of Taq DNA polymerase cleaves the DNA strand, thereby separating the fluorophore from the quencher and releasing the fluorescent signal. The 5'-nuclease assay requires that the probe be hybridized to the template strand during the primer extension step (60–65° C.). They also disclose the simultaneous "real-time" detection of more than one polynucleotide sequence in the same assay, using more than one fluorophore/quencher pair. The 5'-nuclease PCR assay is depicted in FIG. 1.

Initially it was believed that 5'-nuclease probes had to be prepared with the quencher (usually tetramethylrhodamine (TAMRA)) positioned at an internal nucleotide in close proximity to the 5'-fluorophore (usually fluorescein (FAM) or tetrachlorofluorescein (TET)) to get efficient FRET. Later it was found that this is not necessary, and the quencher and the fluorophore can be located at the 3' and 5' end of the ODN, respectively. It has been proposed that the random coil structures formed by these fluorogenic probes in solution allow a 3'-quencher dye to pass within the Forster radius of the 5'-fluorophore during the excited state of the molecule.

A number of donor/acceptor pairs have previously been described, important to the present invention is dabcyl that is used for instance as a quencher of dansyl sulphonamide in chemosensors (Rothman & Still (1999) Med. Chem. Lett. 22, 509–512).

Surprisingly, there have been no published reports on the use of dabcyl in 5'-nuclease probes or other FRET probes that use long wavelength fluorophores. As mentioned above, dabcyl was used in the beacon-type probes but this is a different quenching mechanism wherein the dabcyl and fluorophore are in intimate contact (collisional quenching). Dabcyl was used in fluorogenic peptides as a quencher for the fluorophore EDANS (5-[(2-aminoethyl)amino] naphthalene-1-sulfonic acid) which emits at short (490 nm, blue) wavelength (Matayoshi et al. Science 247: 954–958 (1990)). EDANS also has a lower extinction coefficient than dabcyl so it is not surprising that fluorescent quenching was efficient. It was found for the first time in the present invention that dabcyl can be used to quench fluorescein in a FRET type mechanism.

In addition to the 5'-nuclease PCR assay, other formats have been developed that use the FRET mechanism. For example, single-stranded signal primers have been modified by linkage to two dyes to form a donor/acceptor dye pair in such a way that fluorescence of the first dye is quenched by the second dye. This signal primer contains a restriction site (U.S. Pat. No. 5,846,726) that allows the appropriate restriction enzyme to nick the primer when hybridized to a target. This cleavage separates the two dyes and a change in fluorescence is observed due to a decrease in quenching. Non-nucleotide linking reagents to couple oligonucleotides to ligands have also been described (U.S. Pat. No. 5,696, 251).

FRET systems also have applications in enzymology. Protease cleavable substrates have been developed where donor/acceptor dye pairs are designed into the substrate. Enzymatic cleavage of the substrate separates the donor/acceptor pair and a change in fluorescence is observed due to a decrease in quenching. Cleavable donor/acceptor substrates have been developed for chymotrypsin (Li et al. Bioconj. Chem., 10: 241–245 (1999)), aminopeptidase P (Hawthorne et al., Anal. Biochem., 253: 13–17 (1997)), stromelysin (Bickett et al., Ann. N. Y. Acad. Sci., 732: 351–355 (1994)) and leukotriene $D_4$ hydrolase (White et al., Anal. Biochem., 268: 245–251 (1999)). A chemosensor was described where binding of the ligand separates the donor/acceptor pair (Rothman et al. Biorg. Med. Chem. Lett., 9: 509–512 (1999)).

In U.S. Pat. No. 5,801,155 it was disclosed that oligonucleotides (ODNs) having a covalently attached minor groove binder (MGB) are more sequence specific for their complementary targets than unmodified oligonucleotides. In addition the MGB-ODNs show substantial increase in hybrid stability with complementary DNA target strands when compared to unmodified oligonucleotides, allowing hybridization with shorter oligonucleotides.

Reagents for fluorescent labeling of oligonucleotides are critical for efficient application of the FRET assays described above. Other applications such as DNA micro arrays also use fluorescently labeled DNA probes or primers, and there is a need for improved reagents which facilitate synthesis of fluorescent DNA. In general, phosphoramidite reagents and solid supports are widely used on ODN synthesis. However, in the state of the art there are not many commercially available phosphoramidite reagents for introducing fluorescent groups into ODNs.

Linker groups to attach different ligand groups to ODNs play an important role in the synthesis of oligonucleotide conjugates. A method for the synthesis of 3'-aminohexyl-tailed oligonucleotides (Petrie et al., Bioconj. Chem., 3: 85–87 (1992)), the use of a trifunctional trans-4-hydroxy-L-prolinol group (Reed et al., Bioconjug. Chem., 2: 217–225 (1991)), diglycolic acid (Pon et al., Nucl. Acids. Res., 25: 3629–3635 (1997)), 1,3-diol reagents (U.S. Pat. No. 5,942, 610 and U.S. Pat. No. 5,451,463) and the non-nucleotide trifunctional reagent (U.S. Pat. No. 5,696,251) have been reported.

Resorufin and coumarin derivatives have been extensively used as enzyme substrates to differentiate isozymes of cytochrome P450 (Haugland et al., Handbook of Fluorescent Probes and Research Chemicals, Six Edition, Eugene, Oreg. pp. 235–236. 1996.). Reactive resorufin analogs have been disclosed in U.S. Pat. No. 5,304,645. Activated esters of coumarin derivatives are known in the art (Hirshberg et al., Biochem., 37: 10391–5 (1998)). Coumarin-labeled dUTP incorporated in probes were used for in situ hybridizations (Wiegant et al., Cytogenet. Cell Genet., 63: 73–76 (1993)). Phosphoramidites to introduce labels into oligonucleotides have been described in U.S. Pat. Nos. 5,328,824 and 5,824, 796.

Many current hybridization applications, require more than one reporter molecule. In addition although reporter fluorophores are available to be used in reporter/quencher pairs, most suffer from having some undesirable characteristic, mixtures difficult to separate, positively charged, difficult to synthesize, unstable during oligonucleotide synthesis or having overlapping emission wavelengths with other desirable reporters. The present invention provides reagents for oligonucleotide probes that address these unfavorable characteristics and overcome some or all of the difficulties.

SUMMARY OF THE INVENTION

The present invention provides quencher molecules based on the 4-[4-nitrophenyl)diazinyl]phenylamine and/or the 4-[4-nitrophenyl)diazinyl]naphthylamine structure. The quencher molecules have improved UV spectral overlap not only with commonly used fluorescent reporter groups that emit short wavelength range (about 400 to 500 nm), but have extended the range to the mid (525 nm=green) to long (670 nm=red) wavelengths. The quencher chromophores of the present invention are non-fluorescent, easily incorporated into DNA synthesis reagents, stable during automated DNA synthesis and during storage and compatible with no adverse effects on hybridization properties. Moreover, improved signal to noise ratios are observed with the fluorescent reporter dyes over a more extended wavelength range. Thus the present invention offers considerable advantages over the use of dabcyl (Nazerenko et al, Nucl. Acids Res., 25: 2516–21 (1997)) as a quenching dye, as used in the prior art.

In accordance with one aspect of the present invention the quenchers based on the 4-[4-nitrophenyl)diazinyl] phenylamine (and/or the 4-[4-nitrophenyl)diazinyl] naphthylamine structure) are modified with linker structures that allow their easy incorporation into fluorogenic DNA probes during automated DNA synthesis. The invention includes synthesis of phosphoramidites derived from the novel quencher molecules for incorporation of the quencher moieties into oligonucleotides during automated synthesis, and also synthesis of reagents derived from the novel quencher molecules for post solid-phase support attachment to amino-tailed oligonucleotides. In a related aspect, the novel quencher molecules are introduced into oligonucleotides using pyrazolo-[5,4-d]pyrimidines and pyrimidines phosphoramidites containing the quenchers attached at the 3- and 5-positions, respectively.

In accordance with another aspect of the invention, three different fluorescent reagent types that are compatible with DNA synthesis are synthesized or selected and converted into phosphoramidite reagents suitable for incorporation onto ODNs. Specifically, violet fluorescent dyes based on the 10-phenyl-1,3,5,7,9,10-hexahydropyrimidino[5',4'-5,6] pyridino[2,3-d]pyrimidine-2,4,6,8-tetraone (PPT) structure, red fluorescent dyes based on 7-hydroxyphenoxazin-3-one (resorufin) and blue fluorescent dyes based on the structure of coumarin are incorporated into phosphoramidite reagents. These fluorescent dyes have excellent properties for multicolor fluorescent analysis in combination with other dyes (eg. fluorescein). These reagents are valuable for a variety of analytical methods that use either direct detection of fluorescence or FRET detection formats. In a related aspect of the invention the PPT-, coumarin- and resorufin-based fluorophores (fluorescent dyes) are converted into novel reagents suitable for "post-oligonucleotide-synthesis" covalent attachment at the 5'-end of ODNs. In another aspect, the new fluorescent dyes are incorporated into oligonucleotides using pyrazolo-[5,4-d]pyrimidines and pyrimidines phosphoramidites which contain the fluorophores attached at the 3- and 5-positions, respectively.

In accordance with still another aspect of the invention, ODNs covalently linked with the novel quencher structures of the invention, paired with a covalently attached fluorescent moieties, are prepared. The resulting FL-ODN-Q conjugate may also include a minor groove binder (MGB) that improves the binding and discrimination characteristics of the resulting FL-ODN-Q-MGB conjugate in diagnostic assays, particularly in the TaqMan PCR assay of single nucleotide polymorphism (and the like) where allele-specific discrimination not only requires probes with different fluorescent reporter molecules but efficient quenchers. The quenchers used in accordance with the invention in the FL-ODN-Q-MGB conjugates provide broad quenching wavelength range, and certain novel reporter labeling reagents in accordance with the invention have distinctive emission wavelengths for improved multicolor analysis.

In one application of the principles summarized above, fluorogenic probes are prepared using a universal "3'-hexanol" solid support (available in accordance with Gamper et al. Nucleic Acids Res., 21: 145–150 (1993) expressly incorporated herein by reference), where a quencher phosphoramidite of the invention is added at the first coupling step (3'-end) of the ODN sequence and a fluorophore (FL) was attached at the final coupling step, yielding 5'-FL-ODN-Q-hexanol conjugate probes.

As other applications of the invention, methods for synthesizing and attaching the novel quenchers to ODN-fluorophore conjugates with and without a 3'-minor groove binder (MGB) are disclosed. These methods utilize synthetic solid supports for automated oligonucleotide synthesis with cleavable linkers.

In another application, a fluorogenic oligonucleotide probe is prepared from a MGB modified solid support substantially in accordance with the procedure of Lukhtanov et al. Bioconjugate Chem., 7: 564–567 (1996), where a quencher-phosphoramidite of the invention is added at the first coupling step to the MGB, and a fluorophore (FL) is attached at the final coupling step to the ODN, to yield 5'-FL-ODN-Q-MGB conjugate probe.

Additional application of the methods and compositions of the present invention are in micro-arrays in nucleic acid-based diagnostic assays which recently have become important in many fields, such as the medical sciences, forensics, agriculture and water quality control. Other related application of the methods and compositions of the present invention are in procedures using arrays of oligonucleotides, such as the array-based analysis of gene expression (Eisen, Methods of Enzym., 303: 179–205 (1999)). In these procedures, an ordered array of oligonucleotides or DNAs that correspond to all, or a large fraction of the genes in many organism is used as a platform for hybridization. Microarray-based methods are used in assays to measure the relative representation of expressed RNA species. The quantitation of differences in abundance of each RNA species is achieved by directly comparing two samples by labeling them with spectrally distinct fluorescent dyes and mixing the two probes for simultaneous hybridization to one array.

To the extent the application of the compositions and methods of present invention relates to the detection of nucleic acids, it includes but is not limited to methods where FRET is involved, such as 5'-nuclease, universal energy transfer primers or beacon assays. These methods are usually directed to, but are not limited to the detection of PCR-generated nucleic acid sequences. Some of these methods involve simultaneous detection of more than one nucleic acid sequence in the same assay. Similarly, the invention relates to methods where FRET is involved in the detection of protein concentration or enzyme activity.

Still other application of the invention relates to the labeling with luminescent PPT-, coumarin- and resorufin-based dyes of nucleic acids, proteins and other materials including, drugs, toxins, cells, microbial materials, particles, glass or polymeric surfaces and the like, at a reactive group such as an amino, hydroxyl or sulfhydryl group. The present invention may be used in single- and two-step labeling processes. In the two-step labeling process, a primary component, such as an oligonucleotide is labeled with the reagent capable of introducing the novel fluorophore PPT-, coumarin- and resorufin-based dyes, by reaction with a reactive group of the ODN (such as an amine, hydroxyl, carboxyl, aldehyde or sulfhydryl group) and the label is used to probe for a secondary component, such as an oligonucleotide target.

BRIEF DESCRIPTION OF THE DRAWING FIGURES

DETAILED DESCRIPTION OF INVENTION

Quencher Reagents for Oligonucleotide Synthesis

Figure 1:
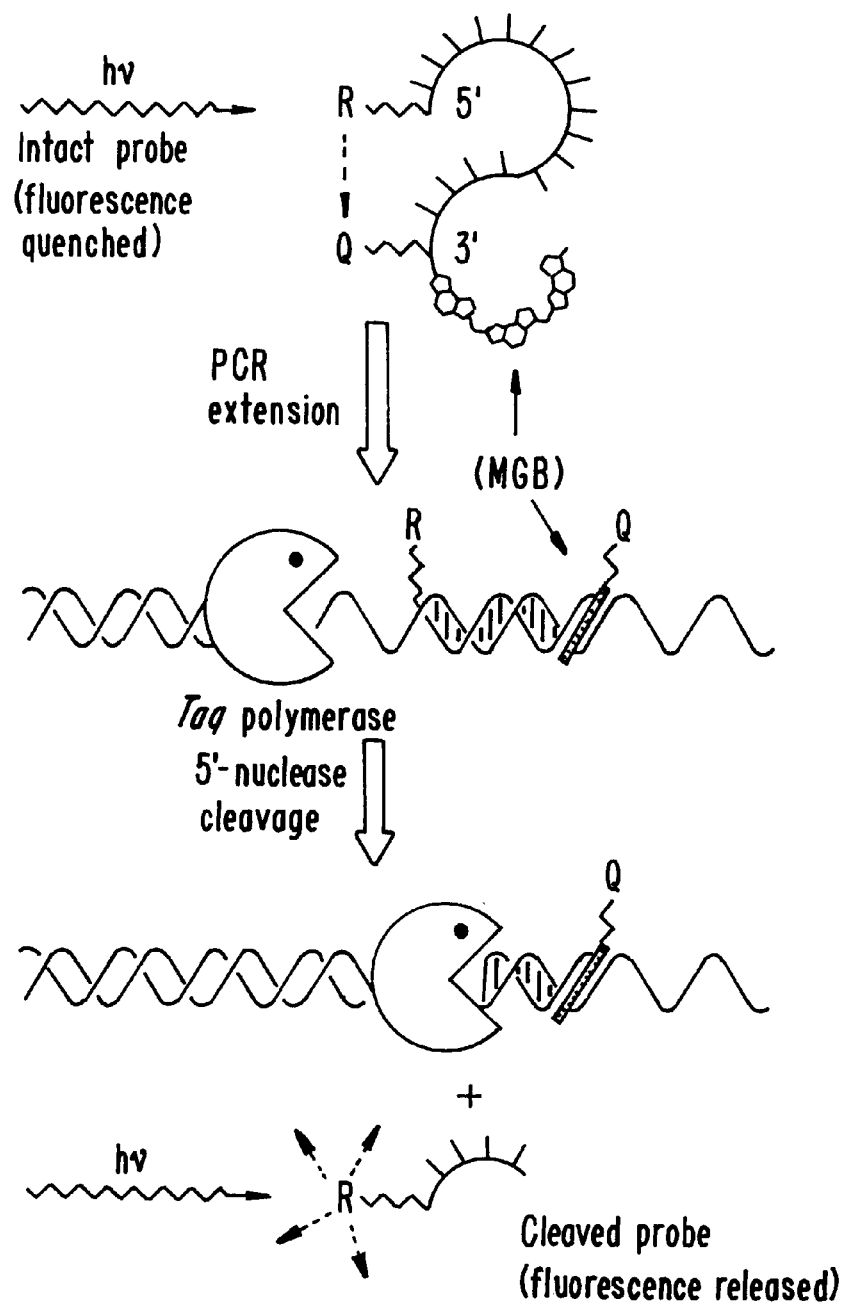
FIG. 1 is a schematic representation of real-time 5'-nuclease PCR assay.

Two types of reagents for introducing the substituted 4-(phenyldiazenyl)phenylamine quencher moieties into oligonucleotides using an automated DNA synthesizer are exemplified in the disclosure below. Here and in the reaction schemes the abbreviations MGB, FL, Q, CPG and ODN stand for "minor groove binder", "fluorescent or fluorophor", "quencher" "controlled pore glass" and "oligonucleotide" moieties or molecules, respectively, and in a manner which is apparent from context.

Dimethoxytrityl Protected Quencher Phosphoramidites

The first type of reagents disclosed herein are phosphoramidites that bear the quencher molecule (Q) as well as a dimethoxytrityl (DMTr) (methoxytrityl, trityl or the like acid labile blocking group) protected primary alcohol that provides an attachment point for the growing oligodeoxynucleotide (ODN) chain during subsequent oligonucleotide synthesis. Examples of these reagents are depicted in Formulas 1, 2, and 3, and in Reaction Schemes 1 and 2.

In Reaction Scheme 1 the starting compound is a substituted 4-(phenyldiazenyl)phenylamine 1 that has a primary hydroxyl group. Such starting material is commercially available or can be synthesized in accordance with methods known in the art, applying routine skill available to the practicing organic chemist. For example 4-nitrobenzendiazonium salt is reacted with 2-(2-chloroanilino)ethanol to yield 2-[2-chloro-4-(4-nitrophenylazo)anilino]ethanol in accordance with the teachings of U.S. Pat. No. 2,264,303. 2-[2-chloro-4-(4-nitrophenylazo)anilino]ethanol is within the scope of compound 1 as depicted in Reaction Scheme 1. The specification of U.S. Pat. No. 2,264,303 is expressly incorporated herein by reference.

Other examples of commercially available starting materials (or of their precursors) are: 2-(ethyl{4-[(4-nitrophenyl)diazenyl]phenyl}amino)ethan-1-ol and 2-(ethyl{4-[(2-methoxy-4-nitrophenyl)diazenyl]phenyl}amino)ethan-1-ol.

As is shown in Reaction Scheme 1, compound 1 is reacted with p-nitrophenylchloroformate to yield the carbonate 2. Reaction of 2 with substituted pyrrolidinediols yields a diol intermediate 3. The pyrrolidinediol is a trifunctional reagent that has an amino, a primary and a secondary hydroxyl group. An example of a pyrrolidinediol as well as examples of other trifunctional reagents having an amino, primary and a secondary hydroxyl group, are described in U.S. Pat. No. 5,512,667 the specification of which is incorporated herein by reference. The diol 3 is reacted first with dimethoxytrityl chloride (DMTrCl) to block the primary hydroxyl group of the trifunctional reagent and yield intermediate 4. The intermediate 4, still having a free secondary hydroxyl group in the trifunctional reagent, is then reacted with 2-cyanoethyl diisopropylchlorophosphoramidite to give the dimethoxytrityl protected phosphoramidite reagent 5. In the compounds shown in Reaction Scheme 1 the symbols are defined as follows. $R_0$, $R_1$, $R_2$, $R_3$ and $R_4$ are independently —H, halogen, —O(CH$_2$)$_n$CH$_3$, —(CH$_2$)$_n$CH$_3$ where n=0 to 5, —NO$_2$, —SO$_3$, —N[(CH$_2$)$_{n'}$CH$_3$]$_2$ where n'=0 to 5 or —CN; $R_5$=—H or —(CH$_2$)$_{n''}$CH$_3$ where n''=0 to 5; $R_6$=—(CH$_2$)$_{n*}$ where n*=1 to 5 and q=1 to 20. The dimethoxytrityl protected phosphoramidite reagent 5 is suitable for attachment to oligonucleotides in steps otherwise known in routine ODN synthesis.

REACTION SCHEME 1

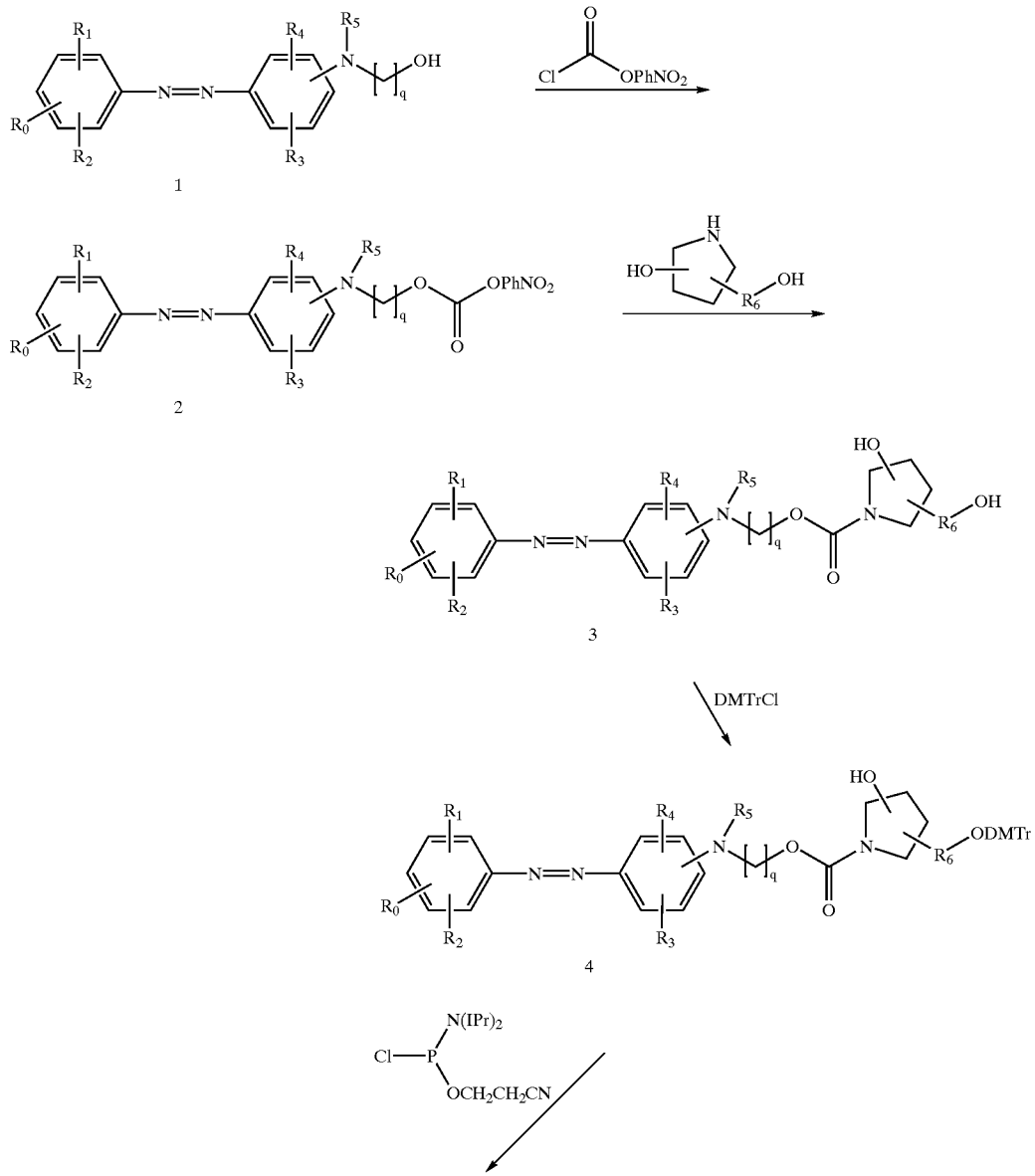

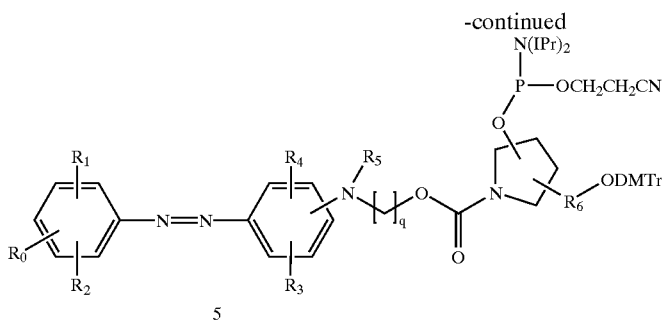

5

In other embodiments, using the reactions described in Reaction Scheme 1, (or only such modifications which are within the skill of the practicing organic chemist) starting with other trifunctional reagents having an amino and two hydroxyl groups, the phosphoramidites of Formula 1 and Formula 2 are synthesized, where q, $R_0$, $R_1$, $R_2$, $R_3$, $R_4$ and $R_5$, are defined as above; r and s independently are 1 to 20; X is —O— or —CH$_2$—; t and v independently are 1 to 20.

carboxyl group. Compound 6 (commercially available or made in accordance with the chemical literature within the skill of the practicing organic chemist) is reacted with pentafluorophenyl trifluoroacetate to make an active ester 7, which is thereafter reacted to couple the substituted 4-(phenyldiazenyl)phenylamine moiety to the ring nitrogen of a pyrrolidinediol moiety having a free primary and a free

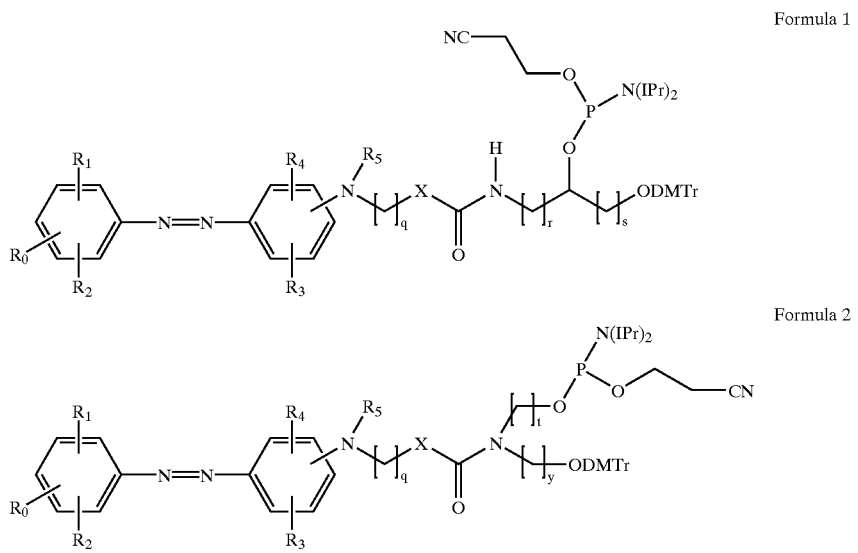

Reaction Scheme 2 discloses the synthesis of another exemplary phosphoramidite reagent 10 bearing the substituted 4-(phenyldiazenyl)phenylamine quencher moiety and including the trifunctional pyrrolidinediol moiety. In this synthetic scheme the starting material is a substituted 4-(phenyldiazenyl)phenylamine compound 6 that has a free secondary hydroxyl group, yielding compound 8. Treatment of 8 with DMTrCl followed by reaction with 2-cyanoethyl diisopropylchlorophosphoramidite gives the dimethoxytrityl protected phosphoramidite reagent 10. In Reaction Scheme 2 the symbols are defined the same as in Reaction Scheme 1.

REACTION SCHEME 2

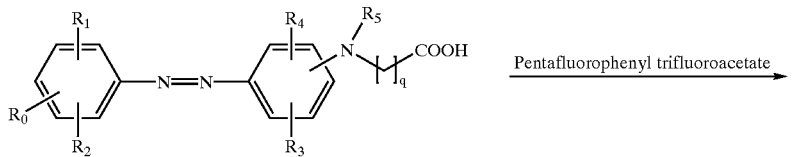

-continued

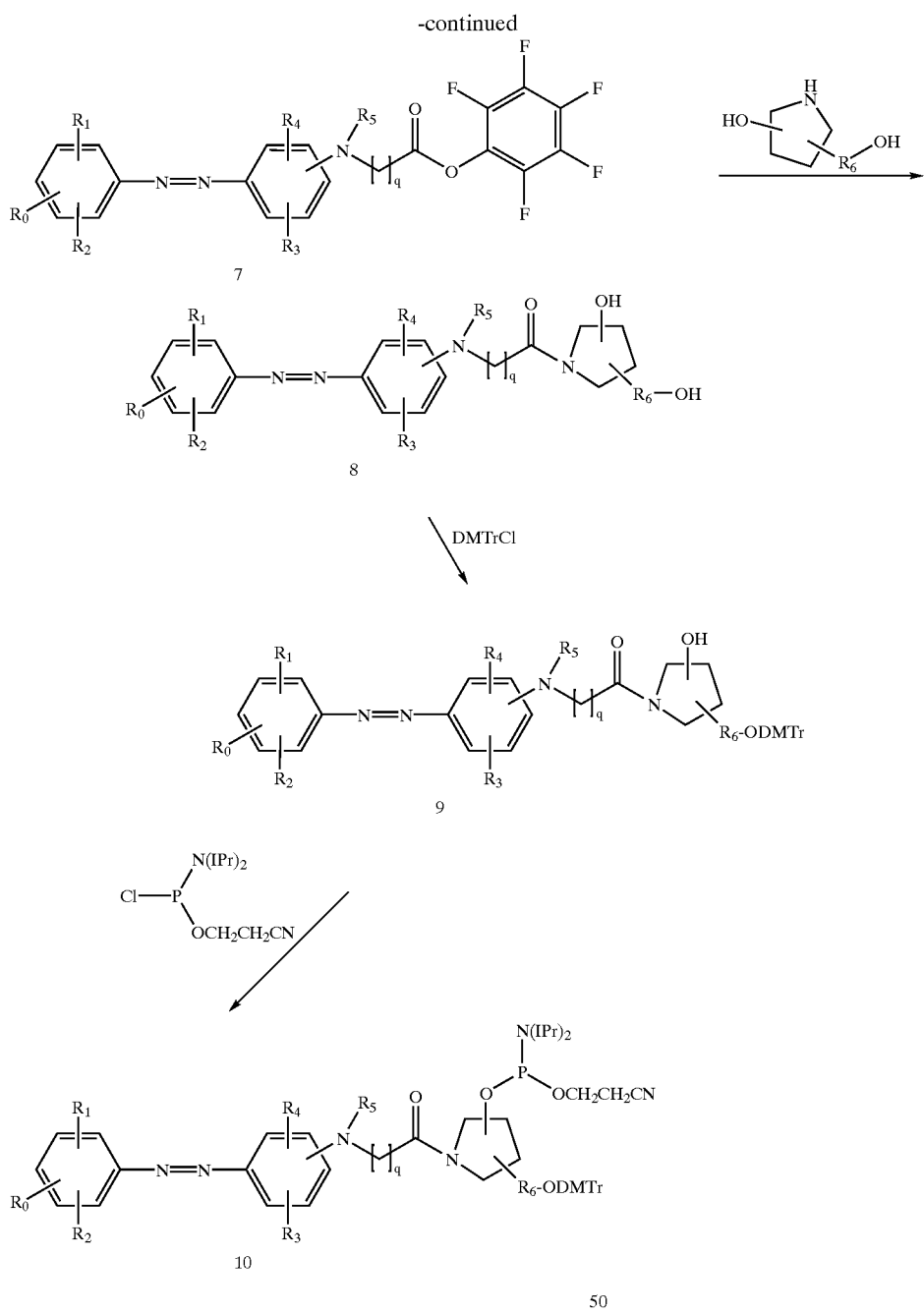

In still another example, using the reactions described in Reaction Scheme 2, starting with a substituted 4-(phenyldiazenyl)phenylamine (compound 6) and using a non-cyclic trifunctional reagent (having an amino and two hydroxyl functions) instead of the pyrrolidinediol shown in Scheme 2, the dimethoxytrityl protected phosphoramidite of Formula 3 is synthesized, where q, $R_0$, $R_1$, $R_2$, $R_3$, $R_4$, $R_5$, and $R_6$ are defined as above and t and v independently are 1 to 20.

Formula 3

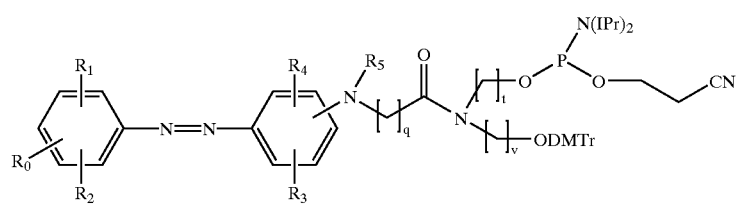

Quenchers Attached to Solid Support through (or similarly) Protected Linker, Suitable for ODN Synthesis A second class of compounds or reagents suitable for introducing the quencher molecules into ODNs constitute a composition that has a solid support of the type used for ODN synthesis (for example controlled pore glass (CPG)), and linker attaching the quencher to the solid support. The linker has a hydroxyl function that is protected, usually by a dimethoxytrityl group which is removed during the synthesis when the first nucleotide is attached to the linker. Generally speaking the same quencher/linker intermediates described above in Reaction Scheme 1 can also be used to prepare these reagents (CPG beads) having the exemplary structure 12, shown in Reaction Scheme 3. In accordance with this scheme, the secondary hydroxyl group of the intermediate 4 (shown in Scheme 1) is reacted with succinic anhydride, and thereafter pentafluorophenyl trifluoroacetate to provide the active ester 11. The active ester 11 is then reacted with the free amino group attached to the solid support (CPG bead) to provide the modified solid support 12. Whereas the exemplary modified solid support 12 includes the "trifunctional linker" derived from pyrrolidine diol, it will be readily understood by those skilled in art that analogous modified solid supports including other linkers and related structures, such as the linkers shown in Formulas 1, 2 and 3 can also be made substantially in accordance with Reaction Scheme 3, resulting in modified solid support compositions including the quencher moiety, such the ones shown in Formula 4 and Formula 5.

The modified solid support compositions including the quencher moiety of structure 12 and of Formula 4 and 5 are used for preparing 3'-quencher conjugates, allowing the introduction of a fluorophore at the 5'-end with the appropriate phosphoramidite, or post-synthetically with a fluorophore containing a reactive group. In Reaction Scheme 3 and in Formula 4 and Formula 5 the symbols are defined as above. It should be understood that other solid supports (such as polystyrene) and other cleavable linker systems (in addition to the succinate linker shown) can also be prepared in accordance with these generic teachings and therefore are also within the scope of the invention.

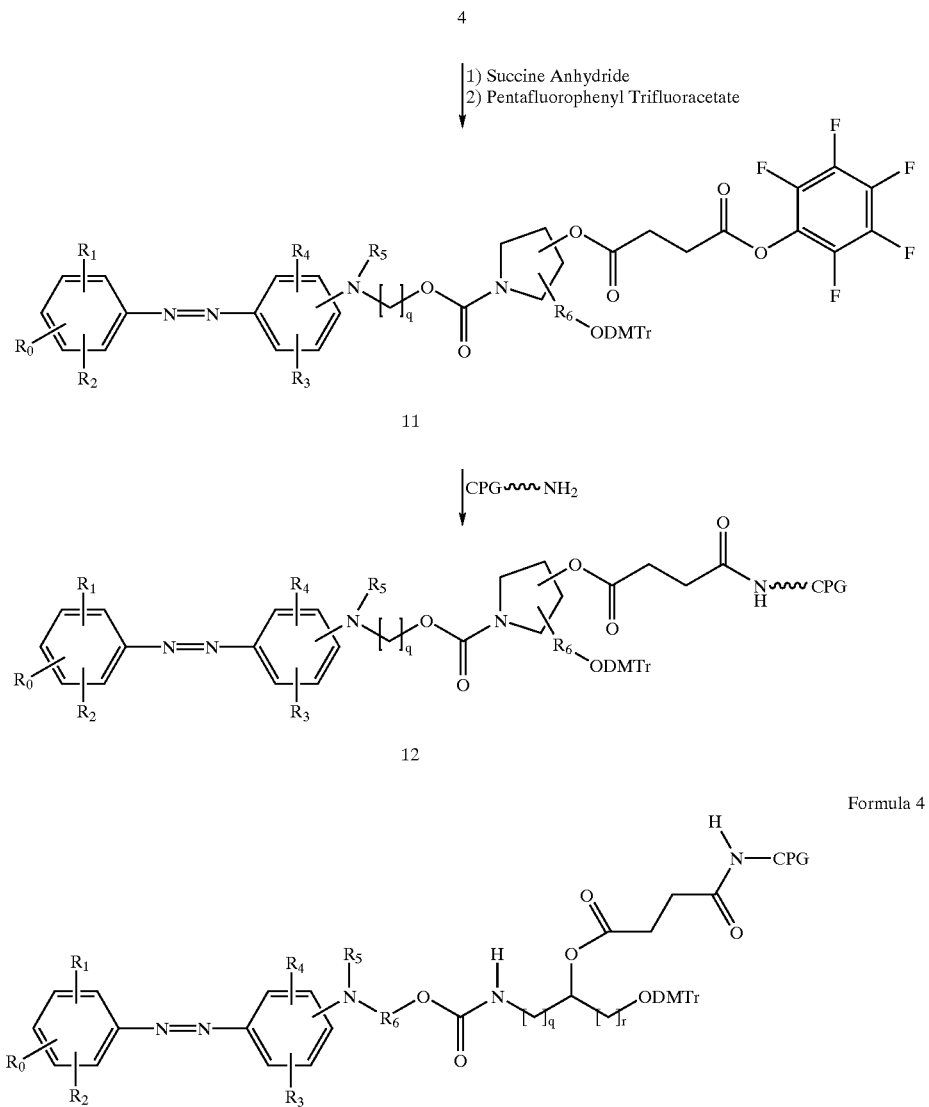

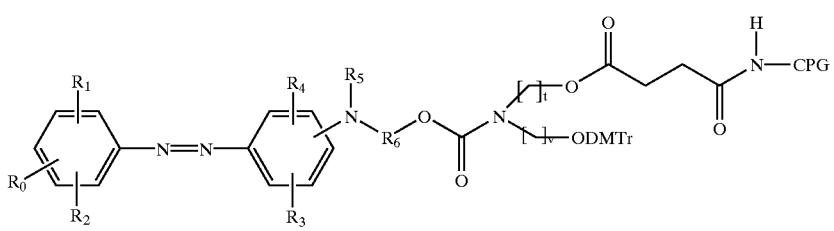

Formula 5

Minor Groove Binder Quencher Reagents for Oligonucleotide Synthesis

In one embodiment a minor groove binder (MGB) is attached to controlled pore glass (CPG) through a cleavable linker. A quencher moiety, based on the 4-(phenyldiazenyl) phenylamine structure, is attached through a linker molecule to the MGB. The linker molecule also contains a hydroxyl group blocked with DMTr (or like) blocking group. After removal of the DMTr group, an oligonucleotide is synthesized on an automated oligonucleotide synthesizer by stepwise attachment of nucleotide units to the hydroxyl group. A fluorophore is introduced at the 5'-end with the appropriate phosphoramidite, or post-synthetically with a fluorophore containing a reactive group, to yield an ODN having an attached fluorescent moiety (FL), quencher (Q) and MGB (FL-ODN-Q-MGB). In this connection it is noted that the synthesis of MGBs and their attachment to ODNs is well known (see for example U.S. Pat. No. 5,801,155, Ser. Nos. 09/539,097 and 9/141,764; all of which are expressly incorporated herein by reference.

In a preferred embodiment the MGB is 3-{[3-(pyrrolo[4,5-e]indolin-7-ylcarbonyl)pyrrolo[4,5-e]indolin-7-yl] carbonyl}pyrrolo[3,2-e]indoline-7-carboxylic acid ($DPI_3$). The synthesis of the covalently bound "aggregate" FL-ODN-Q-$DPI_3$ requires five phases, described below. The first phase, shown in Reaction Scheme 4, is the synthesis of an intermediate, 2-(4-nitrophenyl)ethyl 3-(pyrrolo[4,5-e]indoline-7-carbonyl)pyrrolo[4,5-e]indoline-7-carboxylate ($DPI_2$-NPC) 17. The second phase, shown in Reaction Scheme 5, is the synthesis of Q-DMTr-DPI-$CO_2$PFP 24 where a quencher is coupled through a linker to a pyrrolo[3,2-e]indoline-7-carboxylic acid unit (DPI). Here, and in the reaction schemes PFP stands for the pentafluorophenyl or pentafluorophenyloxy group, as the context requires. In the third phase, shown in Reaction Scheme 6, DMTr-Q-$DPI_3$-PFP 25a is synthesized from 17 and 24. In the fourth phase 25a is coupled to CPG to yield a DMTr-Q-$DPI_3$-CPG 29, and in the fifth phase 29 is used on an automated oligonucleotide synthesizer to stepwise attach nucleotide units and to provide, after removal from the CPG, the product FL-5'-ODN-3'-Q-$DPI_3$ 30.

The fourth and fifth phases of these synthetic process are shown in Reaction Scheme 7. Experimental conditions for this sequence (phases 1 through 5) are described below.

REACTION SCHEME 4

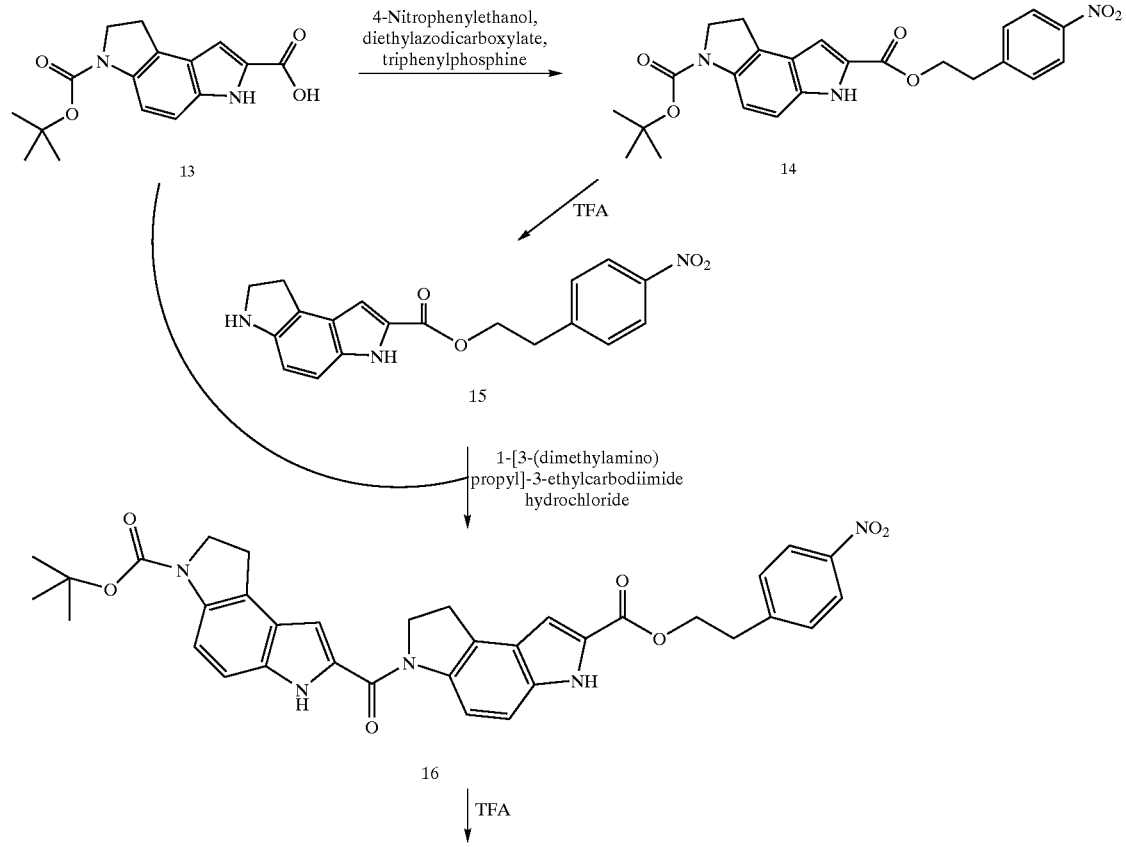

-continued
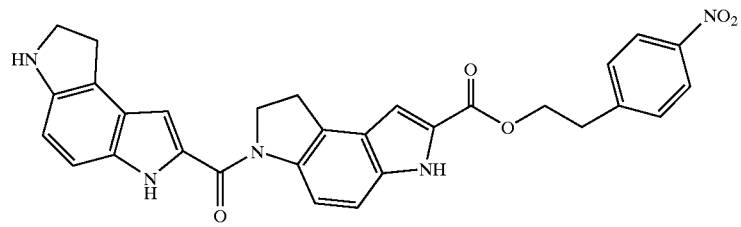
17
REACTION SCHEME 5
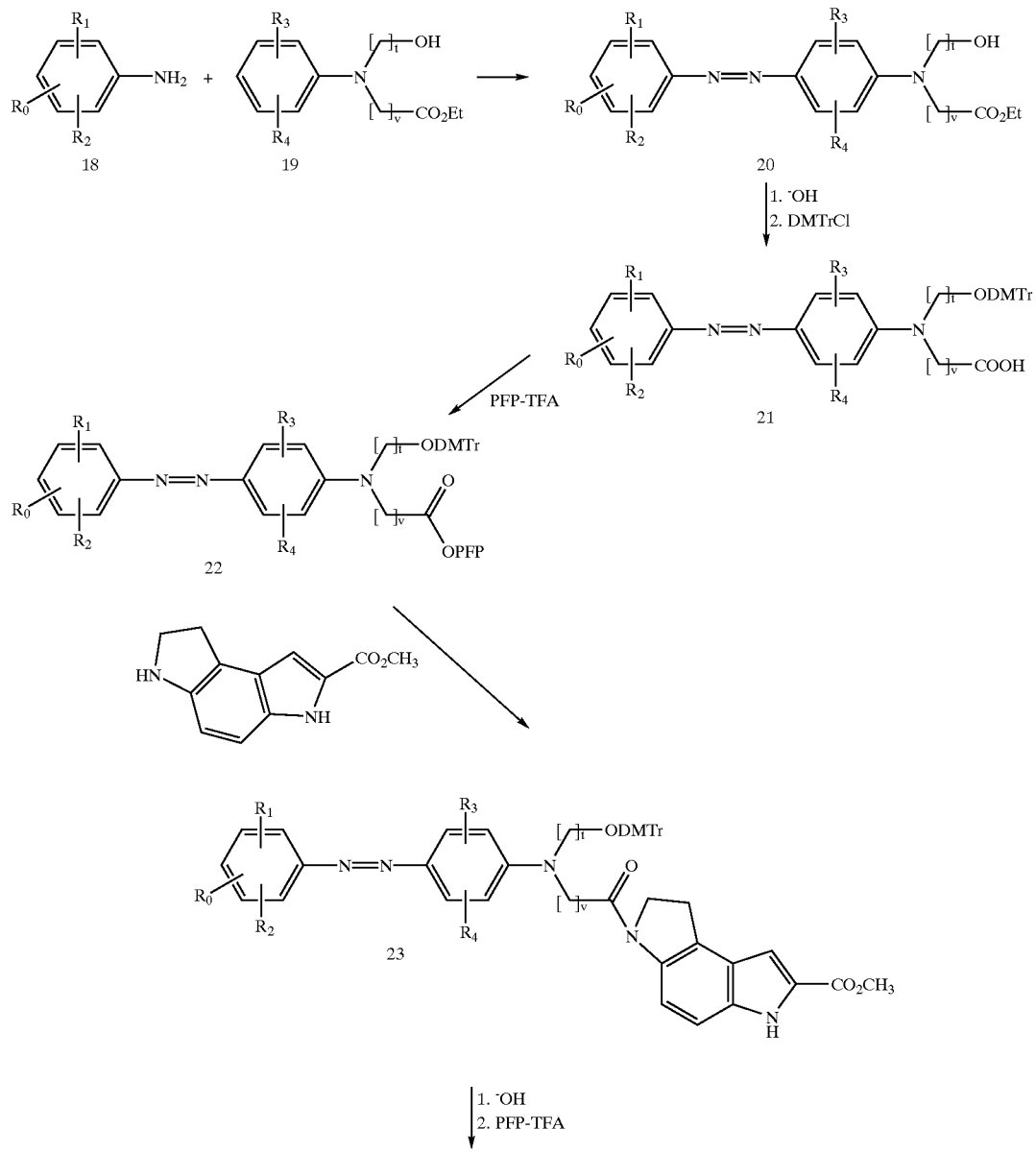

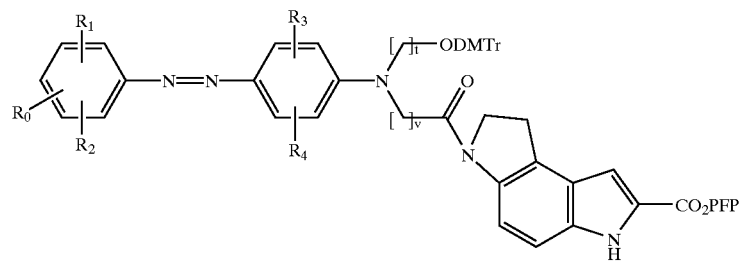
REACTION SCHEME 6
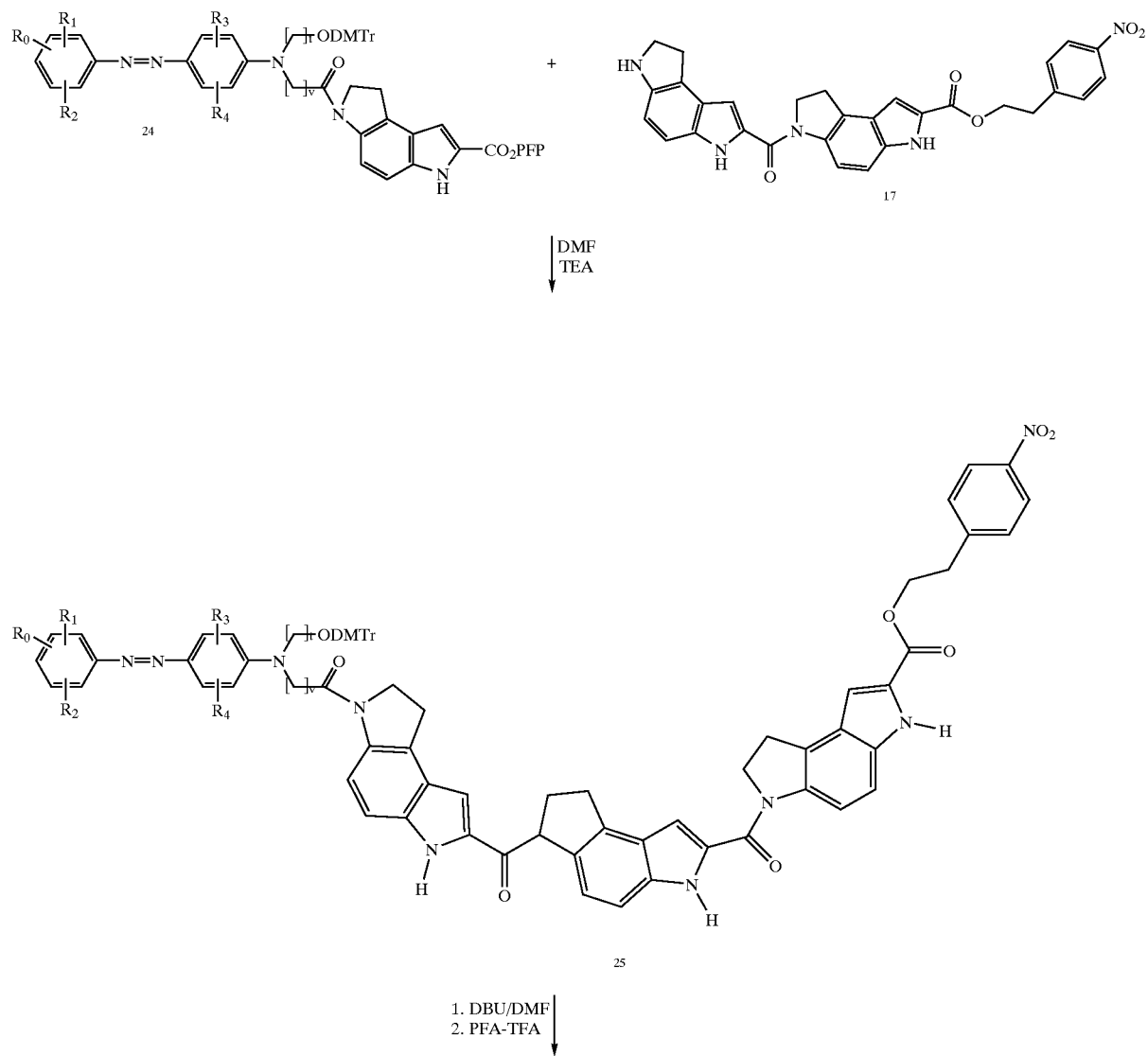

-continued
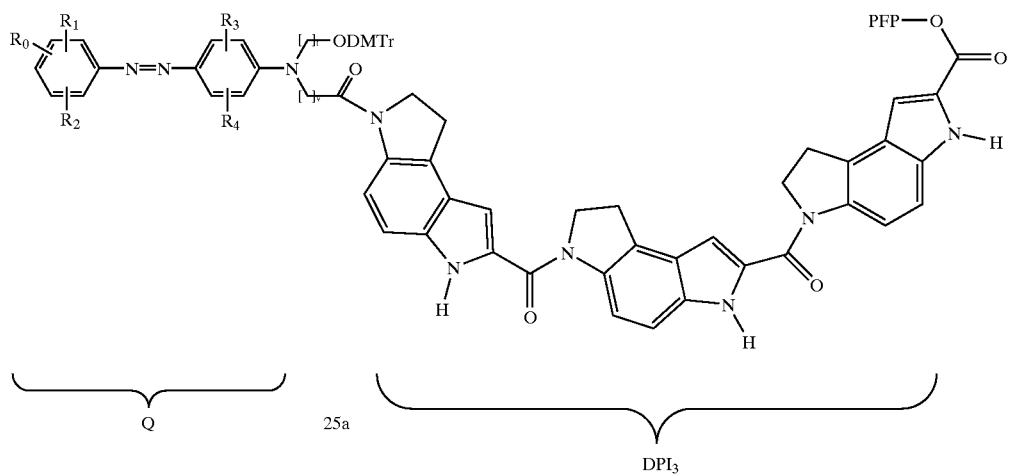
REACTION SCHEME 7
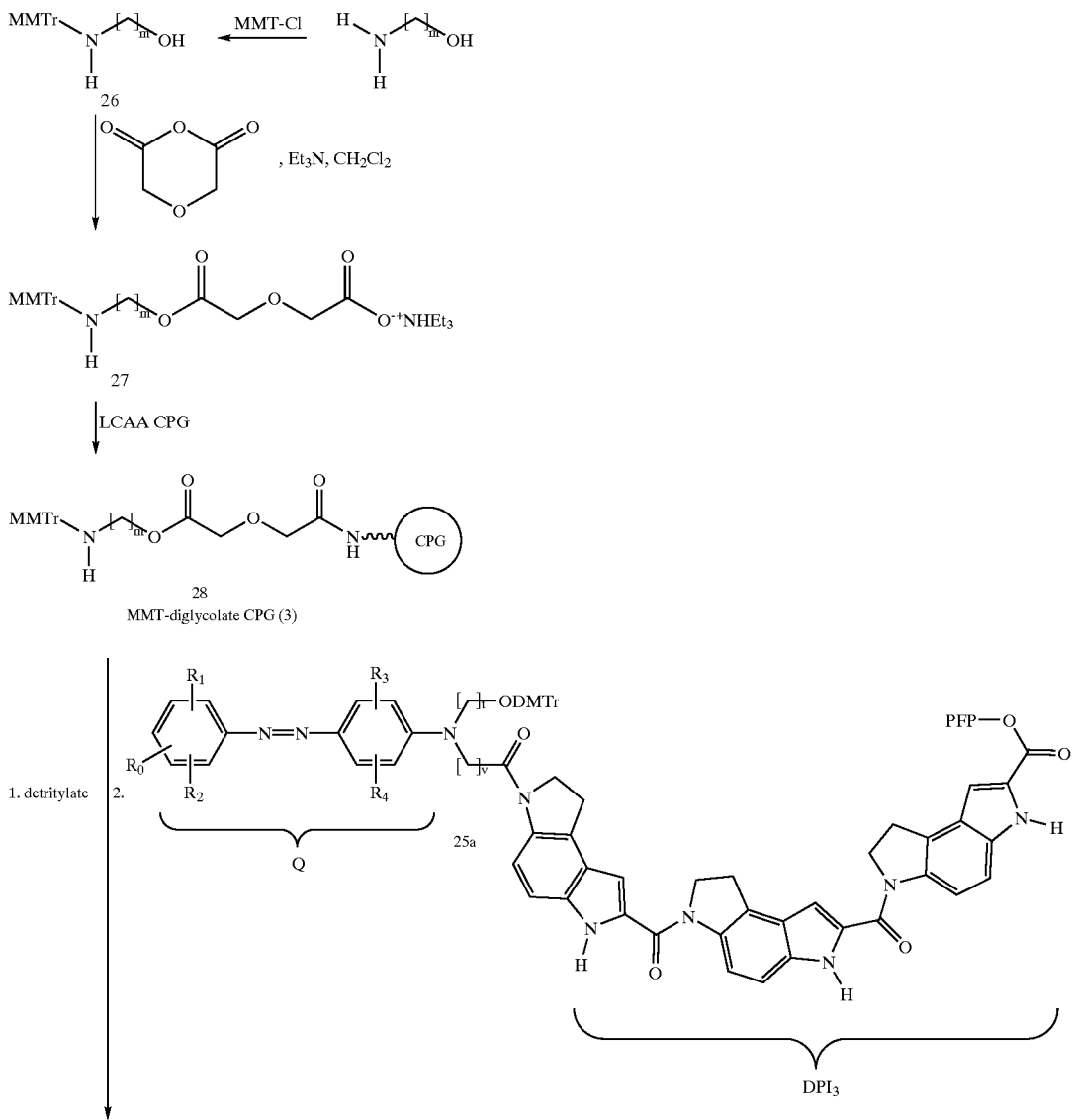

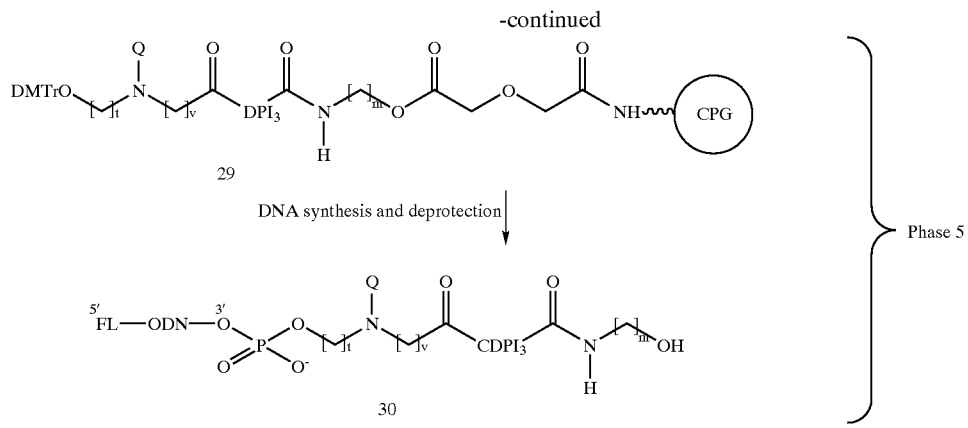

Describing these phases or reactions now in more detail, Q-DPI$_3$ moiety 25 (phase 3) is synthesized by the reaction of two intermediates, 17 and 24 as shown in Reaction Scheme 6. The first intermediate DPI$_2$-NPE 17 is made as shown in Scheme 4. DPI-tBoc 13 was reacted with p-nitrophenylethanol in the presence of diethylazodicarboxylate (DEAD) and triphenylphosphine to yield the di-ester 14. Compound 14 was first treated with trifluoroacetic acid (TFA) to yield 15, and then conjugated with 13 in the presence of 1-[3-(dimethylamino) propyl]-3-ethylcarbodiimide hydrochloride to give the 4-nitrophenyl ester of DPI$_2$ 16 in good yield. Reaction of 16 with TFA gives the p-nitrophenethyl ester of DPI$_2$ 17. The second intermediate DPI-Q 24 (phase 2) is synthesized as shown in Reaction Scheme 5. A substituted nitroaniline 18 (available commercially or in accordance with the chemical literature) is diazotized in the presence of nitrous acid and is coupled to a substituted aniline 19 (available commercially or in accordance with the chemical literature) to form the azo intermediate quencher molecule 20. Alkaline hydrolysis of the ethyl ester 20 followed by the treatment with DMTrCl gives the DMTr-Q 21, that is subsequently activated with pentafluorophenyl trifluoroacetate to yield 22. Reaction of 22 with DPI-methyl ester gives the Q-DMTr-DPI methyl-ester 23. Compound 23 is then treated with alkali to hydrolyze the methyl ester and then activated with PFP-TFA to yield Q-DMTr-DPI PFPester 24. In Reaction Scheme 5 the symbols $R_0$, $R_1$ through $R_4$, v and t are defined as above.

Referring now to Reaction Scheme 6, where the symbols are also defined as above, DMTr-Q-DPI$_3$-PFP 25a (third phase) is synthesized first by reacting the activated quencher 24 (DMTr-Q-DPI PFP) with DPI$_2$-NPC 17 to yield the p-nitrophenylethyl ester 25, which is converted to the active ester 25a, first by treatment with base such as 1,8-diazabicyclo[5.4.0]undec-7-ene (DBU) to remove the p-nitrophenylethyl moiety and then treatment with 2,3,4,5,6-pentafluorophenyl trifluoroacetate (PFP-TFA).

The synthesis of DMTr-Q-DPI$_3$-CPG 29 (phase four) is shown in Reaction Scheme 7. In this synthetic sequence the improved quencher molecule becomes attached through a cleavable diglycolate linker to controlled pore glass beads (CPG). Specifically, aminopropanol, or a homolog thereof, is reacted successively with monomethoxytrityl chloride (MMTr-Cl) and then with diglycolic anhydride to form MMT-blocked aminopropanol 26 (or homolog) and MMT-diglycolate 27, respectively. The symbol m is defined as an integer having the values 2 to 20. For the presently preferred aminopropanol m is 3. The remaining symbols in this scheme are defined as above. Reaction of 27 with long chain aminoalkyl CPG in the presence of activating agents (HOBT and HBTU), yields the MMT-diglycolate-CPG 28, that is converted after detritylation and reaction with 25a to DMTrO-Q-DPI$_3$-CPG 29.

In phase 5, still shown in Reaction Scheme 7 oligonucleotide synthesis is performed with the aid of an automated DNA synthesizer, and a fluorophore is attached at the 5'-end of the ODN, using either a fluorphorephosphoramidite or a fluorophore containing a reactive group, to yield the FL-ODN-Q-DPI$_3$ 30 conjugate.

The FL-ODN-Q-DPI$_3$ 30 conjugate can also be synthesized by an alternative synthetic route which is not specifically illustrated in the reaction schemes. In this alternative route DPI$_3$-methyl ester (obtained in accordance with Boger et al., J. Org. Chem., 52: 1521-(1987) incorporated herein by reference) is first reacted with compound 22 and then with alkali to give Q-DPI$_3$-methyl ester and Q-DPI$_3$-COOH, respectively. The latter compound is then activated with pentafluorophenyl trifluoroacetate, to yield 25a, which is then used in the reactions shown in Scheme 7, to yield 30.

FL-ODN-Q and FL-ODN-Q-MGB Probes

A general structure of a preferred embodiment of F1-ODN-Q-DPI$_3$ conjugates is shown in Formula 6 where:

FL is a fluorophore with emission wavelengths in the range of about 300 to about 800 nm and more preferably 400 to 700 nm; K is a linker containing between 1 and 30 atoms, which include any of C, O, N, S, P and H; [A-B]$_n$ symbolizes a DNA, RNA or PNA or any combination thereof, where A is the sugar phosphate backbone (including modified sugars and modified phosphates), B is the heterocyclic base, and n is the number of nucleotide units. B can independently be any of the purine- and pyrimidine-; pyrazolo[3,4-d]pyrimidine-, 7-substituted pyrazolo[3,4-d]pyrimidine-, 7-deazapurines, 7-substiuted 7-deazapurines, modified purine- and pyrimidine-bases, and the oligonucleotide or nucleic acid can include any combinations of these bases. W is a linker of the length of 0 to approximately 30 atoms, selected from the group consisting of C, O, N, S, P and H, furthermore W is a substituted branched aliphatic chain, or a substituted ring structure or a combined substituted aliphatic and ring structure; $R_0$, $R_1$, $R_2$, $R_3$ and $R_4$ are as described previously and m=1 to 20.

Formula 6

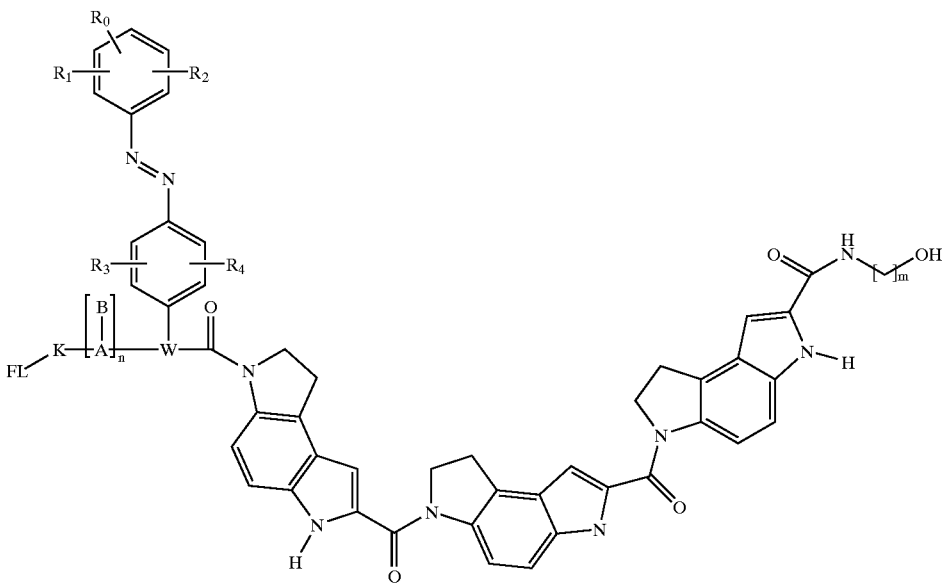

Syntheses of PNA and PNA/DNA chimeras are known in the art and can generally speaking be performed in accordance with the publications Uhlmann et al., Angew. Chem. Inter. Ed., 37:2796–2823 (1998); Mayfield et al., Anal. Biochem., 401–404 (1998) which are incorporated herein by reference.

A still more preferred embodiment within the scope of Formula 6 is one where W is —(CH$_2$)$_3$N(-)—(CH$_2$)$_3$—; R$_0$=NO$_2$; R$_1$=—Cl; R$_2$=R$_3$=R$_4$=H; K is a 6 carbon linker and m=3.

Conjugate probes of the present invention containing a fluorescent reporter-quencher pair are, generally speaking, used in conjunction with the amplification of target polynucleotides, frequently in methods utilizing PCR, as described for example by Holland et al. Proc. Acad. Sci., 88: 7276–7280(1991) and Wittwer et al., Biotechniques, 22: 176–181 (1997) which are incorporated herein by reference. The binding site of the conjugate probe is located between the PCR primers used to amplify the target polynucleotide.

Use of the conjugate oligonucleotide probes according to the present invention for detection of target oligonucleotide sequences provides several advantages over prior-art reporter quencher groups and combinations. For example, the quenchers including the 4-[4-nitrophenyl)diazinyl] phenylamine structure in accordance with the present invention gave larger signal to noise ratios (S/N) in probes with either FAM or TAMRA serving as reporters than dabcyl as a quencher. Furthermore, the quenchers in accordance with the invention show a broader absorbance range than dabcyl, allowing efficient quenching of a broad range of fluorophores. In addition, in MGB-oligonucleotide conjugates have improved hybridization characteristics, an improved quencher showed about 30-fold increase in S/N ratio with TAMRA compared to a standard probe (no DPI$_3$) with dabcyl. Reagents of the present invention allow the introduction of the quencher during automated oligonucleotide synthesis. (Dabcyl phosphoramidite is commercially available; (Glen Research, Sterling, Va.))

It should be understood that, generally speaking, for the purpose of this invention, an oligonucleotide comprises a plurality of nucleotide units, a 3' end and a 5'end. The oligonucleotide may contain one or more modified bases other than the normal purine and pyrimidine bases, as well as modified internucleotide linkages capable of specifically binding target polynucleotide through Watson-Crick base pairing, or the like. In addition, oligonucleotides may include peptide oligonucleotides (PNAs) or PNA/DNA chimeras, the synthesis of which is known and can be performed for example in accordance with the publications Uhlmann et al., Angew. Chem. Inter. Ed., 37:2796–2823 (1998) and Mayfield et al., Anal. Biochem., 401–404 (1998); all of which are expressly incorporated herein by reference.

Generally, the oligonucleotide probes of the invention will have a sufficient number of phophodiester linkages adjacent to the 5' end to allow 5'→3' exonuclease activity to allow efficient cleavage between the quencher and fluorophore molecules in the probe. An adequate number in this regards is approximately between 1 and 100.

Fluorophore Reagents
Coumarin Phosphoramidite Reagents

Fluorescent dyes which have emission wavelengths shorter than the green fluorescent dye FAM also have utility in DNA probe based assays. However in the prior art these probes have been less popular since excitation with laser light sources is less feasible than with longer wavelengths. To the best knowledge of the present inventors, to date, there have been no reports of DNA synthesis reagents that contain blue fluorescent dyes. An example of such a phosphoramidite reagent containing a preferred coumarin fluorophore and which is suitable for DNA synthesis, is shown in Reaction Scheme 8, as compound 34. In the phosphoramidite reagent 34, R$_8$ and R$_9$ independently are H, halogen, —NO$_2$, —SO$_3$, —C(=O)NH$_2$, or —CN; —OR$_{nn}$, —SR$_{nn}$, —OR$_{nn}$, —NHR$_{nn}$, —N[R$_{nn}$]$_2$ where R$_{nn}$ is independently H, a blocking group compatible with oligomer synthesis and which can be removed under acid or alkaline conditions; or a group that contains between 1 and 10 carbon atoms, j and k independently are 1 to 10. As can be seen the reagent 34includes a covalently linked coumarin chromophore which emits light at 458 nm. DNA probes containing this coumarin chromophore were prepared and gave the desired fluorescent emission properties.

REACTION SCHEME 8

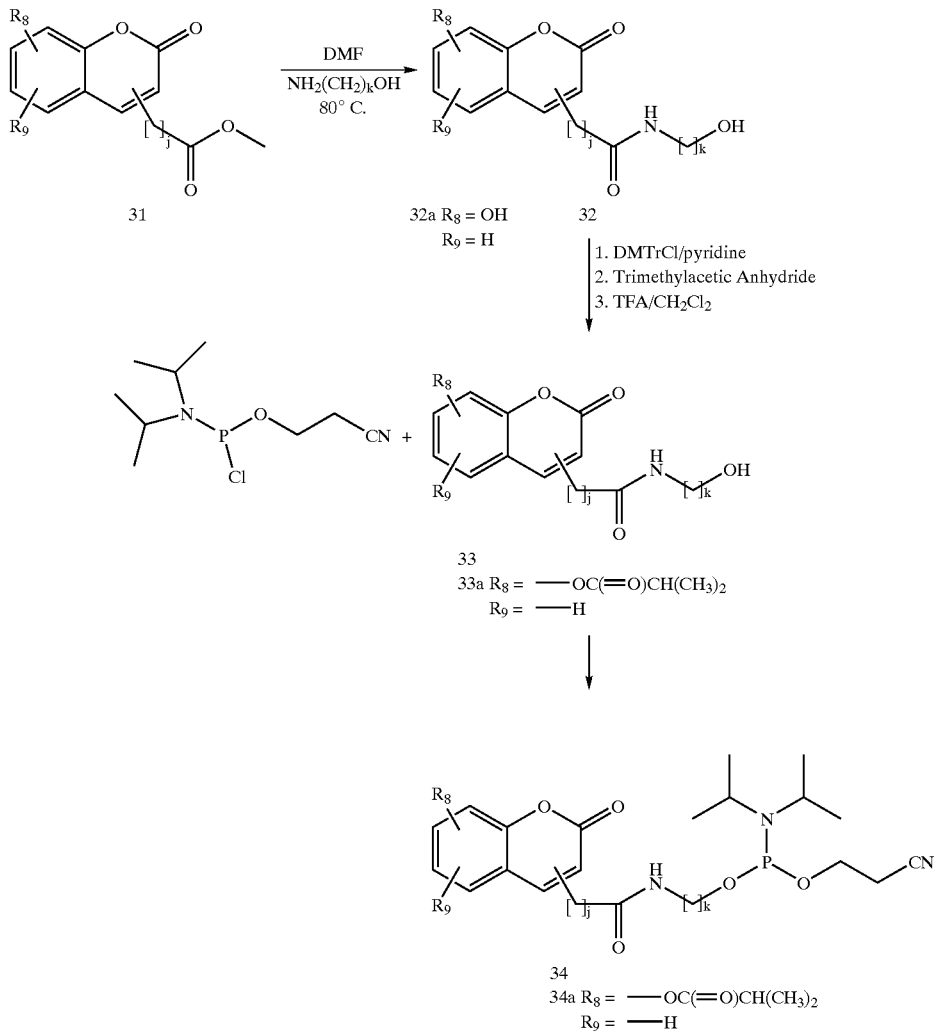

Referring now to Scheme 8 in general terms and also in an example that provides the specific phosphoramidite reagent 34a, a hydroxyl substituted (2-oxo-2H-chromen-4-yl)-alkylcarboxyl methyl ester (31) is obtained according to the publication Baker et al. (J. Chem. Soc.; 170, 173 (1950)) incorporated herein by reference. Compound 31 is converted to the alkanol derivative 32 (specifically to 32a where $R_8$ is —OH and R is —H) by reaction with an aminoalkanol at 80° C. Reaction of 32 first with DMTrCl and then with trimethylacetic anhydride followed by the removal of the DMTr blocking group gives a pivaloate derivative 33, in the specific example 33a where $R_8$ is —OC=O)CH(CH$_3$)$_2$ and $R_9$ is —H. Reaction of 33 with 2-cyanoethyl diisopropyl-chlorophosphoramidite gives reagent 34 (specifically 34a where $R_8$ is —OC(=O)CH(CH$_3$)$_2$, $R_9$ is —H). The reagent 34 is used for incorporating the coumarin fluorophore into the 5'-terminus of DNA probes. It is noteworthy that removal of the protecting groups during automated oligonucleotides synthesis proceeded well, resulting in high yields. The symbols j and k in Scheme 8 are defined as 0 to 20 and 1 to 20, respectively.

Resorufin Phosphoramidite

Another new class of DNA synthesis reagents are based on the 7-hydroxy-3H-phenoxazin-3-one chromophore present in the parent compound (resorufin) and have emission wavelength (595 nm) that is easily distinguished from FAM emission. In accordance with the invention the chromophore is synthesized in such a way as to incorporate a linker structure for further functionalization to the desired phosphoramidite reagents. The preparation of preferred examples of these reagents 37 suitable for DNA synthesis, is shown in Reaction Scheme 9. Generally speaking in reagent 37 $R_{10}$ and $R_{11}$ independently are H, —OR$_{12}$, —NHR$_{13}$, halogen, —O(CH$_2$)$_n$CH$_3$, —(CH$_2$)$_n$CH$_3$, —NO$_2$, —SO$_3$, —C(=O)NH$_2$, —N[(CH$_2$)$_n$CH$_3$]$_2$, O-alkyl or O-alkanoyl where the alkyl or alkanoyl group has 1 to 10 carbons, or —CN where n=0 to 5; h=1 to 20; and $R_{12}$ and $R_{13}$ are blocking groups compatible with ODN synthesis. $R_{14}$ in the scheme is H or DMTr.

REACTION SCHEME 9

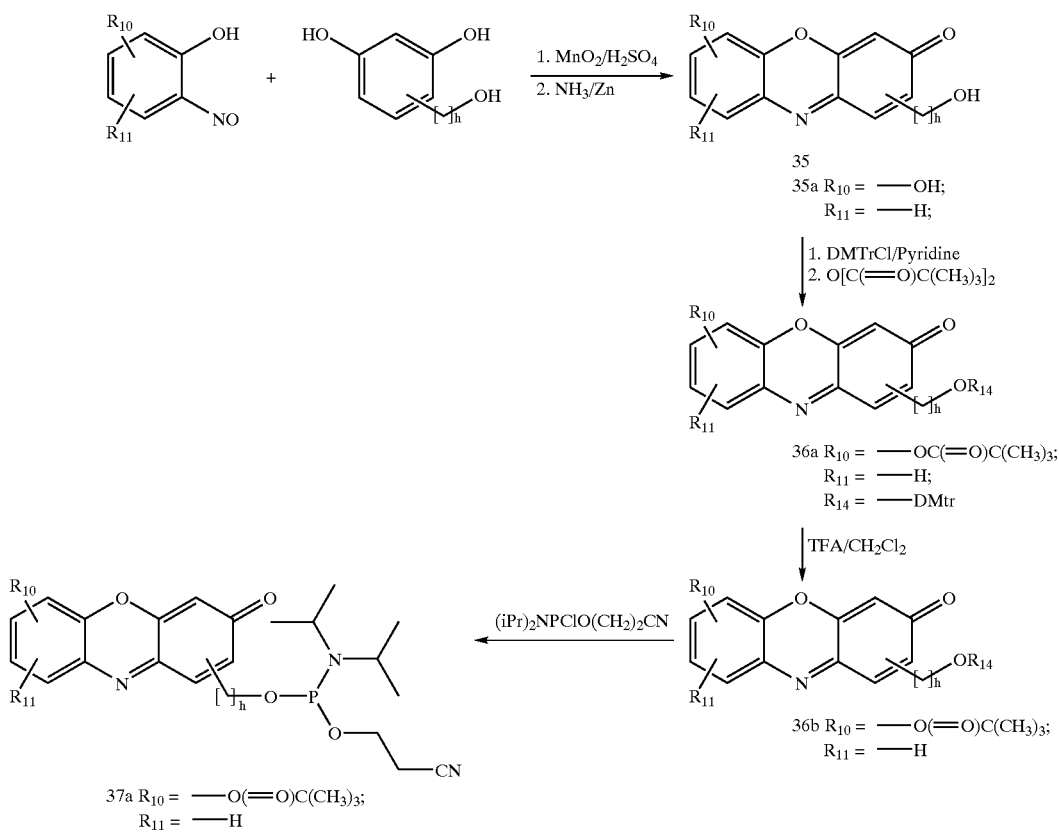

As is shown in the example of Scheme 9 in general terms and also for a specific example, reaction of nitrosorecorcinol derivative (commercially available or synthesized in accordance with the state-of-the-art) and of 4-(3-hydroxypropyl)benzene-1,3-diol (obtained in accordance with Forchiassin et al. J. Heterocyc. Chem. 20, 1983, 493–494.) and $MnO_2$ yielded a resazurin derivative contaminated with some resorufin derivative. This mixture was treated with $NH_4OH$ and Zn dust to yield resorufin derivative 35 (specifically 35a where $R_{10}$ is OH, and $R_{11}$ is H) contaminated with 2,3,4-trihydro-2H-pyrano[3,2-b]phenoxazin-9-one as major impurity. The latter mixture was treated with DMTrCl and pyridine, and then with trimethylacetic acid anhydride. The product 36 was then subjected to purification by chromatography on silica gel to give the DMTr-protected derivative of 36a (where $R_{10}$ is $—OC(=O)C(CH_3)_3$, $R_{11}$ is H and $R_{14}$ is DMTr). The pure DMTr-derivative was treated with $TFA/CH_2Cl_2$ to yield a single product 36b after silica gel chromatography. Treatment of 36 (where $R_{10}$ is $—OC(=O)C(CH_3)_3$, $R_{11}$ and $R_{14}$ are H) with 2-cyanoethyl diisopropylchlorophosphoramidite gave the desired phosphoramidite reagent 37 (specifically 37a) that is utilized to introduce the fluorophore into a desired ODN.

REACTION SCHEME 10

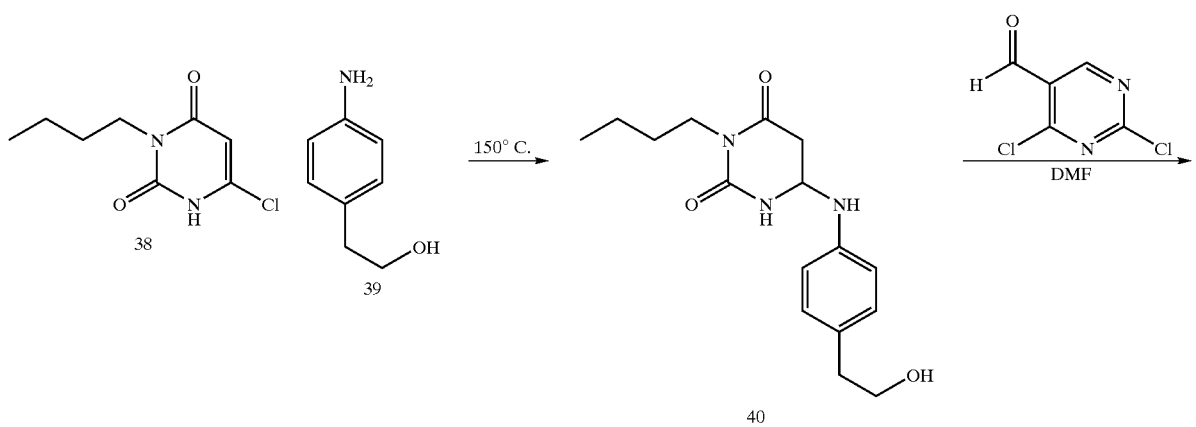

-continued

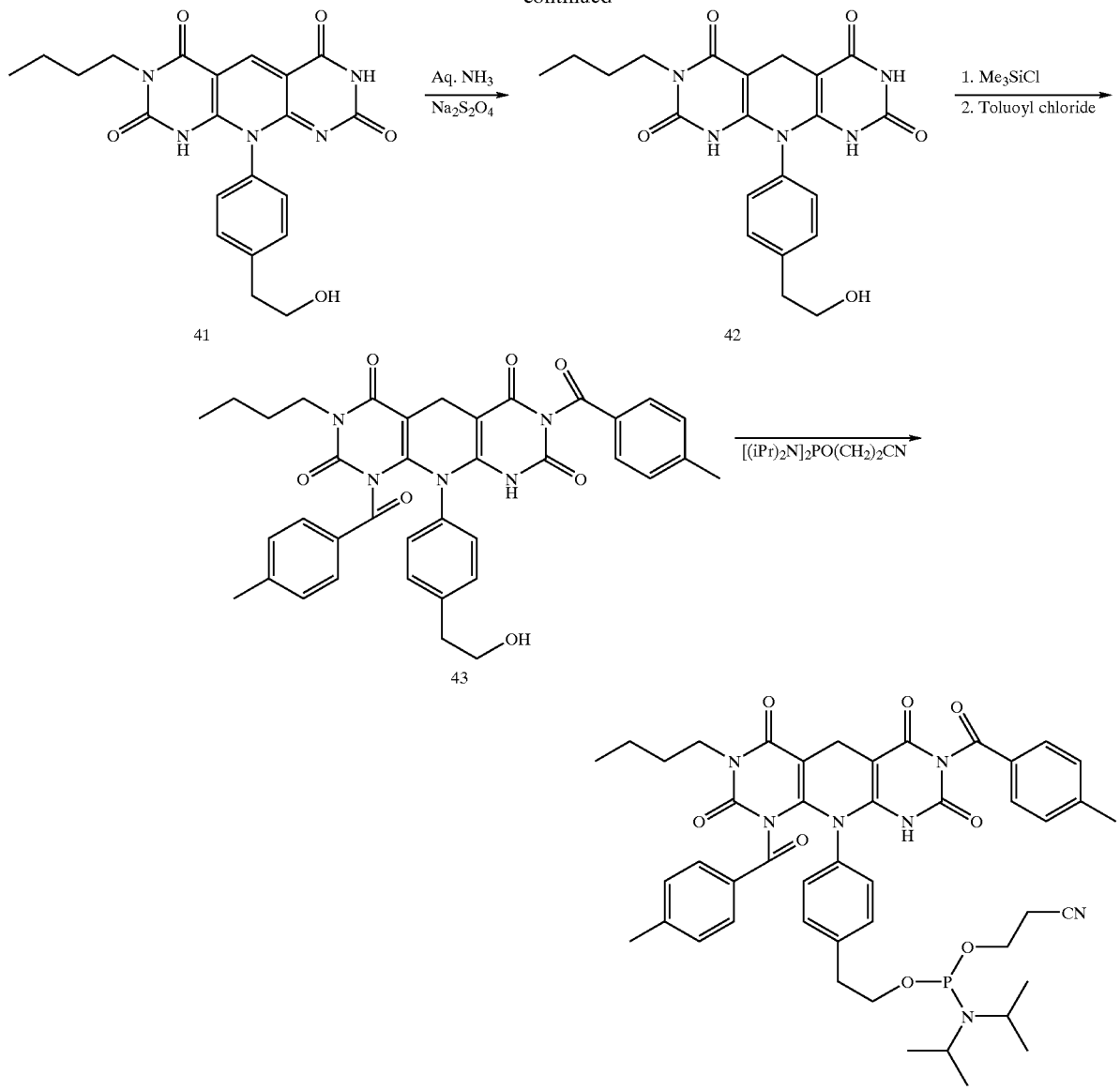

PPT Phosphoramidite

The synthesis of a phosphoramidite reagent incorporating a purple fluorescent dye PPT 44 having excitation and emmision wavelengths of 384 and 400 nm, respectively is shown in Reaction Scheme 10 and in Example X. In accordance with this scheme 6-chloro-3-n-butyluracil 38 and 2-(4-aminophenyl)ethanol 39 are reacted to yield the phenyl substituted uracil derivative 40. The compounds 38 and 39 can be obtained in accordance with the state-of-the-art and the chemical literature. Reaction of 40 with 5-formyl-4,6-dichloro pyrimidine in DMF at room temperature affords the tricyclic heterocycle 41. Reduction of 41 in $NH_3/Na_2S_2O_4$ yields 42 which is thereafter blocked as the toluoyl-derivative 43. In the final step 43 is reacted with 2-cyanoethyl diisopropylchlorophosphoramidite to yield the reagent PPT cyanoethyl phoporamidite 44 that is used to introduce the PPT fluorophore into an ODN.

In still further embodiments, the fluorophores coumarin, resorufin and PPT substituted with an alkylcarboxyl group serve as starting materials for the synthesis of the corresponding phosphoramidite reagents. The fluorophores coumarin, resorufin and PPT substituted with an alkylcar- boxyl group are either commercially available or can be synthesized in accordance with the state-of-the-art. These compounds are activated on the alkylcarboxyl group as the pentafluorophenyl esters. The activated esters are used to attach these dyes to amine modified oligonucleotides.

Similarly, in still other embodiments, dUTP-labeled quenchers or fluorophores are obtained for example in accordance with the teachings of U.S. Pat. No. 5,328,824). Furthermore, the phosphoramidite of 7-labeled pyrazolo[3,4-d]pyrimide-labeled quenchers or fluorophores are synthesized according to the teaching of U.S. Pat. No. 5,824,796 (incorporated herein by reference) and can be used for labeling of oligonucleotides. PPG Red Dye-based and Other Phosphoramidite Reagents for Oligonucleotide Synthesis.

In another embodiment the red dye 13 quencher is attached to the 3-position of pyrazolo[5,4-d]pyrimidines (PP) or the 5-position of a pyrimidine. Referring now to Scheme 11 itself, the starting material is 5-(4-amino-3-iodopyrazolo[5,4-d]pyrimidinyl)-2-(hydroxymethyl) oxolan-3-ol 45 which is available in accordance with the publication Seela et al. J. Chem. Soc., Perkin. Trans., 1 (1999, 479–488) incorporated herein by reference. Compound 45 is first reacted with N-propynyl-2,2,2- trifluoroacetate (or a homolog thereof where in the scheme n is 1 to 10) and then with Pd(PPh$_3$)$_4$—CuI to give the alkyne derivative 46. Pd/H$_2$ reduction of 46 followed by ammonium hydroxide treatment gives the aminoalkyl derivative 47 (PPA'). Reaction of PPA' with compound 2 (available as disclosed in connection with Reaction Scheme 1) yielded substituted PPA'-Red 13 48. Reaction of 48 with (1,1-dimethoxyethyl)dimethylamine blocks the amino group of the pyrazolo[5,4-d]pyrimidine to yield 49. 49 is first reacted with DMTrCl and then with 2-cyanoethyl diisopropylchlorophosphoramidite to give the DMTrCl blocked PPA'-Red 13 phosphoramidite 50.

REACTION SCHEME 11

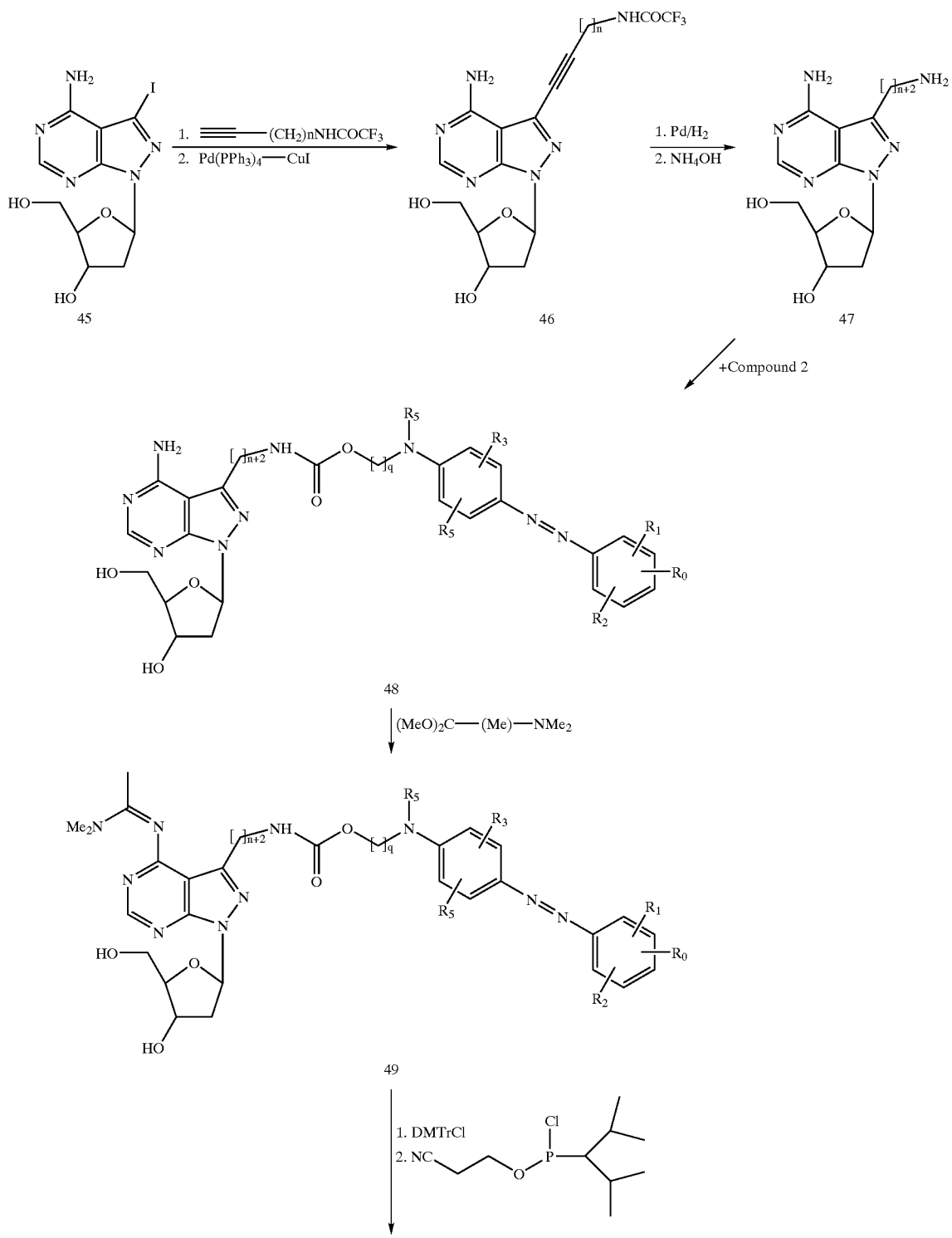

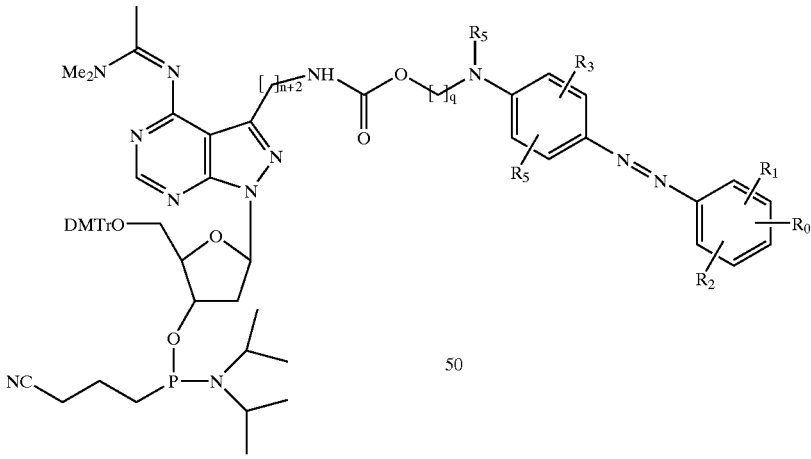

In still other embodiments starting with the deoxyriboside of 6-amino-5-hydroxy-3-iodo-pyrazolo[5,4-d]pyrimidin-4-one (3-Iodo-PPG) the phosphoramidite reagent containing the Red 13 dye covalently linked to the 3-Iodo-PPG moiety is synthesized with reactions analogous to those shown in Reaction Scheme 11. Similarly starting with 5-aminopropyldeoxyuridine the phosphoramidite reagent containing the Red 13 dye covalently linked to 5-aminopropyl-deoxyuridine is synthesized.

It will be clear to those skilled in the art in light of the foregoing disclosure that the pyrazolopyrimidine-Red-13- or uridine-Red 13-based phosphoramidites within the scope of this invention may contain various linkers between the pyrazolopyrimidine and uracil bases and the Red 13 quenchers, to the fall extent such linkers are available in accordance with the state of the art and this disclosure.

Examples of Applications and Uses of the Invention

The methods and compositions of the present invention can be used with a variety of techniques, both currently in use and to be developed, in which hybridization of an oligonucleotide to another nucleic acid is involved. These include, but are not limited to, techniques in which hybridization of an oligonucleotide to a target nucleic acid is the endpoint; techniques in which hybridization of one or more oligonucleotides to a target nucleic acid precedes one or more polymerase-mediated elongation steps which use the oligonucleotide as a primer and the target nucleic acid as a template; techniques in which hybridization of an oligonucleotide to a target nucleic acid is used to block extension of another primer; techniques in which hybridization of an oligonucleotide to a target nucleic acid is followed by hydrolysis of the oligonucleotide to release an attached label; and techniques in which two or more oligonucleotides are hybridized to a target nucleic acid and interactions between the multiple oligonucleotides are measured. The conditions for hybridization of oligonucleotides, and the factors which influence the degree and specificity of hybridization, such as temperature, ionic strength and solvent composition, are well-known to those of skill in the art. See, for example, Sambrook et al., supra; Ausubel et al., supra; Innis et al. (eds.) PCR Protocols, Academic Press, San Diego, 1990; Hames et al. (eds.) Nucleic Acid Hybridisation: A Practical Approach, IRL Press, Oxford, 1985; and van Ness et al. (1991) Nucleic Acids Res. 19:5143–5151.

Hybridization Probes

In one application of the present invention, one or more FL-oligonucleotide conjugates are used as probe(s) to identify a target nucleic acid by assaying hybridization between the probe(s) and the target nucleic acid. A probe may be labeled with any detectable label of the present invention, or it may have the capacity to become labeled either before or after hybridization, such as by containing a reactive group capable of association with a label or by being capable of hybridizing to a secondary labeled probe, either before or after hybridization to the target. As a basis of this technique it is noted that conditions for hybridization of nucleic acid probes are well-known to those of skill in the art. See, for example, Sambrook et al., MOLECULAR CLONING: A LABORATORY MANUAL, Second Edition, Cold Spring Harbor Laboratory Press (1989); Ausubel et al., CURRENT PROTOCOLS IN MOLECULAR BIOLOGY, John Wiley & Sons (1987, 1988, 1989, 1990, 1991, 1992, 1993, 1994, 1995, 1996); Hames et al. (eds.) Nucleic Acid Hybridization: A Practical Approach, IRL Press, Oxford, 1985; and van Ness et al. Nucleic Acids Res. 19:5143–5151(1991).

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe or interaction between surface-bound and probe-conjugated ligands) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; and other known techniques. See, for example, Falkow et al., U.S. Pat. No. 4,358,535; Urdea et al., U.S. Pat. Nos. 4,868,105 and 5,124,246; Freifelder, Physical Biochemistry, Second Edition, Freeman & Co., San Francisco, 1982; Sambrook, et al., supra; Ausubel et al., supra; and Hames et al., supra.

Assays Utilizing Labeled Probes, Hydrolyzable Probe and Labeled Primers

Additional applications for oligonucleotide conjugates containing a fluorophore and quencher are found in assays in which a labeled probe is hybridized to a target and/or an extension product of a target, and a change in the physical state of the label is effected as a consequence of hybridization. A probe is a nucleic acid molecule that is capable of hybridizing to a target sequence in a second nucleic acid molecule. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytically digesting the probe. Any label attached to such a probe will be released, if the probe is hybridized to its target and if amplification is occurring across the region to which the probe is hybridized. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. This basic technique is described for example in U.S. Pat. No. 5,210,015 incorporated herein by reference.

In a variation of this technique, a probe contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

The use of FL-ODN-Q-DPI$_3$ conjugates in this and related methods allows greater speed, sensitivity and discriminatory power to be applied to these assays. In particular, the enhanced ability of MGB-oligonucleotide conjugates to allow discrimination between a perfect hybrid and a hybrid containing a single-base mismatch facilitates the use of hydrolyzable probe assays in the identification of single-nucleotide polymorphisms and the like, as described in the publication WO 995162A2, incorporated herein by reference. Examples 13 and 14 below serve to the utility of FL-ODN-Q-DPI$_3$ conjugates in this type of assay. It will be clear to those of skill in the art that compositions and methods, such as those of the invention, that are capable of discriminating single-nucleotide mismatches will also be capable of discriminating between sequences that have multiple mismatches with respect to one another.

Another application embodiment uses a self-probing primer with an integral tail, where the quencher/fluorophore is present in the hairpin, that can probe the extension product of the primer and after amplification hybridizes to the amplicon in a form that fluoresces. The probing of a target sequence can thereby be converted into a unimolecular event (Whitcombe, D. et al., Nat. Biotech., 17: 804–807 (1999)).

Fluorescence Energy Transfer

In further applications of the novel compositions of this invention, oligonucleotide conjugates containing a fluorophore/quencher pair (FL-ODN-Q) are used in various techniques which involve multiple fluorescent-labeled probes. In some of these assays changes in properties of a fluorescent label are used to monitor hybridization. For example, fluorescence resonance energy transfer (FRET) has been used as an indicator of oligonucleotide hybridization. In one embodiment of this technique, two probes are used, each containing a fluorescent label and a quencher molecule respectively. The fluorescent label is a donor, and the quencher is an acceptor, wherein the emission wavelengths of the donor overlap the absorption wavelengths of the acceptor. The sequences of the probes are selected so that they hybridize to adjacent regions of a target nucleic acid, thereby bringing the fluorescence donor and the acceptor into close proximity, if target is present. In the presence of target nucleic acid, irradiation at wavelengths corresponding to the absorption wavelengths of the fluorescence donor will result in emission from the fluorescence acceptor. These types of assays have the advantage that they are homogeneous assays, providing a positive signal without the necessity of removing unreacted probe. For further details and additional examples of these assays which are per se known in the art, see, for example, European Patent Publication 070685; and the publication Cardullo et al. (1988) Proc. Natl. Acad. Sci. USA 85: 8790–8794, both of which are incorporated herein by reference. Additional applications of the novel compositions of the present invention are in those and related techniques in which interactions between two different oligonucleotides that are both hybridized to the same target nucleic acid are, measured. The selection of appropriate fluorescence donor/fluorescence acceptor pairs will be apparent to one of skill in the art, based on the principle that, for a given pair, the emission wavelengths of the fluorescence donor will overlap the absorption wavelengths of the acceptor. The enhanced ability of DPI$_3$-oligonucleotide conjugates to distinguish perfect hybrids from hybrids containing a single base mismatch facilitates the use of FRET-based techniques in the identification of single-nucleotide polymorphisms and the like.

In another application of the novel compositions of the invention, the fluorescence of the FL-ODN-Q conjugate is quenched in its native state. But, after hybridization with the intended target the spatial arrangement of the fluorophore and quencher moieties are changed such that fluorescence occurs. For this basic technique see for example Tyagi et al., Nat. Biotech., 16: 49–53 (1998); and U.S. Pat. No. 5,876, 930, both of which are incorporated herein by reference.

It should be understood that in addition to the fluorophores which are found in accordance with the present invention especially useful to be used with the quenchers of the invention, and which fluorophores are incorporated into ODNs in accordance with the invention, a person of ordinary skill may choose additional fluorophores to be used in combination with the quenchers of the present invention, based on the optical properties described in the literature, such as the references: Haugland Handbook of Fluorescent Probes and Research Chemicals, Six Edition, Eugene, Oreg. pp. 235–236. 1996; Berlman, Handbook of Fluorescence Spectra of Aromatic Molecules, $2^{nd}$, Accademic Press, New York, 1971; Du et al., PhotochemCAD. A Computer-Aided Design and Research Tool in Photochemistry, Photochem. Photobiol. 68, 141–142 (1998). Therefore the use of the novel ODN quencher conjugates in combination with these known fluorophores is considered within the scope of the invention.

In another application, the minor groove binder, $DPI_3$, is coupled to a quencher in a $FL\text{-}ODN\text{-}Q\text{-}CDPI_3$ conjugate to improve signal to noise ratios (See Table 2.). Preferred quenchers are the quenchers of Formula 6 and more preferred the quenchers 8–11, 12–16 and 30.

Additional quenchers suitable for use in combination with the novel fluorophores (34, 37 and 44) of the invention include dabcylnitrothiazole, TAMRA, 6-(N-[7-nitrobenz-2-oxa-1,3-diazol-4-yl]amino)hexanoic acid, 6-carboxy-X-rhodamine (Rox) and QSY-7.

Another application of the novel fluorophore/quencher pairs of the invention is to incorporate the pair into enzyme substrates, where fluorescence is quenched because of the proximity of the fluorophore and quencher. However, after an enzyme cleaves the substrate the fluorophore and quencher become separated and fluorescence is observed. An example of this technique is described below using the phosphodiesterase enzyme. It will be clear to those schooled in the art that suitable substrates containing both the novel quenchers and fluorophores can be constructed for enzymes that cleave substrates.

Oligonucleotide Arrays

In another application, FL-ODNs of the present invention are utilized in procedures employing arrays of oligonucleotides. Examples for this technique that is per se known in the art include sequencing by hybridization and array-based analysis of gene expression. In these procedures, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. For a description of these techniques see for example, U.S. Pat. Nos. 5,492,806; 5,525,464; 5,556,752; and PCT Publications WO 92/10588 and WO 96/17957 all of which are incorporated herein by reference. Materials for construction of arrays include, but are not limited to, nitrocellulose, glass, silicon wafers and optical fibers.

Structural Considerations

The terms oligonucleotide, polynucleotide and nucleic acid are used interchangeably to refer to single- or double-stranded polymers of DNA or RNA (or both) including polymers containing modified or non-naturally-occurring nucleotides, or to any other type of polymer capable of stable base-pairing to DNA or RNA including, but not limited to, peptide nucleic acids which are disclosed by Nielsen et al. (1991) Science 254:1497–1500; bicyclo DNA oligomers (Bolli et al. (1996) Nucleic Acids Res. 24:4660–4667) and related structures. One or more MGB moieties and/or one or more fluorescent labels, and quenching agents can be attached at the 5' end, the 3' end or in an internal portion of the oligomer. A preferred MGB in accordance with the invention is $DPI_3$ and the preferred quencher is red13 amide.

Preferred in the present invention are DNA oligonucleotides that are single-stranded and have a length of 100 nucleotides or less, more preferably 50 nucleotides or less, still more preferably 30 nucleotides or less and most preferably 20 nucleotides or less with a lower limit being approximately 5 nucleotides.

Oligonucleotide conjugates containing a fluorophore/quencher pair with or without an MGB may also comprise one or more modified bases, in addition to the naturally-occurring bases adenine, cytosine, guanine, thymine and uracil. Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. The modified nucleotides which may be included in the ODN conjugates of the invention include 7-deazapurines and their derivatives and pyrazolopyrimidines (described in PCT WO 90/14353 incorporated herein by reference); and in co-owned and co-pending application Ser. No. 09/054,630.

Preferred base analogues of this type include the guanine analogue 6-amino-1H-pyrazolo[3,4-d]pyrimidin-4(5H)-one (ppG) PPG and the adenine analogue 4-amino-1H-pyrazolo[3,4-d]pyrimidine (ppA). PPA Also of use is the xanthine analogue 1H-pyrazolo[5,4-d]pyrimidin-4(5H)-6(7H)-dione (ppX). These base analogues, when present in an oligonucleotide, strengthen hybridization and improve mismatch discrimination. All tautomeric forms of naturally-occurring bases, modified bases and base analogues may be included in the oligonucleotide conjugates of the invention.

Similarly, modified sugars or sugar analogues can be present in one or more of the nucleotide subunits of an oligonucleotide conjugate in accordance with the invention. Sugar modifications include, but are not limited to, attachment of substituents to the 2', 3' and/or 4' carbon atom of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl.

Modified internucleotide linkages can also be present in oligonucleotide conjugates of the invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

Certain preferred embodiments of the invention involve the synthesis of numerous phophoramidites with various quencher chromophores and linkers and their incorporation at the 3'-end of fluorogenic MGB ODNs as shown in Reaction Scheme 3. Different fluorescent reporter groups (shown in Reaction Scheme 7) were also incorporated into the oligonucleotide probes and are described in the EXPERIMENTAL section. The fluorogenic properties of these ODN conjugates are described in Table 2. In other embodiments MGB molecules, due to their desirable improved hybridization properties, were incorporated into oligonucleotides containing both a fluorophore and a quencher, without loss in hybridization specificity, fluorescent quenching and fluoresent signal. The flat aromatic quencher residue coupled to the neighboring aromatic $DPI_3$ residue, have strict geometric requirements since the linker between the oligonucleotide and the $DPI_3$ residue must be flexible enough to allow positioning of the $DPI_3$ in the minor groove after DNA duplex formation.

Characteristics of Reagents of the Invention
A number of FL-ODN-Q-DPI$_3$ conjugates synthesized with the reagents and methods of the invention are shown in Formulas 7 to 16, where n specifies the number of bases in the oligonucleotide and R$_2$ is either FAM or TAMRA. "B" signifies a heterocyclic base attached to the deoxyribose sugar moiety.
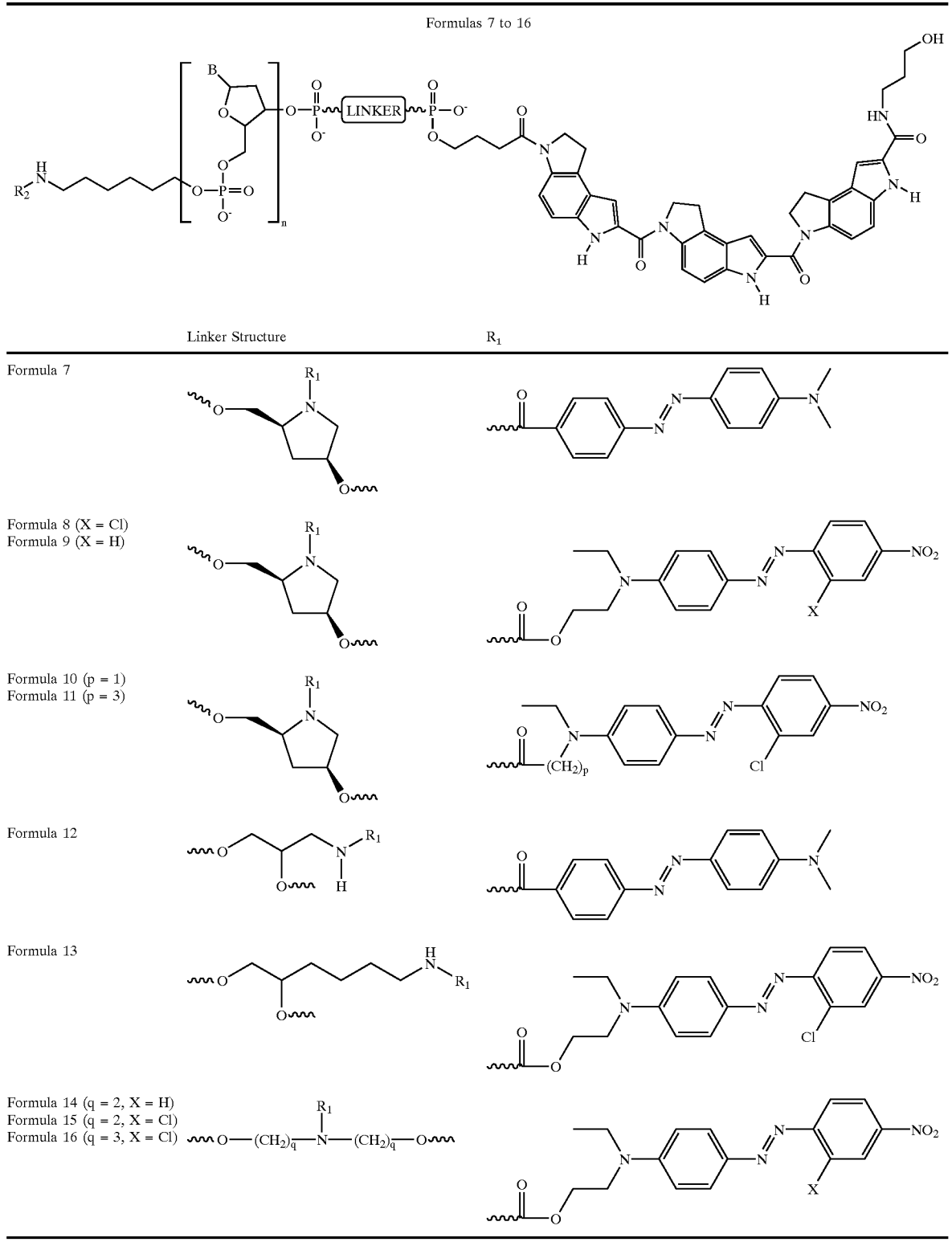

The quenchers incorporated in the compounds represented by Formulas 7–16 are the commercially available 2-[4-(4-nitrophenylazo)-N-ethylphenylamino]ethanol (Disperse Red 1), 2-[4-(2-chloro-4-nitrophenylazo)-N-ethylphenylamino]ethanol (Disperse Red 13) and 2-[4-(dimethylamino)phenylazo]benzoic acid, identified in this invention as Red1, Red 13 and dabcyl respectively.

UV Properties of Red 13 and Dabcyl Oligonucleotide Conjugates

Figure 2:
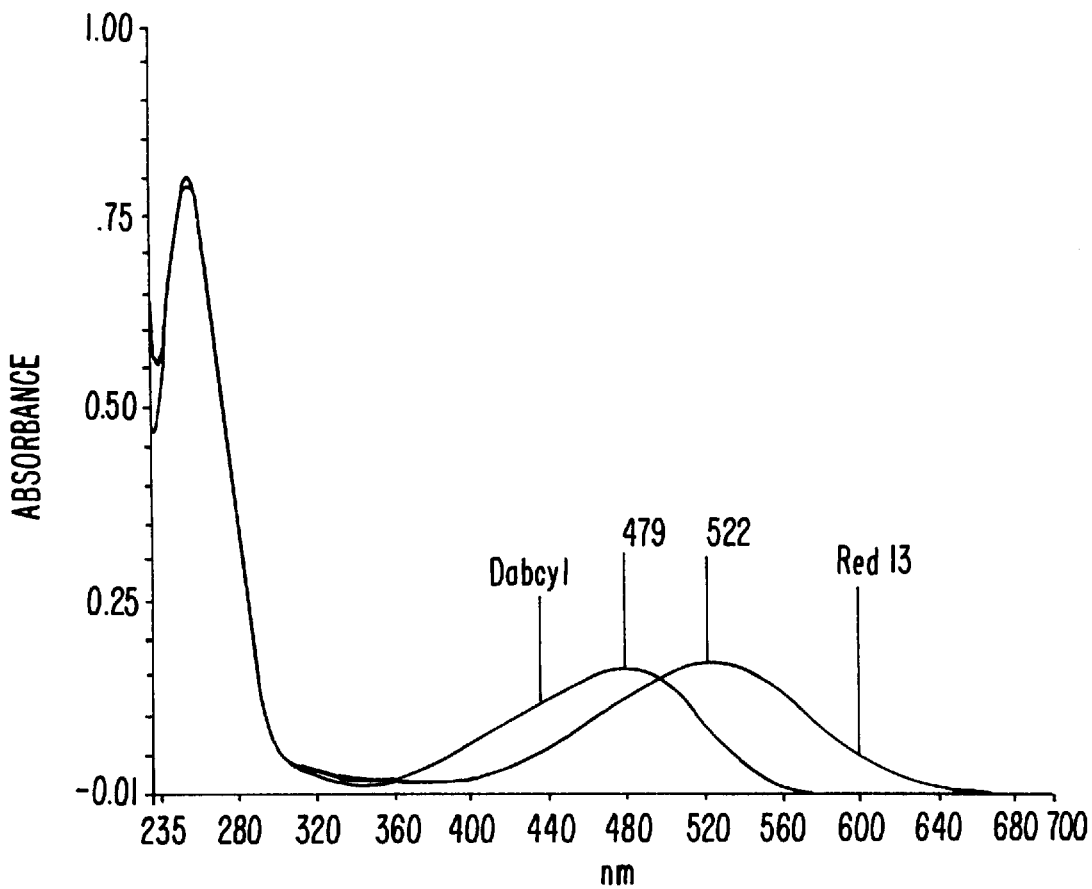
FIG. 2 is a graph showing the UV spectra of Dabcyl- and Red13 dye-modified DNA probes.

FIG. 2 shows the absorbance properties of the red13 chromophore (Formula 8, without $DPI_3$) in comparison to dabcyl (Formula 7, without $DPI_3$ when incorporated at the 3'-end of an otherwise unmodified DNA probe. The broader absorbance (especially at long wavelengths) of the red13 chromophore is a clear advantage. Note that the $\lambda_{max}$ for red13 is at 522 nm whereas the $\lambda_{max}$ for dabcyl is 479 nm. The absorbance of red13 is ideal for quenching of fluorescein (emission max=525 nm) but also overlaps with the fluorescence emission of other common laser dyes.

Quenching Properties of $DPI_3$ Probes with Various Quenchers and Linkers.

For the 10 fluorogenic probes described in Formulas 7 to 16 the fluorescence of a standard solution of each probe was measured before and after digestion with snake venom phosphodiesterase (PDE), as described in the EXPERIMENTAL section. This PDE assay allows the quenching properties of each probe to be compared. Fluorescence of the digested probe (signal) divided by the initial fluorescence (noise) gave a signal to noise ratio (S/N), presented in Table 1. Larger numbers for S/N reflect more efficient fluorescent quenching (lower fluorescent background) of the intact probe.

TABLE 1

Effect of different quenchers and linkers on fluorogenic probes shown in Formulas 7–16.

| Formula # (quencher) | S/N[a] ($R_2$ = FAM) | S/N[a] (R2 = TAMRA) |
| --- | --- | --- |
| 7 (dabcyl) | 16 | 13 |
| 8 (red13) | 21 | 21 |
| 9 (red1) | 24 | 21 |
| 10 (red13) | 13 | 33 |
| 11 (red13) | 27 | 21 |
| 12 (dabcyl) | 13 | 7 |
| 13 (red13) | 23 | 21 |
| 14 (red1) | 19 | 3 |
| 15 (red13) | 24 | 4 |
| 16 (red13) | 22 | 24 |

[a]Signal to noise (S/N) was determined using the phosphodiesterase assay described in Example 13. The ODN sequence was 5'-gagggatgtaaaaat (SEQUENCE Id. No. 1). The fluorophores ($R_2$) studied here is either 6-carboxyfluorescein (6-FAM) or 6-carboxytetramethylrhodamine (TAMRA).

It is clear from the data in Table 1 that the red13 chromophore and the closely related red1 chromophore are better quenchers for both FAM and TAMRA with a variety of linkers than dabcyl. The linker can affect quenching by the red13 chromophore. For example, Formula 14 and Formula 15 worked well with FAM, but had poor quenching efficiency for TAMRA. It is somewhat surprising that dabcyl worked so well, especially for the TAMRA probes. As described below, effective FRET quenching by dabcyl is a specific case for MGB probes.

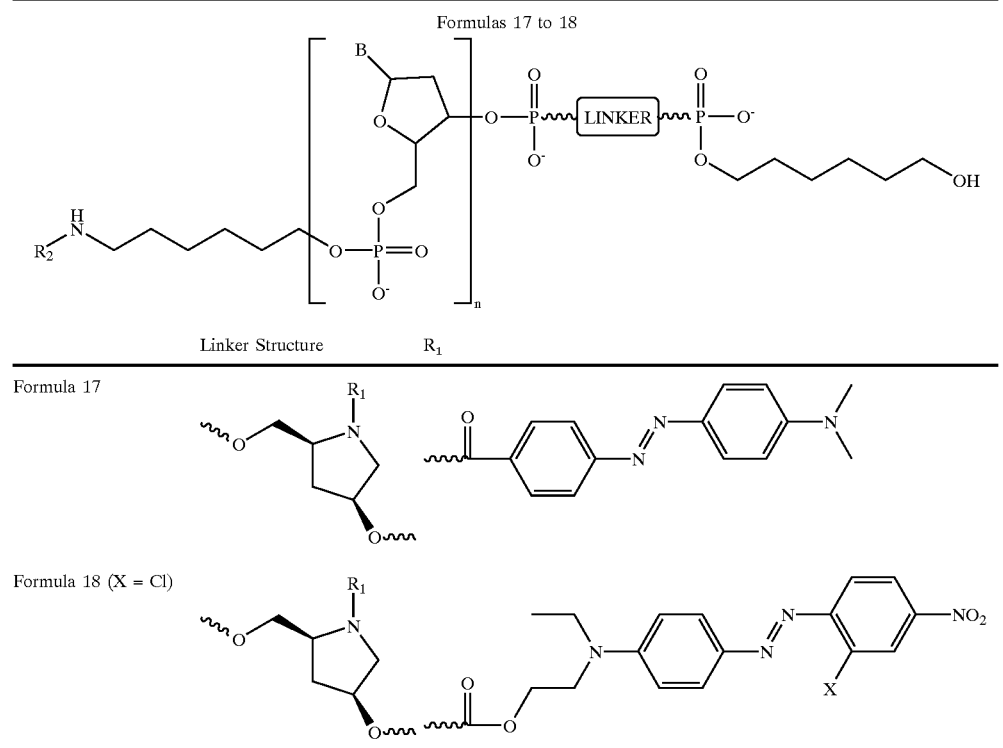

Comparison of Quenching Properties of DPI$_3$ Probes and Probes without DPI$_3$.

To further show the advantages of the red13 quencher chromophore, fluorogenic probes with a 3'-hexanol blocking group (without MGB) were compared. The structure and fluorescent properties of 13 fluorogenic probes with the same sequence were compared using the PDE assay. A red-sensitive detector was used in this study (Table 2) whereas a blue-sensitive detector was used in the study shown in Table 1 (S/N for identical ODNs are different because different detectors have different sensitivities for the same fluorphore). The following structural variables are summarized in Table 2: Probe type (no-MGB vs. MGB ), Quencher (dabcyl vs. Red13 vs. Red13 amide), and Reporter dye (FAM vs. TAMRA).

TABLE 2

Fluorescent properties of oligonucleotides with various Quenchers/Fluorophores[1].

| Formula # | Probe type | Quencher | FAM (S/N) | TAMRA (S/N) |
|---|---|---|---|---|
| 17 | no-DPI$_3$ | dabcyl | 4.7 | 3.9 |
| 18 | no-DPI$_3$ | red13 | 11.6 | 5.8 |
| 7 | DPI$_3$ | dabcyl | 23 | 23.5 |
| 8 | DPI$_3$ | red13 | 35 | 108 |
| 30 (R1 = 2-Cl, t = v = 3) | DPI$_3$ | red13 amide | 48 | 97 |

[1]Signal to noise (S/N) was determined using the phosphodiesterase assay described above. The ODN sequence was 5'-gagggatgtaaaaat (SEQUENCE Id. No. 1). The linker structure of the dabcyl or red13 quenchers (Q) is shown in Formulas 7 and 8 respectively. The linker structure of the red13 amide is shown in 30 Reaction Scheme 7, R$_0$ is NO$_2$, R$_1$ = 2-Cl, R$_2$ = R$_3$ = R$_4$ = —H; t = v = 3.

It is clear from the data shown in Table 2, that in the probes which do not contain DPI$_3$ the dye Red13 quencher works better than dabcyl for both FAM and TAMRA. In DPI$_3$ containing probes, the dye Red13 works better in combination with FAM and much better in combination with TAMRA. Both 8 and 30 work better in DPI$_3$ containing probes with both fluorophores, with 30 showing the best S/N ratio for FAM. Thus, it was found that the Red13 chromophore is a more efficient quencher than dabcyl for long wavelength fluorescent reporter groups. For the most commonly used fluorophore (FAM) a 2.5-fold increase in S/N was observed for standard (no-DPI$_3$) probes. This improved quenching by red13 is consistent with the increased spectral overlap presented in FIG. 2 and a standard FRET mechanism. The increased S/N of both 8 and 30 when incorporated into the DPI$_3$ probes is dramatic and surprising. The combination of the red13 quencher and the DPI$_3$ resulted in a 10-fold increase in S/N for FAM quenching and a 28-fold increase in S/N for TAMRA quenching.

It is surprising and not understood how the DPI$_3$ residue helps improve fluorescent quenching by the dabcyl and red13 chromophores. Without wishing to be bound by theory, it is presently postulated that the random coil conformation of the fluorogenic probe in solution is more structured in the DPI$_3$ probes such that the average distance between the fluorophore and quencher is closer than in probes without MGB. This closer average distance in the DPI$_3$ probes (tighter coil) would give rise to more efficient FRET. The exact nature of this interaction is not known, but UV spectra of the quencher and dye chromophores are not affected by the DPI$_3$. This is in contrast to the fluorogenic hairpin probes where the UV spectra are changed by the constrained conformation (collisional quenching).

Performance of Fluorogenic DPI$_3$ Probes in a "Real-Time" PCR Assay.

Figure 3:
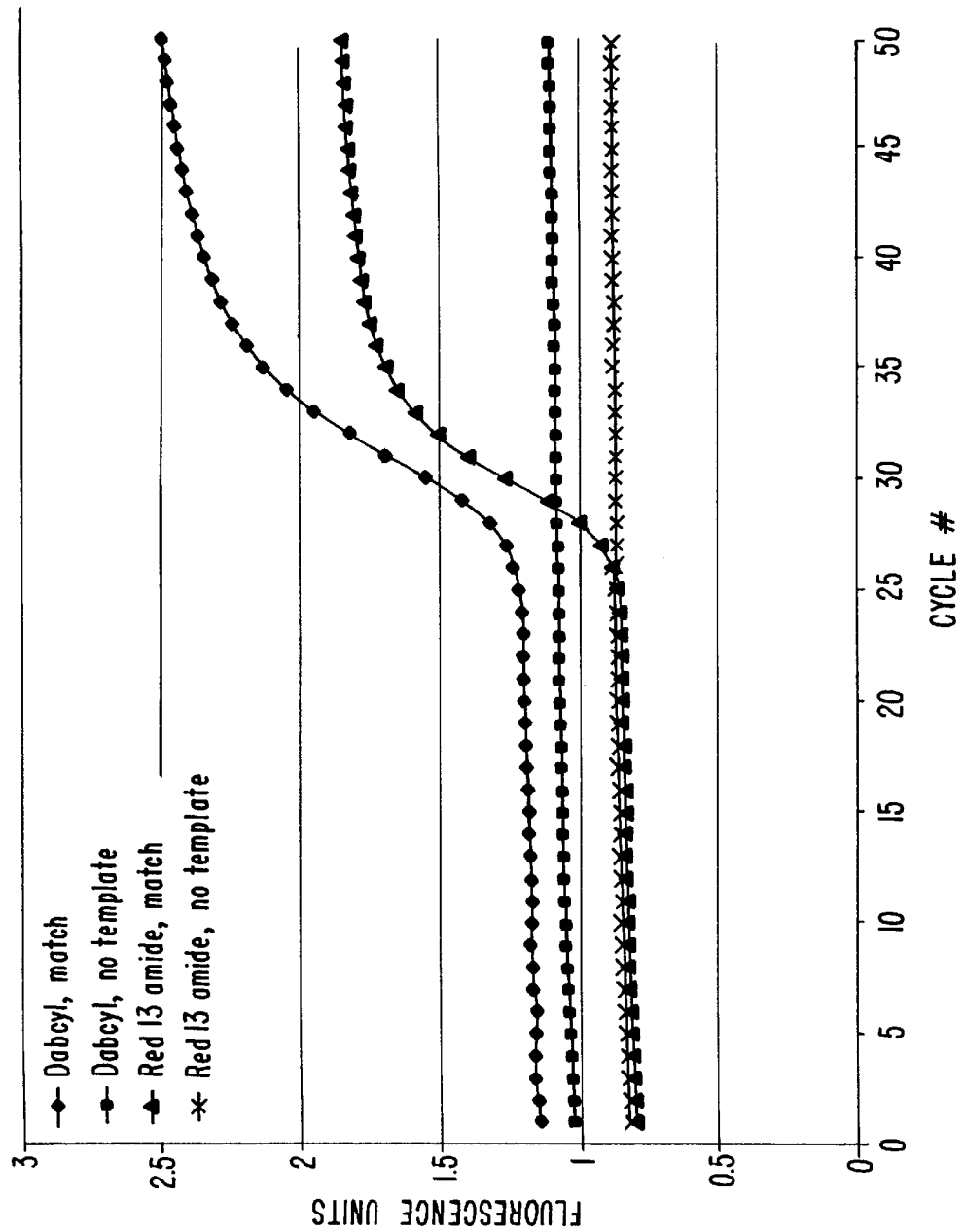
FIG. 3 is a graph showing the performance of fluorogenic MGB probes in a "real-time" PCR assay.

DPI$_3$ probes prepared with 5'-fluorescein and the red13 amide linker were tested in the 5'-nuclease assay to see if the hybridization properties were compatible with the linker system. As shown in FIG. 3, both dabcyl and Red13 worked as quenchers for fluorescein in the 5'-nuclease assay when used in MGB probes. Red13 performed better than dabcyl as evidenced by the lower initial fluorescence (background) and the higher plateau after PCR. Current commercially available thermal-cycling fluorimeters can not read longer wavelength dyes in real-time PCR, but the red13 chromophore was shown to give a good S/N with TAMRA containing probes in an end point analysis after PCR.

According to another general method, the 5'-fluorophore-ODN-Q-MGB conjugates of the instant invention have improved performance in assays designed to detect DNA targets by direct hybridization. A basic description of this method is found in U.S. Pat. No. 5,876,930, incorporated herein by reference. In this assay format, the non-hybridized probes (quenched by FRET) become fluorescent upon forming a rigid duplex structure, thereby separating the quencher and fluorophore.

Red13 Chromophore Quenches a Broad Range of Fluorescent Reporter Groups

A series of DPI$_3$ probes with the red13 amide were prepared with several different fluorescent reporter groups to examine the effective range of quenching. Probes were digested with PDE as usual and showed good S/N for dyes which emit from 458 –665 nm.

TABLE 3

Performance of Fluorogenic DPI$_3$ Probes with Various Fluorophores.

| Fluorophore (FL) | Ex λ (nm) | Em λ (nm) | S/N |
|---|---|---|---|
| coumarin | 378 | 458 | 32 |
| FAM | 488 | 522 | 63 |
| Cy3 | 541 | 565 | 61 |
| TAMRA | 547 | 582 | 37 |
| resorufin | 549 | 595 | 110 |
| Cy5 | 641 | 665 | 36 |

The structure of the fluorogenic probes was FL-ODN-Q-CDPI$_3$ where Q is the red13 amide and the ODN sequence was 5'-GTC CTG ATT TTA C (SEQUENCE Id. No. 2). The fluorophores FAM, TAMRA, cy3 and cy5 were incorporated using commercially available phosphoramidite reagents. The coumarin and resorufin fluororophores were incorporated using phosphoramidites 34 and 37 which were prepared as described below.

Figure 4:
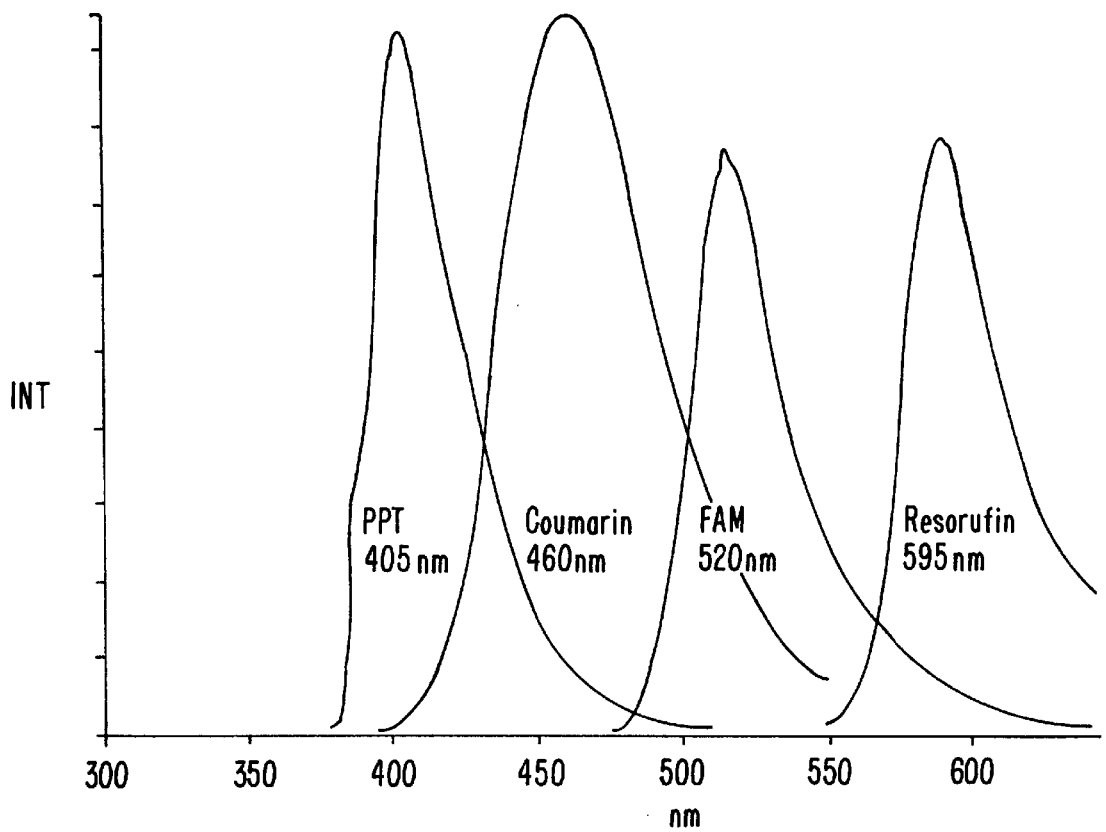
FIG. 4 is a graph showing the fluorescent spectra of violet, FAM and resorufin dye containing DNA probes.

The fluorescent emission is well separated from FAM, as shown in the overlayed spectra in FIG. 4. As shown in Table 3, the resorufin fluorescence is also quenched by the red13 chromophore. Thus the resorufin phosphoramidite has excellent properties for use in FRET probes and in combination with FAM for multicolor analysis.

As shown in Table 3, the coumarin fluorescence is also quenched by the red13 chromophore. Thus, the coumarin phosphoramidite reagent can be incorporated in FRET probes and particularly in combination with FAM for multicolor analysis.

Fret-based enzyme substrates

The improved quencher molecules can be used in other FRET based assay systems. According to another general application of the invention, a quencher molecule and fluorophore are attached to an enzyme substrate, which through its catalytic action on this Q-substrate-fluorophore conjugates cleaves and separates the Q and fluorophore molecules. For example, the pentafluorophenyl activated ester 11 shown in Reaction Scheme 3 can be used for labeling lysine residues of peptides for studying proteolytic enzymes.

EXPERIMENTAL PROCEDURES

General Experimental

All air and water sensitive reactions were carried out under a slight positive pressure of argon. Anhydrous solvents were obtained from Aldrich (Milwaukee, Wis.). Flash chromatography was performed on 230–400 mesh silica gel. Melting points were determined on a Mel-Temp melting point, apparatus in open capillary and are uncorrected. Elemental analysis was performed by Quantitative Technologies Inc. (Boundbrook, N.J.). UV-visible absorption spectra were recorded in the 200–400-nm range on a UV-2100 (Shimadzu) or a Lambda 2 (Perkin Elmer) spectrophotometers. $^1$H NMR spectra were run at 20° C. on a Bruker WP-200 or on a Varian XL-200 spectrophotometer; chemical shifts are reported in ppm downfield from $Me_4Si$. Thin-layer chromatography was run on silica gel 60 F-254 (EM Reagents) aluminum-backed plates.

EXAMPLE 1

2-({4-[(2-Chloro-4-nitrophenyl)diazenyl] phenyl}ethylamino)ethyl(2S,4R)-2-{[bis(4-methoxyphenyl)phenylmethoxy]methyl}-4-{[bis (methylethyl)amino](2-cyano-ethoxy) phosphinooxy}pyrrolidinecarboxylate (5)

2-({4-[(2-Chloro-4-nitrophenyl)diazenyl] phenyl}ethylamino)ethyl (5S,3R)-3-Hydroxy-5-(hydroxymethyl)pyrrolidinecarboxylate (3)

A solution of 2-[4-(2-chloro-4-nitrophenylazo)-N-ethylphenylamino]ethanol (Disperse Red 13, Aldrich Chemical Co., 9.0 g, 25.80 mmol) and 4-nitrophenyl chloroformate (Aldrich Chemical Co., 9.4 g, 46.61 mmol) in 90 ml of anhydrous pyridine was stirred at 70° C. for 40 min, affording intermediate 2. Ethanol (5.0 ml) was added to the reaction solution followed by trans-hydroxyprolinol (Reed et al. Bioorg. Chem. 2: 217–225 (1991) (42 ml of a 0.5 M solution in ethanol) and triethylamine (3.2 ml). The resultant solution was stirred for 30 min at 70° C. The solution was evaporated to dryness and the residue was suspended in 1 liter of water and extracted with ethyl acetate (3×500 ml). The pooled extracts were dried over sodium sulfate, filtered and evaporated. The residue was purified by silica gel chromatography eluting with a gradient of 0–10% methanol in ethyl acetate. The pure product fractions were evaporated and precipitated from ethyl acetate-ether: 9.2 g (59%); TLC (ethyl acetate), $R_f$=0.25. $^1$H NMR (DMSO-$d_6$) δ 8.43 (1H, d, J=2.5 Hz), 8.25 (1H, dd, J=9.0 and 2.4 Hz), 7.86 (2H, d, J=9.1 Hz), 7.78 (1H, d, J=9.0 Hz), 6.96 (2H, d, J=9.3 Hz), 4.88 (1H, m), 4.67 (1H, t, J=5.7 Hz), 4.19 (3H, m), 3.80 (1H, m), 3.73 (2H, t, J=5.4 Hz), 3.56 (2H, q), 3.46 (1H, t, J=4.7 Hz), 3.27 (1H, m), 1.94 (1H, m), 1.79 (1H, m), 1.17 (3H, t, J=6.8 Hz). Anal. Calcd for $C_{22}H_{26}ClN_5O_6$*0.2 $H_2O$: C, 53.32; H, 5.37; N, 14.13. Found: C, 53.24; H, 5.25; N, 13.99.

2-({4-[(2-Chloro-4-nitrophenyl)diazenyl] phenyl}ethylamino)ethyl (5S,3R)-5-{[bis(4-Methoxyphenyl)phenylmethoxy]methyl}-3-hydroxypyrrolidinecarboxylate (4)

To a solution of 3 (9.1 g, 18.53 mmol) in 130 ml of anhydrous pyridine was added 6.26 g of dimethoxytrityl chloride. The solution was stirred for 3 h. at room temperature and then poured into 300 ml of 5% sodium bicarbonate solution. The mixture was extracted with ethyl acetate (2×300 ml) and the combined extracts were dried over sodium sulfate, filtered and evaporated. The residue was purified by silica gel chromatography eluting with a gradient of 20–0% hexane in ethyl acetate followed by a gradient of 0–2% methanol in ethyl acetate. The chromatography eluent also contained 1% triethylamine. The pure product fractions were combined affording an amorphous solid: 12.66 g (86%); TLC (ethyl acetate), $R_f$=0.44. $^1$H NMR (DMSO-$d_6$) δ 8.45 (1H, s), 8.26 (1H, d, J8.9 Hz), 7.82 (3H, m), 7.27 (4H, m), 7.16 (5H, m), 6.95–6.79 (6H, m), 4.95 (1H, m), 4.32 (1H, m), 4.14 (1H, m), 3.99 (2H, m), 3.73 (1H, m), 3.69 (6H, s), 3.56 (1H, m), 3.40–3.30 (2H, m), 3.14 (1H, m), 2.10–1.82 (2H, m), 1.16 (3H, m), 1.06 (3H, t, J=6.5 Hz). Anal. Calcd for $C_{43}H_{44}ClN_5O_8$*0.2 $H_2O$: C, 64.73; H, 5.61; N, 8.78. Found: C, 65.08; H, 5.70; N, 8.31.

2-({4-[(2-Chloro-4-nitrophenyl)diazenyl] phenyl}ethylamino)ethyl (2S,4R)-2-{[bis(4-Methoxyphenyl)phenylmethoxy]methyl}-4-{[bis (methylethyl)amino](2-cyanoethoxy) phosphinooxy}pyrrolidinecarboxylate (5)

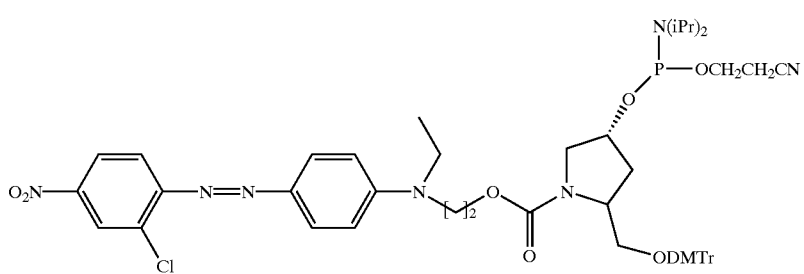

To a solution of 4 (12.63 g, 15.91 mmol) dissolved in 440 ml of anhydrous methylene chloride, containing 8.0 ml of N,N-diisopropylethylamine, was added 5.94 ml of 2-cyanoethyl diisopropylchlorophosphoramidite. The solution was stirred 30 min under argon at room temperature. The reaction mixture was treated with 10 ml of methanol and poured into 400 ml of 5% sodium bicarbonate solution. The organic phase was dried over sodium sulfate and evaporated. The residue was purified by silica gel chromatography eluting with a gradient of 40–20% hexane in ethyl acetate (2% triethylamine). The pure product fractions were evaporated affording an amorphous solid: 14.75 g (93% yield). $^{31}$P NMR (DMSO-$d_6$) δ 146.93 (singlet). Anal. Calcd for $C_{52}H_{61}ClN_7O_9$*1.0 $H_2O$: C, 61.68; H, 6.27; N, 9.68. Found: C, 61.44; H, 6.47; N, 9.35.

EXAMPLE 2

RED 13-Pyrrolidine-DMTr-CPG 12

Synthesis of Pentafluorophenyl Ester (11) and RED 13-Pyrrolidine-DMTr-CPG (12) Reactions Scheme 3

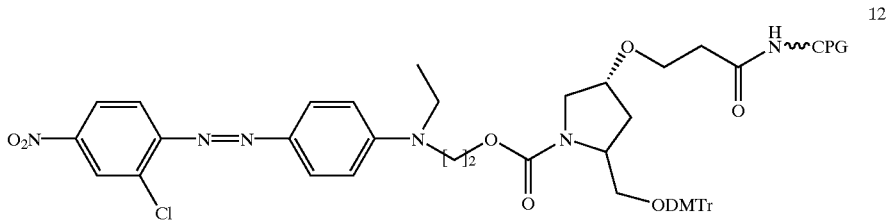

The pentafluorophenyl ester (11) is synthesized by the same method used for the synthesis of Compound 22 as described in Example 4 and Reaction Scheme 5.

RED 13-Pyrrolidine-DMTr-CPG (12)

10 g of LCAA-CPG was combined with 5 ml of a 0.3 M solution of 11 in DMF and agitated gently overnight, when it was filtered and washed with 2×100 mL of DMF, 2×100 mL of acetonitrile, and 2×100 mL of ether. Traces of ether were removed in vacuo (oil pump). Unreacted amino groups were acetylated by treating the CPG with 40 mL of dry pyridine and 5 mL of acetic anhydride. After swirling for 1.5 h, the CPG was filtered and washed with 2×100 mL of DMF, 2×100 mL of acetonitrile, and 2×100 mL of ether. Traces of ether were removed in vacuo (oil pump). The CPG was analyzed for MMT loading by treating 3–5 mg of CPG in 25 mL of 1:1/70% perchloric acid:methanol. The absorbance of the released MMT cation was recorded at 472 nm and loading level was adjusted to be between 30–40 mmol/g of CPG using the equation:

MMT loading (mmol/g)=A472×volume (in mL)×14.3, wt of CPG (mg)

EXAMPLE 3

2-(4-Nitrophenyl)ethyl 3-(pyrrolo[4,5-e]indolin-7-ylcarbonyl)pyrrolo[4,5-e]indoline-7-carboxylate (17). (Reaction Scheme 4)

2-(4-Nitrophenyl)ethyl 3-[(tert-Butyl)oxycarbonyl] pyrrolo[4,5-e]indoline-7-carboxylate (14)

Ten grams (33.1 mmol) of 3-[(tert-butyl)oxycarbonyl] pyrrolo[3,2-e]indoline-7-carboxylic acid (Boger, D. L., Coleman, R. S., Invergo, B. J. (1987) *J. Org. Chem.* 52, 1521.), well dried, are placed into an argon filled flask, and 84 mL of THF and 10.4 mL (66.2 mmol) of diethyl azodicarboxylate (DEAD) are added. Then a dropping funnel is placed atop the flask (flushed with argon) and a water bath (to cool the flask) is placed under it. A solution of 17.3 g (66 mmol) of triphenylphosphine and 6.64 g (39.7 mmol) of 2-(p-nitrophenyl) ethanol in 160 mL of ethyl ether is made. This solution is added to the dropping funnel, and then to the reaction flask, dropwise, with stirring. The reaction is allowed to proceed for an hour, at which time, a TLC analysis is done (2:1 hexanes/ethyl acetate) examined by UV (254 nm) to determine whether the reaction is complete. If it is complete, then the baseline spot (bluish) will disappear and the product, with an $R_f$ of 0.55, will appear as a dark spot. Often, especially if the reactants are not entirely dry, another portion of triphenylphosphine and DEAD are required. If so, a tenth of the original amounts is usually sufficient, i.e., 1.73 g of triphenylphosphine and 1.04 mL of DEAD. These can be added neat to the stirred solution. Allow to react another hour, after which another TLC analysis usually reveals complete reaction. The product usually precipitates out in part; this is collected bt filtration and washed with methanol, then recrystallized by dissolving in a minimum amount (typically, 80–100 ml) of warm acetone and adding four times that volume of warm methanol. Cool to 4° C. for several hours or perhaps overnight. The supernatant from the original precipitation is saved and evaporated to a syrup or until dry. It too is dissolved in a minimum amount of warm acetone; typically about 100–120 mL of warm acetone. The total amount or acetone used for the two recrystallizations is usually approximately 200 mL. As before, an amount of warm methanol equal to four times the amount of acetone is added. The solution is cooled; crystallization begins almost at once but is allowed to continue several hours to overnight. The recrystallizations are quite efficient, but the product from the reaction supernatant is usually not quite as pure and is purified by recrystallization. The yield is approximately 85%. (mp 191–193° C.) $^1$H NMR (DMSO-d6) δ: 11.83 (s, 1H), 8.18 (d, J=8.5 Hz, 2H), 7.84 (br s, 1H), 7.64 (d, J=8.5 Hz, 2H), 7.25 (d, J=8.8 Hz), 6.96 (s, 1H), 4.56 (t, J=6 Hz, 2H), 4.00 (t, J=8.8 Hz, 2H), 3.21 (m, 4H), 1.51 (s, 9H). Combustion Analysis: Found: C, 63.16%; H, 5.56%; N, 9.45%. Calculated for 0.4 mole added water: C, 62.8%; H, 5.7%; N, 9.16%.

2-(4-Nitrophenyl)ethyl Pyrrolo[4,5-e]indoline-7-carboxylate (15)

Two grams (4.43 mmol) of 14 are weighed into a round bottomed flask. Then, in a fume hood, 25 mL (325 mmol) of trifluroacetic acid is added, and the flask is capped and stirred. The solid dissolves in about a minute. The mixture is stirred for 1 hour, at which time deprotection will be done (HPLC can be used as a check). The acid is evaporated on a rotary evaporator (use a trap) and the product is dissolved in 100 mL of methylene chloride. This is extracted twice with 100 mL of half to ⅔ saturated sodium bicarbonate solution. The aqueous layers are back-extracted once with ~50 mL of methylene chloride and this is combined with the rest. The organic layer is dried over sodium sulfate twice and evaporated to give a brown solid. If desired, this material can be recrystallized by diluting a very concentrated solution in methylene chloride with methanol and cooling. Yields approaching 100% are usually obtained. mp 192–194° C. $^1$H NMR (DMSO-d6) δ: 11.51 (s, 1H), 8.18 (d, J=8.5 Hz, 2H), 7.63 (d, J=8.5 Hz, 2H), 7.11 (d, J=8.5 1H), 6.80 (s, 1H), 6.70 (d, J=8.5 Hz), 5.03 (br s, 1H), 4.54 (t, J=6.4 Hz, 2H), 3.46 (t, J=8.6 Hz, 2H), 3.19 (m, 2H), 3.04 (t, J=8.6 Hz, 2H).

Combustion Analysis: Calculated for $C_{19}H_{17}N_3O_4$: C,64.94%; H, 4.88%; N, 11.96%. Found: C, 65.50%; H, 4.70%; N, 11.64%

2-(4-Nitrophenyl)ethyl 3-({3-[(tert-butyl) oxycarbonyl]pyrrolo[4,5-e]indolin-7-yl}carbonyl) pyrrolo[4,5-e]indoline-7-carboxylate (16)

3.09 grams (8.8 mmol) of 15 is mixed with 2.66 grams (8.8 mmol) of 13 (Boger, D. L., Coleman, R. S., Invergo, B. J. (1987) *J. Org. Chem.* 52, 1521.), and 46 mL of DMF is added. Then 3.85 grams (8.77 mmol) of 1-[3-(dimethylamino)propyl]-3-ethylcarbodiimide hydrochloride are added. The mixture is stirred for about three hours. The mixture is initially homogeneous, but as the stirring proceeds, a precipitate of the product forms. The solvent DMF is evaporated under a high vacuum, and about 100 mL of methanol is added. The mixture is swirled and filtered in a sintered glass funnel, then thoroughly washed with 3×50 mL portions of methanol. Then it is dried in vacuo. Yields usually approach 100 percent. mp: 132°–134° C. $^1$H NMR (DMSO-d6) δ: 11.93 (s, NH, 1H),11.62 (s, NH,1H), 8.30 (br s, aromatic proton, 1H), 8.27 (br s, aromatic proton, 1H), 8.19 (d, aromatic protons, J=8.3 Hz, 2H), 7.65 (d, aromatic protons, J=8.3 Hz, 2H), 7.34 (d, J=9 Hz, aromatic proton, 1H), 7.29 (d, J=9 Hz, aromatic proton, 1H), 7.07 (s, aromatic proton, 1H), 6.98 (s, aromatic proton, 1H), 4.60 (m, aliphatic protons, 4H), 4.02 (t, J=8.5 Hz, aliphatic protons, 2H), 3.40 (t, J=8 Hz, aliphatic protons, 2H), 3.24 (m, aliphatic protons, 4H), 1.52 (s, 3xCH$_3$, 9H). Combustion Analysis: Calculated: C, 66.13%; H, 5.23%; N, 11.02%. Found: C, 65.94%; H, 5.19%; N, 11.07%.

2-(4-Nitrophenyl)ethyl 3-(Pyrrolo[4,5-e]indolin-7-ylcarbonyl)pyrrolo[4,5-e]indoline-7-carboxylate (17)

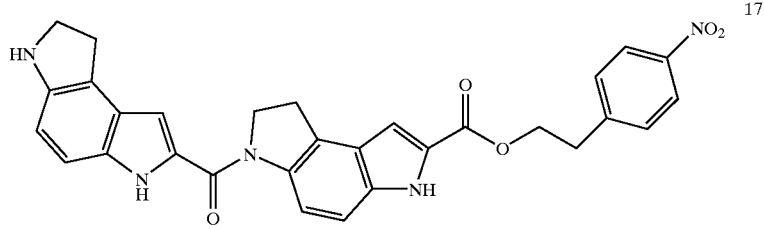

5 grams of 16 are placed in a flask. 100 mL of trifluoroacetic acid is added, and the mixture is stirred. After an hour, the acid is evaporated on a rotary evaporator and 100 mL saturated sodium bicarbonate solution and 100 mL of water are added. The mixture is agitated or sonicated for ~½ hours, then filtered and washed with water and then methanol, and dried in vacuo. The material may be recrystallized. It is dissolved in a minimum amount of warm DMF, and then approximately a threefold portion of methanol is added and the solution is sonicated a few minutes. A cream to brown material crystallizes out. This is washed with methanol, and dried in vacuo. The yield approaches theoretical values.$^1$H NMR (DMSO-d6) δ: 11.96 (s, NH, 1H), 11.71 (s, NH, 1H), 8.30 (br s, aromatic proton, 1H), 8.27 (br s, aromatic proton, 1H), 8.19 (d, aromatic protons, J=8.5 Hz, 2H), 7.66 (d, aromatic protons, J=8.3 Hz, 2H), 7.34 (m, aromatic protons, 2H), 7.08 (s, aromatic proton, 1H), 7.03 (s, aromatic proton, 1H), 4.60 (m, aliphatic protons, 4H), 3.68 (t, J=8 Hz, aliphatic protons, 2H), 3.40 (t, J=8 Hz, aliphatic protons, 2H), 3.24 (m, aliphatic protons, 4H). Combustion Analysis: Found: C, 63.55%; H, 4.42%; N, 11.95%. Calculated, for ½ mole sodium bicarbonate contaminant: C, 63.43%; H, 4.45%; N, 12.13%.

EXAMPLE 4

2,3,4,5,6-Pentafluorophenyl 3-[4-({3-[bis(4-Methoxyphenyl)phenylmethoxy]propyl}{4-[(2-chloro-4-nitrophenyl)diazenyl]phenyl}amino) butanoyl]pyrrolo[4,5-e]indoline-7-carboxylate (24) (Reaction Scheme 5)

Ethyl 4-[(3-Hydroxypropyl)phenylamino]butanoate (19)

A mixture of 3-(phenylamino)propan-1-ol (Huang, Yande; Arif, Atta M.; Bentrude, Weseley G.; J.Org.Chem.; 58; 23; 1993; 6235–6246) (65.6 g, 0.43 mol), ethyl 4-bromobutyrate (104.5 g, 0.54 mol) and 100 mL of ethyldiisopropylamine is stirred at 100° C. for 1 h. The reaction is cooled to room temperature and partitioned between water 400 mL and ethyl acetate (500 mL). The organic layer is washed with saturated NaHCO$_3$, brine and dried over Na$_2$SO$_4$. The oil obtained after concentration is chromatographed on silica eluting with 10% EtOH/CHCl$_3$. Concentration of the appropriate fractions affords 115 g (100%) of the desired product as a colorless, viscous oil. $^1$H NMR (CDCl$_3$) δ: 7.23 (m, 2H), 6.72 (m, 3H), 4.14 (q, J=7 Hz, 2H), 3.72 (t, J=6Hz, 2H), 3.43 (t, 7 Hz, 2H), 3.34 (t, 7 Hz, 2H), 2.35 (t, 7 Hz), 1.88 (m, 4H), 1.26 (t, 7 Hz, 3H).

Ethyl 4-({4-[(2-Chloro-4-nitrophenyl)diazenyl] phenyl}(3-hydroxypropyl)amino)butanoate (20)

2-Chloro-4-nitroaniline 2.5 g (10 mmol) is placed into a 125 mL flask and 6 mL of water is added. Agitation and sonication partially dissolves the yellow chloronitroaniline. Then the stirred solution is cooled with ice in a fume hood and 15.8 mL of concentrated (~12 M) HCl is added. Most of the yellow material dissolves at this point. The flask is fitted with a dropping funnel, and a solution of 1.51 g (21.9 mmol) sodium nitrite in 3–4 mL of water is added to the dropping funnel and slowly added to the solution in the flask with stirring, over about 20 minutes. When this is complete, 0.6 g (~21 mmol) of urea is added followed by 2.73 g of ethyl 4-[(3-hydroxypropyl)phenylamino]butanoate as a solution in 8.2 mL acetic acid. After a minute 20 g of sodium acetate in 50 mL of water is added. The mixture is allowed to stir for an hour at room temperature. Most of the product is separated as an emulsion. The mixture is partitioned between ethyl acetate and water. The organic layer is washed with NaHCO$_3$ (3×50 ml), brine and dried over anhydrous sodium sulfate. Then the organic solvents are evaporated to a syrup. The crude product is chromatographed on silica gel (1.5×20 inches) eluting with 50% ethyl acetate/hexane. The appropriate fractions are collected, combined, evaporated (30–40 degrees), and dried in a vacuum. The product is a dark oil. The yield is approximately 68–70%. $^1$H NMR (DMSO-d6) δ: 8.42 (d, J=2.5 Hz, aromatic proton, 1H), 8.24 (dd, $J_1$=9 Hz, $J_2$=2.5 Hz, aromatic proton, 1H), 7.86 (d, J=9 Hz, 2H), 7.77 (d, J=9 Hz, 1H), 6.92 (d, J=9 Hz, aromatic protons, 2H), 4.67 (t, J=6 Hz, OH, 1H), 4.07 (q, J=7 Hz, $CH_2O$, 2H), 3.5 (m, aliphatic protons, 6H), 2.40 (t, J=7 Hz, aliphatic protons, 2H), 1.84 (m, aliphatic protons, 2H), 1.72 (m, aliphatic protons, 2H), 1.18 (t, J=7 Hz, $CH_3$, 3H).

4-({4-[(2-Chloro-4-nitrophenyl)diazenyl]phenyl}(3-hydroxypropyl)amino)butanoic Acid.

To a stirred solution of 20 (4.48 g, 10 mmole) in 40 mL of THF added 40 mL of ethanol followed by a solution of KOH (0.84 g, 15 mmol) in 20 mL of water and 20 mL of ethanol. The mixture is stirred overnight and concentrated. The residue suspended in 125 mL of water, treated with 2.6 mL (~3 eqv.) of acetic acid, and cooled to 4° C. The resulting solid is filtered off, washed with water, and dried. Yield is quantitative. $^1$H NMR (DMSO-d6) δ: 8.42 (d, J=2.5 Hz, aromatic proton, 1H), 8.23 (dd, $J_1$=9 Hz, $J_2$=2.5 Hz, aromatic proton, 1H), 7.82 (d, J=9Hz, 2H), 7.90 (d, J=9 Hz, 1H), 7.03 (d, J=9 Hz, aromatic protons, 2H), 4.8 (br s, OH, 1H), 3.5 (m, aliphatic protons, 6H), 1.86 (t, J=6 Hz, aliphatic protons, 2H), 1.72 (m, aliphatic protons, 4H).

4-({3-[bis(4-Methoxyphenyl)phenylmethoxy]propyl}{4-[(2-chloro-4-nitrophenyl)diazenyl]phenyl}amino)butanoic Acid (21)

4.21 g (10 mmol) of the acid from the previous step is placed into a 250 mL round bottom flask. Dry pyridine (50–100 ml) is added and evaporated (30–40 degrees) with a rotary evaporator. The process is repeated once or twice to remove all traces of water.

Dry pyridine (80 mL) is added to the contents of the flask. Then 4.07 g (12 mmol) of dimethoxytrityl chloride is added. After being stirred for 1 h pyridine is evaporated and the resulting syrup is dissolved in a few milliliters of 18:1:1 methylene chloride/methanol/triethylamine. A silica gel column (~1.5"×20") is prepared with an eluent of 18:1:1 methylene chloride/methanol/triethylamine and the product is run through the column, collecting and combining the appropriate fractions. After the solvents are removed by evaporation the resulting amorphous solid contains some triethylammonium salts in addition to the desired product. The impurity does not interfere with the next step and the product is used without additional purification.

2,3,4,5,6-Pentafluorophenyl 4-({3-[bis(4-methoxyphenyl)phenylmethoxy]propyl}{4-[(2-Chloro-4-nitrophenyl)diazenyl]pheny}amino)butanoate (22)

To the flask containing 21 (10 mmol) is added 7 mL of triethylamine followed by 100 mL of methylene chloride, 2.05 mL of pentafluorophenyl trifluoroacetate (PFP-TFA) is then added. The solution is stirred for half an hour. At the end of this time, the reaction is usually complete. (TLC: 2:1 hexane/ethyl acetate). The solvent is removed on the rotary evaporator to give a syrup which is chromatographed on silica eluting with 1:3 ethyl acetate/hexane. Appropriate fractions are collected, combined, evaporated and dried under vacuum. The yield is 41%. $^1$H NMR (DMSO-d6) δ: 8.43 (d, J=2.5 Hz, aromatic proton, 1H), 8.24 (dd, $J_1$=9 Hz, $J_2$=2.5 Hz, aromatic proton, 1H), 7.83 (d, J=9 Hz, aromatic proton, 1H), 7.78 (d, J=9 Hz, aromatic proton, 1H), 7.42–7.15 (m, aromatic protons, 10H), 7.07 (m, aromatic protons, 2H), 7.00–6.80 (m, aromatic protons, 4H), 3.72 (s, $2xCH_3$, 6H), 3.56 (m, aliphatic protons, 2H), 3.48 (t, J=6.3 Hz, aliphatic protons, 2H), 3.08 (t, J=5 Hz, aliphatic protons, 2H), 2.89 (t, J=7 Hz, aliphatic protons, 2H), 1.95 (m, aliphatic protons, 2H), 1.86 (m, aliphatic protons, 2H).

Methyl 3-[4-({3-[bis(4-Methoxyphenyl)phenylmethoxy]propyl}{4-[(2-chloro-4-nitrophenyl)diazenyl]phenyl}amino)butanoyl]pyrrolo[4,5-e]indoline-7-carboxylate (23)

To a solution of 22 (3.0 g, 3.37 mmol) in 15 mL anhydrous DMF is added triethylamine (0.75 mL) followed by methyl pyrrolo[4,5-e]indoline-7-carboxylate (Boger, D. L., Coleman, R. S., Invergo, B. J. (1987) J. Org. Chem. 52, 1521.) (0.8 g, 3.7 mmol). The resultant solution is stored at room temperature for 20 h. The reaction is analyzed by HPLC to confirm its completeness. DMF is removed on a rotary evaporator equipped with an oil pump. The residue, dark syrup is suspended in 50% ethylacetate/hexanes (~25 mL). The mixture is sonicated to initiate the crystallization. The crystals are stirred for 15 min, collected by filtration on a sintered glass funnel, washed with methanol (2×30 mL) and dried under vacuum. The yield of the desired product is 2.7 g (87%) as a deep-purple solid. $^1$H NMR (DMSO-d6) δ: 11.93 (d, J=1.7 Hz, indole NH, 1H), 8.43 (d, J=2.5 Hz, aromatic proton, 1H), 8.3–8.2 (m, aromatic protons, 2H), 7.85–7.75 (m, aromatic protons, 3H), 7.45–7.18 (m, aromatic protons, 10 H), 7.05 (d, J=1.8 Hz, aromatic proton, 1H), 6.97 (d, J=9 Hz, aromatic protons, 2H), 6.87 (d, J=9 Hz, aromatic protons, 4H), 4.12 (t, J=8 Hz, aliphatic protons, 2H), 3.87 (s, ester $CH_3$, 3H), 3.71 (s, $CH_3$, 6H), 3.60 (br t, aliphatic protons, 2H), 3.45 (br t, aliphatic protons, 2H), 3.29 (br t, aliphatic protons, 2H), 3.08 (t, J=5 Hz, aliphatic protons, 2H), 2.5 (br t, obscured by DMSO signal, aliphatic protons, 2H), 1.88 (br m, aliphatic protons, 4H).

2,3,4,5,6-Pentafluorophenyl 3-[4-({3-[bis(4-Methoxyphenyl)phenylmethoxy]propyl}{4-[(2-chloro-4-nitrophenyl)diazenyl]phenyl}amino)butanoyl]pyrrolo[4,5-e]indoline-7-carboxylate (24)

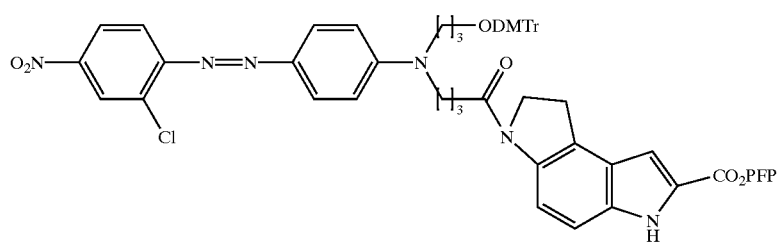

24

1. Hydrolysis of the Methyl Ester

To a solution of 23 (2.67 g, 2.9 mmol) in 25 mL THF are added methanol (25 mL) and 5% LiOH, monohydrate in H₂O (10 mL). The resultant suspension is stirred at 50° C. (bath temperature) for 90 min. by which time a clear solution is obtained. TLC analysis shows no starting material. Solvent is removed under vacuum and the product is partitioned between $CH_2Cl_2$ and cold 10% citric acid. The organic phase is neutralized with triethylamine, dried over $Na_2SO_4$ and concentrated. The resultant product (amorphous solid) is dried in high vacuum for at least 3 h and used in the next step without additional purification.

2. PFP Ester Preparation

The product obtained in the previous step is dissolved in 100 mL anhydrous DMF. Triethylamine (2 mL) is added followed by PFP-TFA (2 mL, 4.4 mmol). The reaction is stirred for 30 min and analyzed by HPLC. No starting material, free acid should be observed. DMF is evaporated and the residue, deep purple syrup is suspended in 100 mL MeOH. After stirring for 30 min, a dark precipitate is formed which is collected by filtration on a sintered glass funnel, washed with methanol (3×20 mL) and dried under vacuum (15–30 h). This procedure yields 2.7 g (94%) of the desired product as a purple solid. ¹H NMR (DMSO-d6) δ: 12.45 (d, J=1.8 Hz, indole NH, 1H), 8.43 (d, J=2.5 Hz, aromatic proton, 1H), 8.38 (d, J=9 Hz, aromatic proton, 1H), 8.24 (dd, $J_1$=9 Hz, $J_2$=2.5 Hz, aromatic proton, 1H), 7.85–7.75 (m, aromatic protons, 3H), 7.52–7.18 (m, aromatic protons, 11 H), 6.97 (d, J=9 Hz, aromatic protons, 2H), 6.88 (d, J=9 Hz, aromatic protons, 4H), 4.16 (t, J=8.5 Hz, aliphatic protons, 2H), 3.71 (s, CH₃, 6H), 3.61 (br t, aliphatic protons, 2H), 3.47 (br t, aliphatic protons, 2H), 3.32 (br t, aliphatic protons, 2H), 3.08 (t, J=5 Hz, aliphatic protons, 2H), 2.5 (br t, obscured by DMSO signal, aliphatic protons, 2H), 1.88 (br m, aliphatic protons, 4H).

EXAMPLE 5

2,3,4,5,6-Pentafluorophenyl 3-{[3-({3-[4-({3-[bis(4-Methoxyphenyl)phenylmethoxy]propyl}{4-[(2-chloro-4-nitrophenyl)diazenyl]phenyl}amino)butanoyl]pyrrolo[4,5-e]indolin-7-yl}carbonyl)pyrrolo[4,5-e]indolin-7-yl]carbonyl}pyrrolo[4,5-e]indoline-7-carboxylate (25a). where $R_1$=2-Cl and t=v=3 (Reaction Scheme 6)

2-(4-Nitrophenyl)ethyl 3-{[3-({3-[4-({3-[bis(4-Methoxyphenyl)phenylmethoxy]propyl}{4-[(2-chloro-4-nitrophenyl)diazenyl]phenyl}amino)butanoyl]pyrrolo[4,5-e]indolin-7-yl}carbonyl)pyrrolo[4,5-e]indolin-7-yl]carbonyl}pyrrolo[4,5-e]indoline-7-carboxylate (25)

Into a 100 mL round bottom flask is weighed out 1.31 g (1.22 mmol) of 24. This is dissolved in 25 mL of dimethylformamide. Then 0.81 mL of triethylamine is added, and finally 0.623 g (1.162 mmol) of 17. The reaction mixture is left overnight, then the solution is concentrated to ~10 mL and the resultant precipitate is filtered off, using a sintered glass filter funnel. The solid is washed with generous volumes of methanol (stirring the sludge in the filter with the methanol before applying the vacuum) several times and ether. When the effluent is clear and essentially colorless, the deep violet precipitate is dried in vacuo to afford 1.5 g (90%) of the desired product. ¹H NMR (DMSO-d6) δ: 11.96 (s, indole NH, 1H), 11.76 (s, indole NH, 1H), 11.69 (s, indole NH, 1H), 8.43 (d, J-2.4 Hz, aromatic proton, 1H), 8.35–8.20 (m, aromatic protons, 4H), 8.19 (d, J=9 Hz, aromatic protons, 2H), 7.85–7.75 (m, aromatic protons, 3H), 7.66 (d, J=9 Hz, aromatic protons, 2H), 7.45–7.18 (m, aromatic protons, 12H), 7.10 (s, aromatic proton, 1H), 7.01 (s, aromatic proton, 1H), 6.99 (m, aromatic protons, 3H), 6.88 (d, J=9 Hz, aromatic protons, 4H), 4.61 (m, aliphatic protons, 6H), 4.14 (t, J=8.5 Hz, aliphatic protons, 2H), 3.71 (s, 2×CH₃O, 6H), 3.59 (m, aliphatic protons, 2H), 3.43 (m, aliphatic protons, 6H), 3.34 (m, obscured by water signal, aliphatic protons, 2H), 3.22 (m, aliphatic protons, 2H), 3.08 (t, J=5 Hz, aliphatic protons, 2H), 2.5 (t, obscured by DMSO signal, COCH₂—, 2H), 1.89 (br m, aliphatic protons, 4H). Analysis: Calculated: C, 68.27%; H, 4.95%; N, 10.81%. Found: C, 68.08%; H, 4.98%; N, 10.63%.

2,3,4,5,6-Pentafluorophenyl 3-{[3-({3-[4-({3-[bis(4-Methoxyphenyl)phenylmethoxy]propyl}{4-[(2-chloro-4-nitrophenyl)diazenyl]phenyl}amino)butanoyl]pyrrolo[4,5-e]indolin-7-yl}carbonyl)pyrrolo[4,5-e]indolin-7-yl]carbonyl}pyrrolo[4,5-e]indoline-7-carboxylate (25a)

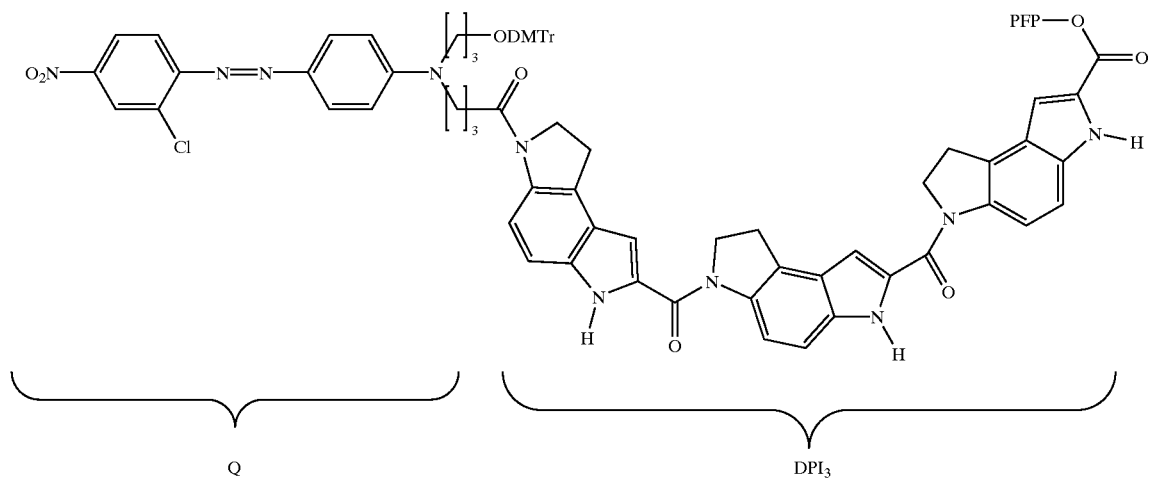

25a

Q · DPI₃

Into a flask is placed 1.0 g (0.73 mmol) of the product from the previous step, 40 mL of THF, and 2.46 g of DBU. The mixture is stirred at 50 degrees for 4 hours, then removed from the heat and evaporated to 15 to 20 ml. About 40 mL of methanol is added to the product and the mixture is agitated and sonicated. Then the precipitate is filtered off with a sintered glass funnel and washed with 40–60 mL of additional methanol, followed by a similar amount of ethyl ether, each time stirring the material in the filter prior to applying the vacuum so that the effluent soon becomes clear. The product is dried in vacuo for an hour or two before it is used in the next step. The material is dissolved in 20 mL of DMF in a 100 mL flask and stirred to dissolve. Then 0.6 mL (4.3 mmol) of triethylamine is added, followed by 0.6 mL of PFP-TFA. The reaction mixture is stirred under argon overnight, and then evaporated to a gum and a ~10 mL of DMF is added, followed by ~80 mL of methanol. This mixture is swirled and sonicated, and then the product, which precipitates out, is filtered off and dried in vacuo. Yield is 85–90%. $^1$H NMR (DMSO-d6) δ: 12.01 (s, indole NH, 1H), 11.76 (s, indole NH, 1H), 11.69 (s, indole NH, 1H), 8.43 (d, J-2.4 Hz, aromatic proton, 1H), 8.40 (br s, aromatic proton, 1H), 8.35–8.20 (m, aromatic protons, 3H), 7.85–7.75 (m, aromatic protons, 3H), 7.59 (d, J=1.2 Hz, aromatic proton, 1H), 7.45–7.18 (m, aromatic protons, 12H), 7.13 (s, aromatic proton, 1H), 6.99 (m, aromatic protons, 3H), 6.88 (d, J=9 Hz, aromatic protons, 4H), 4.66 (m, aliphatic protons, 4H), 4.14 (t, J=8.5 Hz, aliphatic protons, 2H), 3.71 (s, 2xCH$_3$O, 6H), 3.59 (m, aliphatic protons, 2H), 3.43 (m, aliphatic protons, 6H), 3.34 (m, obscured by water signal, aliphatic protons, 2H), 3.08 (t, J=5 Hz, aliphatic protons, 2H), 2.5 (t, obscured by DMSO signal, COCH$_2$—, 2H), 1.89 (br m, aliphatic protons, 4H). Analysis: Found: C, 63.58%; H, 4.13%; N, 9.53%. Calculated, for 2.3 moles of water: C, 63.97%; H, 4.21%; N, 9.44%.

EXAMPLE 6

DMTrO-Red 13-Amide-CDPI$_3$-CPG (29) (Reaction Scheme 7)

3-[(4-Methoxyphenyl)diphenylamino]propan-1-ol (26)

4 g (53 mmol) of 3-aminopropanol was dissolved by stirring in 50 mL of methylene chloride in an oven dried 250 mL round bottom flask. This solution was stoppered and set aside. 7.7 g (24.9 mmol) of monomethoxytrityl chloride (MMT-Cl, Aldrich reagent grade) was dissolved in another 50 ml of methylene chloride. An oven dried dropping funnel was fitted to the flask and the MMT-Cl solution was added to the funnel. The MMT-Cl solution was then added to the solution in the flask over ~10 min (some heat develops). After an hour the reaction was analyzed by TLC (1:1 v/v hexanes/ethyl acetate, R$_f$ 0.4) and found to be complete. Visualization of TLC spots by ninhydrin spray/heat showed a trace of (faster moving) bis-MMT side product. The reaction mixture was added to 200 mL of water standing over 200 mL of methylene chloride in a separatory funnel. The mixture was shaken and separated into layers; the aqueous layer was discarded and the organic layer was washed with an additional 200 mL of water. The organic layer was dried over 10–20 g of sodium sulfate and evaporated to give ~7 g of the tritylated amine as a pale yellow syrup. This compound did not require further purification and was dried overnight. After several days the syrup solidified. The product was recrystallized from ether-hexanes to give 4.6 g (53% yield) of 26 as a white solid (mp=89.5–90.5° C.). Anal. calcd for C$_{23}$H$_{25}$NO$_2$: C, 79.51; H, 7.25; N, 4.03. Found: C, 79.48; H, 7.18; N, 3.98.

2-[({3-[(4-Methoxyphenyl)diphenylamino] propyl}oxycarbonyl)methoxy]acetic Acid, Triethylammonium Salt (27)

2.72 g (7.83 mmol) of the alcohol (26) was dissolved in 20 mL of methylene chloride with 1.3 mL (9.4 mmol) of triethylamine and 1.1 g (9.5 mmol) of glycolic anhydride. The mixture was stirred for 2 h (became homogeneous). TLC showed clean reaction (R$_f$=0.35 in 9:1/methylene chloride:methanol). The solvents were removed by evaporation and the residue was chromatographed on a 1.5×18 inch silica gel column packed with 93% methylene chloride, 5% methanol, and 2% triethylamine. The fractions containing product were combined and solvent was removed by evaporation. Co-evaporation with dry DMF ensured removal of traces of water and of residual volatile solvents. Yield of the colorless syrup (27) was assumed to be 100%. The syrup was dissolved in dry DMF to give a final volume of 23.4 mL (~0.33 M solution).

Synthesis of N-MMT Diglycolate CPG (28)

10 g of LCAA-CPG was combined with 5 mL of a 0.33 M solution of 27 in DMF (1.66 mmol) in a 100 mL round bottom flask. A solution of 2.5 mL of diisopropylethylamine, 0.11 g (0.8 mmol) of HOBT and 0.63 g (1.66 mmol) of HBTU was prepared and added to the CPG. The mixture was stoppered and swirled for 16 h on an orbital shaker (150 rpm). The CPG was filtered on a medium porosity sintered glass funnel and washed with 2×100 mL of DMF, 2×100 mL of acetonitrile, and 2×100 mL of ether. Traces of ether were removed in vacuo (oil pump). Unreacted amino groups were acetylated by treating the CPG with 40 mL of dry pyridine and 5 mL of acetic anhydride. After swirling for 1.5 h, the CPG was filtered and washed with 2–100 mL of DMF, 2×100 mL of acetonitrile, and 2×100 mL of ether. Traces of ether were removed in vacuo (oil pump). The CPG was analyzed for MMT loading by treating 3–5 mg of CPG in 25 mL of 1:1/70% perchloric acid:methanol. The absorbance of the released MMT cation was recorded at 472 nm and loading level was calculated to be 95.7 μmol/g of CPG using the equation:

MMT loading (μmol/g)=A$_{472}$×volume (in mL)×14.3÷wt of CPG (mg)

Synthesis of CPG 29

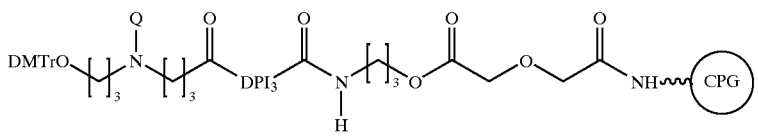

29

4 g of N-MMT diglycolate CPG (28) was weighed into a medium porosity sintered glass funnel. The CPG was detritylated by treating with 25 mL of 3% TCA/DCM. After stirring briefly with a spatula, the mixture reacted for 5 min before filtering (turned yellow). The process was repeated 4 times until the filtrate was colorless. The CPG was washed with 4×40 mL of methylene chloride. The filtrate was discarded to organic waste, and the CPG was neutralized by treatment with 40 mL of 20% triethylamine in acetonitrile. After briefly stirring with a spatula, the mixture was filtered and washed with 2×40 mL of acetonitrile, and 2×40 mL of ether. Traces of ether were removed in vacuo (oil pump).

The de-tritylated CPG was used immediately for the following immobilization reaction.

0.259 g (180 μmol) of 25a was shaken with 12 mL of dry DMSO in a 15 mL polypropylene tube. After 15 min, the dark purple solution was added to 4 g of detritylated diglycolate CPG (in a 50 mL round bottom flask). This corresponds to an offering ratio of 45 μmol PFP ester per gram of CPG. An additional 5 mL of DMSO was added to the polypropylene tube to dissolve residual PFP ester and the solution was added to the CPG. 2 mL of triethylamine was added and the mixture was stoppered and swirled on an orbital mixer for 14 h. The CPG was filtered and washed with 2×50 mL of DMSO, 2×50 mL of acetonitrile, and 2×50 mL of ether. Traces of ether were removed in vacuo (oil pump). Unreacted amino groups were acetylated by treating the CPG with 10 mL of dry pyridine and 3 mL of acetic anhydride. After swirling for 6 h, the CPG was filtered and washed with 2×50 mL of DMF, 2×50 mL of acetonitrile, and 2×50 mL of ether. Traces of ether were removed in vacuo (oil pump). The CPG was analyzed for DMT loading by treating 3–5 mg of CPG in 25 mL of 1:1/70% perchloric acid:methanol. The absorbance of the released DMT cation was recorded at 498 nm and loading level was calculated to be 45 μmol/g of CPG using the equation:

DMT loading (μmol/g)=$A_{498}$×volume (in mL)×14.3÷wt of CPG (mg)

EXAMPLE 7

Synthesis of FL-ODN-Red 13-Amide-CDPI$_3$ (30)

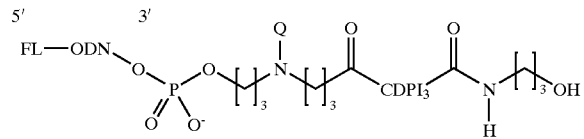

The oligonucleotides were synthesized on the CPG 29 using standard phosphoramidite coupling chemistry except that the standard 0.1 I$_2$ oxidizing solution was diluted to 0.01–0.015 to avoid iodination of the MGB moiety. FAM and TET were incorporated at the 5'end using the corresponding phosphoramidites available from Glen Research.

EXAMPLE 8

4-{[N-(6-{[bis(Methylethyl)amino](2-cyanoethoxy)phosphinooxy}hexyl)carbamoyl]methyl}-2-oxo-2H-chromen-7-yl 2,2-dimethylpropanoate (34a)

N-(6-Hydroxyhexyl)-2-(7-hydroxy-2-oxo(2H-chromen-4-yl))acetamide (32a)

(7-Hydroxy-2-oxo-2H-chromen-4-yl)-acetic acid methyl ester (1) was synthesized according to Baker et al. (J.Chem.Soc.; 1950; 170, 173.). A solution of 31 (2.0 g, 8.5 mmol) and 6-aminohexanol (4.0 g, 34.1 mmol) in 15 mL of DMF was heated at 80° C. for 24 h. DMF was evaporated under vacuum to afford the mixture of the product and the excess 6-aminohexanol as a viscous syrup. Chromatography on silica eluting with 10% MeOH/CH$_2$Cl$_2$ and evaporation of the pure product fractions afforded a white solid which was washed with ether and dried under vacuum. The yield was 2.05 g (75%).

4-{[N-(6-Hydroxyhexyl)carbamoyl]methyl}-2-oxo-2H-chromen-7-yl 2,2-dimethylpropanoate (33a)

To a solution of 32a (2.0 g, 6.3 mmol) in 20 mL of dry pyridine was added 4,4'-dimethoxytriphenylmethyl chloride (3.0 g, 8.9 mmol). The solution was kept at room temperature for 1 h, TLC analysis (ethyl acetate, R$_f$ ~0.7) showed complete reaction (protection of the primary hydroxy group). To this solution was added trimethylacetic anhydride (2.0 mL, 9.9 mmol) followed by triethylamine (5 mL) and 4-(dimethylamino)pyridine (0.3 g). The mixture was stirred for 5 h, TLC analysis showed complete protection of the phenol group (R$_f$~0.9, ethyl acetate). Methanol was added to quench excess anhydride. Pyridine was removed by evaporation under vacuum and co-evaporation with xylene. The product obtained was partitioned between ethyl acetate and 2% NaHCO$_3$, the organic phase was concentrated under vacuum to give the crude DMT protected 33a.

To remove the DMT group the DMT derivative was dissolved in 100 mL of 10% MeOH in CH$_2$Cl$_2$ and treated with 0.5 mL of trifluoroacetic acid. After being stirred for 1 h, the reaction mixture was neutralized with triethylamine (0.7 mL) and concentrated. The resultant viscous oil was partitioned between ethyl acetate and water. The organic layer was dried over Na$_2$SO$_4$ and concentrated. The solid obtained was suspended in ether (50 mL) and stirred for 30 min. The desired product was the insoluble material, and was collected by filtration, washed with ether and dried. The yield of the title product 33 was 1.6 g (64%).

4-{[N-(6-{[bis(Methylethyl)amino](2-cyanoethoxy)phosphinooxy}hexyl)carbamoyl]methyl}-2-oxo-2H-chromen-7-yl 2,2-dimethylpropanoate (34)

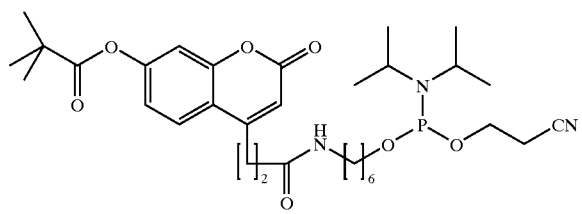

To a solution of 33a (0.6 g, 1.5 mmol) in 10 mL of anhydrous CH$_2$Cl$_2$ was added triethylamine (0.4 mL) followed by 2-cyanoethyl diisopropylchlorophosphoramidite (0.35 mL, 1.6 mmol). The solution was kept at room temperature for 1 h and treated with 0.1 mL of MeOH. The solvent was evaporated and the residue was partitioned between ethyl acetate and saturated NaHCO$_3$. The organic phase was washed with saturated NaCl, dried over Na$_2$SO$_4$ and concentrated. The crude product was chromatographed on silica eluting with 5% triethylamine in ethyl acetate. Concentration of the pure product fractions and drying under vacuum afforded 0.59 g (65%) of 34 as a colorless, viscous oil.

EXAMPLE 9

8-(3-{[bis(Methylethyl)amino](2-cyanoethoxy)phosphinooxy}propyl)-7-oxophenoxazin-3-yl 2,2-dimethylpropanoate (37a). (Reaction Scheme 9)

7-Hydroxy-2-(3-hydroxypropyl)phenoxazin-3-one (35a)

A suspension of 4-nitrosorecorcinol (4.5 g, 32.4 mmol), 4-(3-hydroxypropyl)benzene-1,3-diol (Forchiassin, M.; Russo, C. J.Heterocyc. Chem. 20, 1983, 493–494.) (4.0 g, 23.8 mmol) and MnO2 (2.5 g, 17.6 mmol) in 50 mL of MeOH was cooled to ~0° C. (ice bath). To this suspension was added dropwise 2.5 mL of conc. H$_2$SO$_4$ and the reaction was stirred at room temperature for 5 h. The precipitated red resazurin compound was collected by filtration, washed with methanol and dried. The yield was 5.5 g. This product was not homogeneous, it was contaminated with resorufin compound and manganese salts.

The crude resazurin compound was suspended in a mixture of 200 mL of water and 50 mL of conc. NH$_4$OH. Zinc dust (2.0 g) was added and the suspension was stirred for 20 min. The resultant purple mixture was filtered, the filtrate was vigorously stirred on air to oxidize the leuco resorufin, the product of partial over reduction. The reaction was acidified with acetic acid, the brown solid formed was collected by filtration washed with water and dried. The yield was 2.1 g. The material contained ~50% of 2,3,4-trihydro-2H-pyrano[3,2-b]phenoxazin-9-one, product of intramolecular cyclization which had been carried over from the first step. The rest of the material was the desired title compound 35.

8-(3-Hydroxypropyl)-7-oxophenoxazin-3-yl 2,2-dimethylpropanoate (36b)

A suspension of 35a (2.0 g) in 50 mL of pyridine was treated with 4,4'-dimethoxytriphenylmethyl chloride (5.0 g, 14.8 mmol) and stirred for 5 h. The mixture was filtered to remove some insoluble material and the filtrate was treated with trimethylacetic anhydride (2 mL). The solution was stirred for 15 h and MeOH (2 mL) was added to quench excess anhydride. After being stirred for 3 h, the reaction mixture was concentrated under vacuum. Residual pyridine was removed by co-evaporation with triethylamine and xylene. The resultant crude product 36a was chromatographed on silica eluting with 50% ethyl acetate/hexane.

The DMT derivative was dissolved in 100 mL of 10% MeOH/$CH_2Cl_2$ and treated with 0.5 mL of trifluoroacetic acid. After 1 h, triethylamine (2 mL) was added and the solution was concentrated. Chromatography on silica (ethyl acetate) and drying afforded 0.38 g of the desired product as an orange solid.

8-(3-{[bis(Methylethyl)amino](2-cyanoethoxy) phosphinooxy}propyl)-7-oxophenoxazin-3-yl 2,2-dimethylpropanoate (37a)

37a

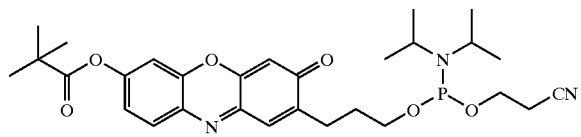

36b (0.38 g, 1.1 mmol) was dissolved in 6 mL of anhydrous $CH_2Cl_2$. Triethylamine (1.5 mL) was added followed by 2-cyanoethyl diisopropylchlorophosphoramidite (0.29 mL, 1.3 mmol). The solution was kept at room temperature for 30 min, MeOH (0.1 mL) was added and the reaction was concentrated under vacuum. The residue obtained was partitioned between ethyl acetate and $NaHCO_3$. The organic phase was washed with saturated NaCl, dried over $Na_2SO_4$ and concentrated to afford the crude amidite. It was dissolved in 2 mL of ether and added dropwise to 50 mL of hexane. The resultant orange solid was collected by filtration, washed with hexane and dried. The yield was 0.4 g.

EXAMPLE 10

3-{[[(tert-Butyl)(methylethyl)amino][2-(4-{3-butyl-7-[(4-methyphenyl)carbonyl]-2,4,6,8-tetraoxo-1-(phenylcarbonyl)(1,3,5,7,9,10-hexahydopyrimidino[5',4'-5,6]pyridino[2,3-d]pyrimidin-10-yl)}phenyl)ethoxy]phosphinooxy}propanenitrile (PPT) 44 (Reaction Scheme 10)

3-n-Butyl-6-[4-(2-hydroxyethyl)aminophenyl]uracil 40

A mixture of 6-chloro-3-n-butyluracil (10.4 g, 51.3 mmol), 2-(4-aminophenyl)ethanol (10.0 g, 72.9 mmol) and ethyldiisopropylamine (18 ml, 0.1 mol) was heated with stirring under argon on a 150° oil bath for 1 hr 20 min. The mixture was cooled to room temperature, diluted with 50 ml of water, treated with 10 ml of acetic acid and stirred for crystallization overnight. A precipitated solid was filtered, washed with 2% acetic acid, dried on filter and dissolved in 100 ml of hot 96% ethanol. To the solution 100 ml of hot water was added followed by 1.0 g of charcoal. The mixture was filtered hot and crystallized on ice. Yellow solid was collected by filtration and dried in vacuum to yield 10.7 g of 40, mp 207–208 ° C. $^1$H NMR (DMSO-$d_6$) δ 0.88 (t, 3H, J=7.3 Hz, $CH_3$), 1.25 (m, 2H, $CH_2$), 1.46 (m, 2H, $CH_2$), 2.70 (t, 2H, J=6.8Hz, $CH_2$), 3.60 (dd, 2H, J=11.8, 6.8Hz, $CH_2$), 3.68 (t, 2H, J=7.3Hz, $CH_2$), 4.62 (t, 1H, J=5.3 Hz, OH), 4.73 (d, 1H, J=1.8 Hz, 5-H), 7.10 (d, 2H, J=8.4 Hz, ArH), 7.23 (d, 2H, J=8.4 Hz, ArH), 7.10 (s, 1H, NH), 10.37 (s, 1H, NH).

3-n-Butyl-10-[(2-hydroxyethyl)phenyl]pyrido[2,3-d;6,5-d']dipyrimidine-2,4,6,8-(3H,7H,9H,10H)-tetrone.41

A solution of 40 (6.6 g, 20 mmol) and 5-formyl-2,4,6-trichloropyrimidine (5.85 g, 27.7 mmol) in 80 ml of dry DMF was stirred at RT for 8 hr and slowly diluted with 80 ml of water. The solution produced a solid upon refrigeration for 2 days. The product was isolated by filtration, washed with cold 50% ethanol (50 ml) and 25% ethanol (50 ml) and dried in vacuum to yield 8.16 g (96%) 41 as a colorless solid, mp 205–215 ° C. (decomp). $^1$H NMR (DMSO-$d_6$) δ 0.88 (t, 3H, J=7.2 Hz, $CH_3$), 1.27 (m, 2H, $CH_2$), 1.48 (m, 2H, $CH_2$), 2.81–2.90 (m, 2H, $CH_2$), 3.71–3.85 (m, 4H, $CH_2$), 4.50 (br. s, 5H, OH, NH, $H_2O$), 7.26 (d, 2H, J=8.4 Hz, ArH), 7.44 (d, 2H, J=8.4 Hz, ArH), 8.62 (s, 1H, 5-H).

3-n-Butyl-5,10-dihydro-10-[(2-hydroxyethyl)phenyl]pyrido[2,3-d;6,5-d']dipyrimidine-2,4,6,8-(1H,3H,7H, 9H,10H)-tetrone. 42

To a suspension 41 (7.91 g, 18.7 mmol) in 300 ml of 25% aq. $NH_3$ was added $Na_2S_2O_4$ (13.8 g, 85%, 67 mmol) and slowly heated to 60° with stirring. The mixture was stirred at 60° for 40 min, diluted with water (100 ml) and stirred for additional 1 hr at the same temperature. A clear solution formed. The solution was partially evaporated to one half of its original volume, cooled with ice and neutralized with 50 ml of acetic acid to pH 5 to form a precipitate. The mixture was kept in refrigerator for complete crystallization, filtered and washed with cold water. The solid was dried in vacuum to yield 7.32 g (92%) of 42 as a white solid, mp 182–210 ° C. (decomp). $^1$H NMR (DMSO-$d_6$) δ 0.86 (t, 3H, J=7.3 Hz, $CH_3$), 1.23 (m, 2H, $CH_2$), 1.42 (m, 2H, $CH_2$), 2.80 (t, 2H, J=6.6 Hz, $CH_2$), 3.14 (s, 2H, 5-$CH_2$), 3.68 (m, 4H, $ArCH_2CH_2$), 4.64 (t, 1H, OH), 7.25 (d, 2H, J=8.3 Hz, ArH), 7.33 (d, 2H, J=8.3 Hz, ArH), 7.73 (br. s, 3H, NH).

44

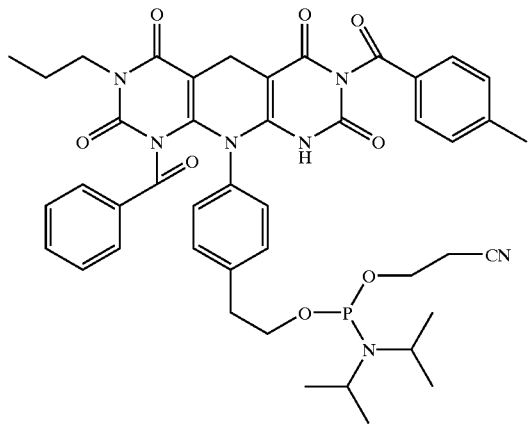

Solid 42 (1.2 g, 2.82 mmol) was evaporated with pyridine (10 ml), suspended in pyridine (13 ml), treated with Me₃SiCl (2.2 ml, 17.3 mmol) and stirred under argon at ambient temperature for 30 min. The reaction mixture was cooled with ice and treated slowly with toluoyl chloride (5 ml, 28.8 mmol). Stirring was continued at room temperature for 2 hr, and the solvent evaporated. The residue was treated with acetic acid (10 ml) followed by addition of water (10 ml). Precipitated oil was extracted with hexanes (3×50 ml), and the residue that was insoluble in hexanes was evaporated with water. The residue was suspended in 96% ethanol (10 ml) and filtered to recover 0.3 g of the starting material. The mother liquor was diluted with water to precipitate bis-toluoyl derivative as an oil. The oil was dried in vacuum to give 0.96 g (52%) of 43 as a solid foam. This compound without further purification was converted into phosphoramidite by the following procedure. The solid was evaporated with acetonitrile, dissolved in 25 ml of dichloromethane, treated with diisopropylammonium tetrazolide (0.54 g, 3.13 mmol) followed by 2-cyanoethyl tetraisopropylphosphorodiamidite (0.88 g, 2.9 mmol). The reaction mixture was stirred under argon for 1 hr, treated with methanol (1 ml), taken into EtOAc (100 ml), washed with sat. NaCl solution and dried over $Na_2SO_4$. The solution was evaporated, purified by HPLC on silica gel column using a gradient system 0–50% B; $CH_2Cl_2$-hexanes-$NEt_3$ (15:30:1) (A); EtOAc (B); detected at 320 nm. The main fraction was evaporated giving a colorless foam, 0.79 g (33%) of AG1 phosphoramidite 44. $^1$H NMR (CDCl₃) δ 0.92 (t, 3H, J=7.3 Hz, CH₃), 1.07–1.42 (m, 14H, 4×CH₃ (i-Pr), CH₂ (Bu)), 1.50–1.65 (m, 2H, CH₂ (Bu)), 2.35–2.60 (m, 2H, CH₂CN), 2.40 (s, 3H, CH₃Ar), 2.46 (s, 3H, CH₃Ar), 2.95–3.13 (m, 4H, 2×CH (i-Pr), CH₂ (Bu)), 3.45–3.60 (m, 2H, OCH₂), 3.80–4.02 (m, 4H, ArCH₂CH₂), 3.82 (s, 2H, 5-CH₂), 7.15–7.35 (m, 8H, ArH (Tol)), 7.45 (s, 1H, NH), 7.73 (br. s, 3H, NH), 7.95 (d, 2H, J=8.0 Hz, ArH), 8.05 (d, 2H, J=8.0 Hz, ArH). $^{31}$P NMR (CDCl₃) δ (ppm, H₃PO₄) 143.2 (s).

EXAMPLE 11

N-{3-[4-[(1Z)-1-aza-2-(Dimethylamino)prop-1-enyl]-1-(5-{[bis(4-methoxyphenyl)phenylmethoxy}methyl}-4-{[bis(methylethyl)amino](2-cyanoethyl)phophinooxy}oxolan-2-yl)pyrazolo [5,4-d]pyrimidin-3-yl]propyl}[2-({4-[(2-chloro-4-nitrophenyl)diazenyl]phenyl}ethylamino)ethoxy]carboxamide (50) (Reaction Scheme 11)

4-Amino-1-(2-deoxy-β-D-erythro-pentofuranosyl)-3-(3-trifluoroacetimidopropyn-1-yl)pyrazolo[3,4-d]pyrimidine (46; n=1)

To a mixture of 45 (1.96 g, 5.20 mmol), CuI (103 mg, 0.54 mmol) and tetrakis[triphenylphosphine]palladium[0] (317 mg, 0.276 mmol) in 10 ml of anhydrous DMF was added anhydrous triethylamine (1.1 ml) followed by propargyl trifluoroacetimide (1.50 g, 9.88 mmol). The reaction mixture was stirred under argon for 4 h. The solvent DMF was removed by evaporation and the residual oil was purified by silica gel chromatography eluting with 7% methanol in ethyl acetate. The product fractions were pooled and evaporated affording a foam: 2.16 g (99%) yield.

4-Amino-1-(2-deoxy-β-D-erythro-pentofuranosyl)-3-(3-aminopropyl)pyrazolo[3,4-d]pyrimidine (47; n=1)

To a solution of 46 (2.10 g, 5.25 mmol) in 50 ml of ethanol, containing 0.300 mg of 5% palladium on carbon (preactivated with formic acid), was added 1.0 ml of 4 M triethylammonium formate buffer (pH 6.5). The mixture was shaken under 40 psi of hydrogen gas for 18 h. The mixture was filtered through Celite and the filtrate was evaporated affording a solid. 1.8 g (85%) yield.

The solid was stirred in 15 ml of concentrated ammonium hydroxide (sealed flask) for 12 h and then evaporated to dryness. The solid (47) was evaporated from dry acetonitrile and stored under vacuum: 1.74 g yield.

Synthesis of 48 (n=1, q=2, R₅=CH₃CH₂—, R₅, R₅= H, R₁=2-Cl, R₅=4-NO₂)

A solution of 47 (0.90 g, 2.92 mmol) and 7 (1.59 g, 2.92 mmol) was stirred in 5.0 ml of anhydrous dimethylformamide, containing 1.0 ml of triethylamine, at 50° C. for 1.0 h. The solution was evaporated to dryness and the residue was purified by silica gel chromatography eluting with a gradient of 0–20% methanol in ethyl acetate. The product fractions were evaporated affording an amorphous solid: 0.74 g (37%) yield.

Synthesis of 49 (n=1, q=2, R₅=CH₃CH₂—, R₅, R₅= H, R₁=2-Cl, R₅=4-NO₂)

To a solution of 48 (0.71 g, 1.03 mmol) and N,N-dimethylacetamide dimethylacetal (1.9 ml) in 5.0 ml of dimethylacetamide was added 2.0 ml of triethylamine. The solution was stirred for 18 hrs. and then evaporated to dryness affording an oil: 0.75 g (100%) yield.

Synthesis of 50 (n=1, q=2, R₅=CH₃CH₂—, R₅, R₅= H, R₁=2-Cl, R₅=4-NO₂)

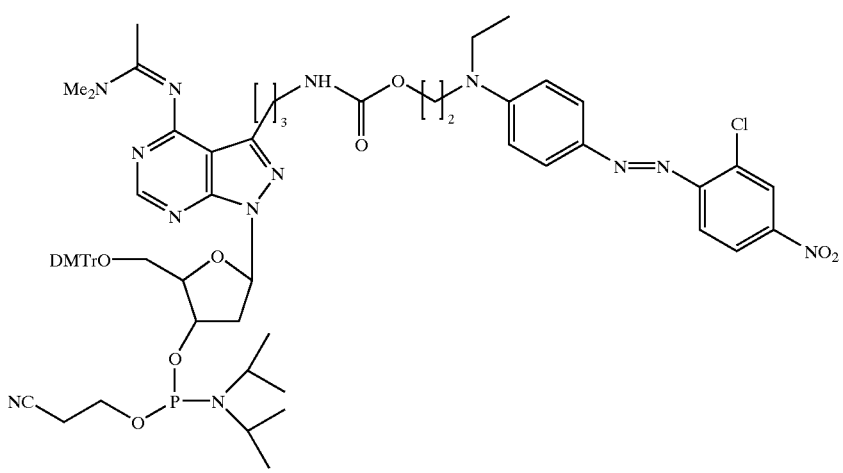

50

Dimethoxytrityl chloride (0.42 g) was added to a solution of 49 (0.75 g, 1.03 mmol) in 10 ml of dry pyridine. The solution was stirred for 4.0 h. under argon and then poured into 200 ml of 5% sodium bicarbonate solution. The product was extracted with 300 ml of ethyl acetate. The extract was dried over sodium sulfate and evaporated. The residue was purified by silica gel chromatography eluting with 10% methanol in ethyl acetate (1% triethylamine). The product fractions were evaporated affording a foam: 556 mg (57%) yield.

To a solution of the 5'-dimethoxytrityl derivative (540 mg, 0.567 mmol) in 15 ml of anhydrous methylene chloride, containing 0.30 ml of diisopropylethylamine, was added 2-cyanoethyl N,N-diisopropylchlorophosphoramidite (0.25 ml). After stirring for 30 minutes under argon at 25° C. the solution was treated with 1.0 ml of methanol and diluted with 200 ml of ethyl acetate. The solution was washed with 200 ml of 5% sodium bicarbonate solution and dried over sodium sulfate and evaporated. The crude product was purified by silica gel chromatography eluting with 5% methanol in ethyl acetate (2% triethylamine). The product fractions were evaporated affording a foam: 453-mg (76%) yield.

EXAMPLE 11

Synthesis of Fluorogenic Oligodeoxynucleotide Probes

The 3'-DPI$_3$ probes were prepared by automated DNA synthesis from a DPI$_3$-modified glass support using methods described earlier (Lukhtanov et al. Biorg. Chem., 7: 564–567 (1996). Oligonucleotide synthesis was performed on an ABI 394 synthesizer according to the protocol supplied by the manufacturer except that 0.015 M (instead of the standard 0.1 M) iodine solution was utilized in the oxidation step to avoid iodination of the CDPI$_3$ moiety. To prevent extension during PCR, probes without 3'-CDPI$_3$ were prepared with the 3'-hydroxyhexyl phosphate as previously described (Gamper et al. Biochem. 36: 14816–14826 (1997). The quencher phosphoramidites were added to the CPG and standard β-cyanoethylphosphoramidites and reagents (Glen Research, Sterling, Va.) were used in oligonucleotide synthesis. 6-Carboxyfluorescein (6-FAM) phosphoramidite (Glen Research) was used to introduce the 5'-reporter dyes. Alternatively TAMRA-dU phosphoramidite (Glen Research), cy3 or cy5 phosphoramidite (Glen Research), resorufin phosphoramidite, coumarin phosphoramidite, or AG phosphoramidite was used to introduce the indicated 5'-fluorophore. 5'-Hexylamine phosphoramidite (Glen Research) was incorporated into certain ODNs for post-synthetic conjugation of the 3'-quencher dye tetramethyl-rhodamine (TAMRA). After deprotection, all oligonucleotides were reverse-phase HPLC purified and isolated as the sodium salts by butanol concentration/sodium perchlorate precipitation (Milesi et al. Methods Enzym. 313: 164–73 (1999).

EXAMPLE 12

Post-synthetic Conjugation of ODNs with TAMRA

TAMRA NHS ester (Glen Research) was used to acylate the hexylamine linkers in certain ODNs according to the protocol supplied by the manufacturer. The resulting CDPI$_3$-probes with two conjugated dyes were purified by denaturing gel electrophoresis using 8% polyacrylamide. The desired bands were excised and the gel slices were incubated overnight at 37° C. in 10 mL of 100 mM Tris-HCl, 10 mM triethylammonium chloride, 1 mM EDTA (pH 7.8). The products were isolated from the extract by reverse phase HPLC, butanol concentration and sodium perchlorate precipitation. The pellets were dissolved in water and the concentrations were determined spectrophotometrically. A nearest neighbor model (Cantor, et al. Biopolymers 9: 1059–1077 (1970) was applied to calculate extinction coefficients ($\epsilon_{260}$) of ODNs. For the conjugates and probes, extinction coefficients were calculated as a sum of $\epsilon_{260}$ for the ODN and the incorporated residues of DPI$_3$ (68,000 M$^{-1}$, cm$^{-1}$), 6-FAM (22,800 M$^{-1}$, cm$^{-1}$), TAMRA (34,000 M$^{-1}$, cm$^{-1}$) and quencher (11,300 M$^{-1}$, cm$^{-1}$).

EXAMPLE 13

Digestion of Oligonucleotides by Snake Venom Phosphodiestaerase

Oligonucleotides were digested with snake venom phosphodiesterase (PDE) to study the fluorescence quenching potential of various quenchers. 200 nM of oligonucleotide was taken in a buffer containing 40 mM of NaCl, 20 mM of Tris (pH 8.9), 5 mM of MgCl$_2$ and 0.025% of BSA. Initial fluorescence was read on a LS50B fluorimeter (Perkin-Elmer Corporation, Foster City, Calif.) before the addition of phosphodiesterase (Pharmacia, Piscataway, N.J.) 54 units of enzyme was added to the reaction mixture and incubated at 37° C. for 16 hrs. The final fluorescence was then measured using the LS50B. The ratio of final fluorescence to the initial fluorescence represents the signal to noise ratio (S/N) of the quenchers. Independently the kinetics of digestion reactions were monitored using the LS50B to determine the time required for complete digestion of oligonucleotides.

EXAMPLE 14

5' Nuclease PCR Assay

CDPI$_3$-conjugated oligonucleotides were conjugated with a fluorophore, FAM at the 5' end and various quenchers were conjugated through a linker at the 3' end by the methods discussed above. 5' nuclease assays were performed with the above oligonucleotides to determine the quenching ability of the various quenchers under investigation. Fluorescent monitoring was performed in an Idaho Technologies LC-24 LightCycler. Each reaction contained PCR buffer (40 mM NaCl, 20 mM Tris HCl, pH 8.9, 5 mM MgSO$_4$, 0.05% bovine serum albumin), 125 mM each dNTP, 0.5 mM each primer, 0.1 mM fluorescent CDPI$_3$ probe, 0.5 U/10 mL Taq polymerase and 0.1 ng/10 mL of synthetic DNA as template. The cycling program was 50 cycles (or as indicated) of 2 sec at 95° C., then 30 sec at the extension temperature (55–70°).

What is claimed is:

1. An oligonucleotide conjugate having the formula

FL-ODN-Q-MGB where ODN is an oligonucleotide or nucleic acid;

FL is a fluorophore covalently attached to the ODN through a linker having the length of 0 to approximately 30 atoms, and Q is a quencher moiety covalently attached to the ODN through a linker having the length of 0 to approximately 30 atoms, the quencher moiety having the structure

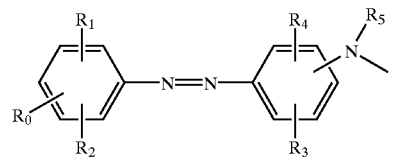

where $R_0$, $R_1$, $R_2$, $R_3$ and $R_4$ are independently —H, halogen, —O(CH$_2$)$_n$CH$_3$, —(CH$_2$)$_n$CH$_3$ where n=0 to 5, —NO$_2$, —SO$_3$, —N[(CH$_2$)$_{n'}$CH$_3$]$_2$ where n'=0 to 5 or —CN, and $R_5$=—H, —(CH$_2$)$_{n''}$CH$_3$ or —(CH$_2$)$_{n''}$— where n"=0 to 5, and MGB is a minor groove binder moiety covalently attached to the ODN moiety or to the quencher moiety through a linker having the length of 0 to approximately 30 atoms.

2. An oligonucleotide conjugate in accordance with claim 1 where the MGB moiety is attached to the quencher moiety, and the covalently bonded MGB-Q moiety has the structure

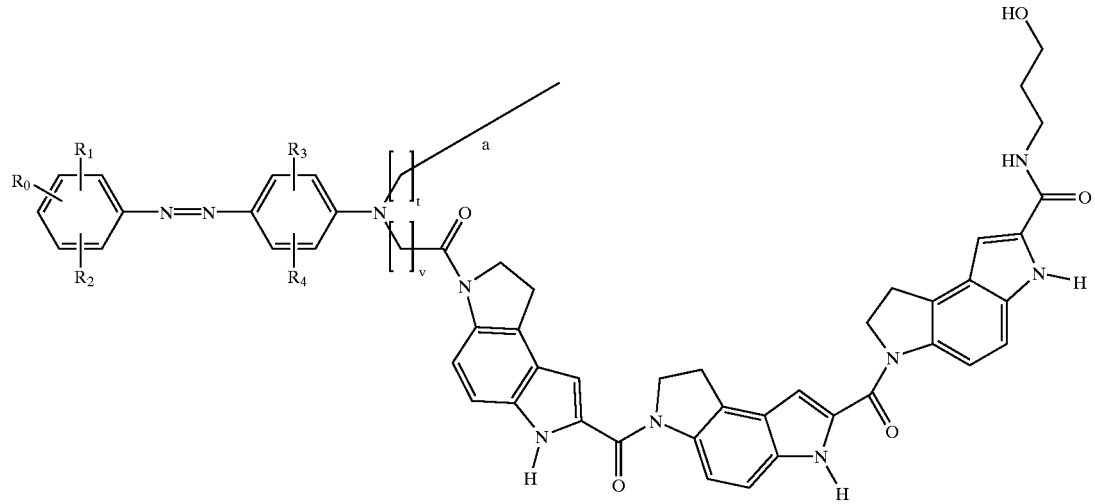

where t and v independently are 1 to 20, and the valence bond designated a attaches the MGB-Q moiety to the ODN moiety.

3. An oligonucleotide conjugate in accordance with claim 2 where $R_0$ is H, $R_1$ is NO$_2$ in the 4 position of the benzene nucleus, $R_2$ is H or Cl in the 2 position of the benzene nucleus, and $R_3$ and $R_4$ are hydrogen.

4. An oligonucleotide conjugate in accordance with claim 1 wherein said minor groove binder moiety (MGB) is attached to the quencher moiety through a linker having the length of 0 to approximately 30 atoms.

5. An oligonucleotide conjugate of the formula

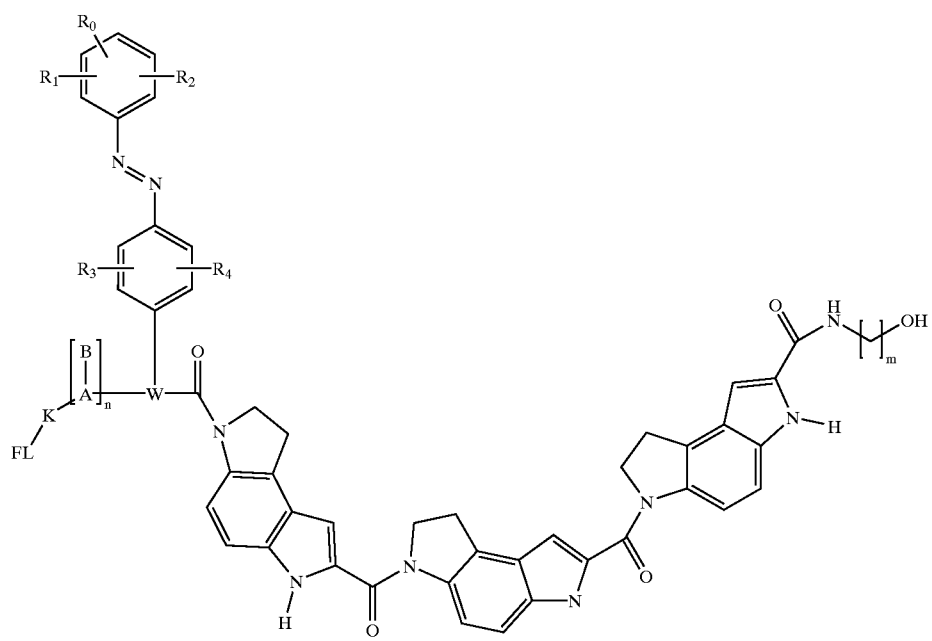

wherein $R_0$, $R_1$, $R_2$, $R_3$ and $R_4$ are independently —H, halogen, —O(CH$_2$)$_{n*}$CH$_3$, —(CH$_2$)$_{n*}$CH$_3$ where n*=0 to 5, —NO$_2$, —SO$_3$, —N[(CH$_2$)$_{n'}$CH$_3$]$_2$ where n'=0 to 5 or —CN;

FL is a fluorophore moiety with emission wavelengths in the range of about 300 to about 800 nm;

K is a linker from 1 to approximately 30 atoms in length;

[A-B]$_n$ symbolizes an ODN, DNA, RNA or PNA or any combination thereof, where A is the sugar phosphate backbone where the sugar and the phosphate may independently be modified; B is a heterocyclic base, where B is independently selected from purine, pyrimidine, pyrazolo[3,4-d]pyrimidine, 7-substituted pyrazolo[3,4-d]pyrimidine-, 7-deazapurine, 7-substituted 7-deazapurine, and modified purine- and pyrimidine-bases, and where the DNA, RNA, PNA or ODN can include any combinations of these bases, and n, the number of nucleotide units in said DNA, RNA, PNA or ODN, is from about 5 to 100;

W is a linker of a length of 1 to approximately 30 atoms, selected from the group consisting of C, O, N, S, and P; and m is an integer having the values of 1 to 20.

6. An oligonucleotide conjugate in accordance with claim 5 where $R_0$ is H, $R_1$ is NO$_2$ in the 4 position of the benzene nucleus, $R_2$ is H or Cl in the 2 position of the benzene nucleus, and $R_3$ and $R_4$ are hydrogen.

7. An oligonucleotide conjugate in accordance with claim 5 where said fluorophore moiety has the structure:

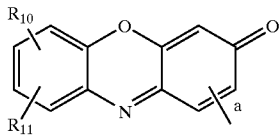

where $R_{10}$ and $R_{11}$ independently are H, —OR$_{12}$, —NH(R$_{13}$), —N(R$_{12}$)$_2$, halogen, —O(CH$_2$)$_n$CH$_3$, —(CH$_2$)$_n$CH$_3$, —NO$_2$, —SO$_3$, —C(=O)NH$_2$, —N[(CH$_2$)$_n$CH$_3$]$_2$ or —CN where n=0 to 5 and $R_{12}$ and $R_{13}$ are each independently alkyl of 1 to 10 carbons or alkanoyl of 1 to 10 carbons; and the valence bond designated a symbolizes covalent attachment of the fluorophore to the linker K.

8. An oligonucleotide conjugate having the formula

FL-ODN-MGB where ODN is an oligonucleotide or nucleic acid;

MGB is minor groove binder moiety covalently attached to the ODN moiety or to the quencher moiety through a linker having the length of 0 to approximately 30 atoms;

FL is a fluorophore covalently attached to the ODN through a linker having the length of 0 to approximately 30 atoms, said fluorophore moiety having the structure:

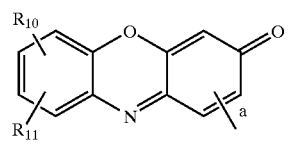

FL-2

$R_{10}$ and $R_{11}$ independently are H, —OR$_{12}$, —NH(R$_{13}$), —N(R$_{12}$)$_2$, halogen, —O(CH$_2$)$_n$CH$_3$, —(CH$_2$)$_n$CH$_3$, —NO$_2$, —SO$_3$, —C(=O)NH$_2$, —N[(CH$_2$)$_n$CH$_3$]$_2$ or —CN where n=0 to 5 and $R_{12}$ and $R_{13}$ are each independently alkyl of 1 to 10 carbons or alkanoyl of 1 to 10 carbons; and the valence bond designated a symbolizes covalent attachment of the fluorophore to the linker.

9. An oligonucleotide conjugate in accordance with claim 8 where $R_{10}$ is H and $R_{11}$ is H.

* * * * *

UNITED STATES PATENT AND TRADEMARK OFFICE
CERTIFICATE OF CORRECTION

PATENT NO.   : 6,727,356 B1
DATED        : April 27, 2004
INVENTOR(S)  : Reed et al.

It is certified that error appears in the above-identified patent and that said Letters Patent is hereby corrected as shown below:

Column 70,
Line 1, before "$R_{12}$" insert -- each --, then replace "and $R_{13}$ are each" with -- is --.
Line 1, after "independently" insert -- H, --.
Line 2, after "; and" insert -- $R_{13}$ is alkyl of 1 to 10 carbons or alkanoyl of 1 to 10 carbons; and --.
Line 31, delete "$R_{12}$ and $R_{13}$ are", then after "each", insert -- $R_{12}$ is --.
Line 32, after "independently" insert -- H, --.
Line 33, after "and" insert -- $R_{13}$ is alkyl of 1 to 10 carbons or alkanoyl of 1 to 10 carbons; and --.
Line 37, replace "$R_{10}$" with -- $R_{12}$ --.

Signed and Sealed this

Twelfth Day of October, 2004

JON W. DUDAS
*Director of the United States Patent and Trademark Office*